US009421314B2

(12) United States Patent
Plahey et al.

(10) Patent No.: US 9,421,314 B2
(45) Date of Patent: Aug. 23, 2016

(54) MEDICAL FLUID CASSETTES AND RELATED SYSTEMS AND METHODS

(75) Inventors: Kulwinder S. Plahey, Martinez, CA (US); Lynn Jensen, Syracuse, UT (US); Melvin D. Jensen, West Haven, UT (US); DeLoy Lindley, North Ogden, UT (US); Joseph Michael Fallon, Dixon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1339 days.

(21) Appl. No.: 12/836,740

(22) Filed: Jul. 15, 2010

(65) Prior Publication Data
US 2011/0015610 A1  Jan. 20, 2011

Related U.S. Application Data

(60) Provisional application No. 61/225,618, filed on Jul. 15, 2009.

(51) Int. Cl.
*A61M 1/28* (2006.01)

(52) U.S. Cl.
CPC .............. *A61M 1/28* (2013.01); *A61M 1/281* (2014.02); *A61M 2205/121* (2013.01)

(58) Field of Classification Search
CPC .............. A61M 1/1037; A61M 1/16; A61M 2205/12; A61M 5/16827; A61M 5/142; A61M 5/14224; A61M 2205/121; A61M 1/14; A61M 2205/128; A61M 1/28; A61M 1/281; F04B 43/02
USPC ..................... 604/500, 153, 28, 29
See application file for complete search history.

(56) References Cited

U.S. PATENT DOCUMENTS

| 329,773 A | 11/1885 | Perry |
| 2,383,193 A | 8/1945 | Herbert |
| 2,529,028 A | 11/1950 | Landon |
| 2,658,526 A | 11/1953 | Porter |
| 2,711,134 A | 6/1955 | Hughes |
| 2,755,745 A | 7/1956 | Lewis |
| 2,871,795 A | 2/1959 | Smith |
| 2,886,281 A | 5/1959 | Canalizo |
| 3,083,943 A | 4/1963 | Stewart et al. |

(Continued)

FOREIGN PATENT DOCUMENTS

| DE | 2628238 | 1/1978 |
| DE | 2827648 | 1/1979 |

(Continued)

OTHER PUBLICATIONS

International Search Report and Written Opinion, PCT/US2010/041976, mailed Dec. 2, 2010.

(Continued)

*Primary Examiner* — Bhisma Mehta
*Assistant Examiner* — Brandy S Lee
(74) *Attorney, Agent, or Firm* — Fish & Richardson P.C.

(57) ABSTRACT

A medical fluid delivery cassette configured for use with a medical fluid pumping system and related systems and methods. The medical fluid delivery cassette includes a base and a membrane that together define a fluid pump chamber. The medical fluid delivery cassette further includes a member configured to apply an outward force to an inner surface of the membrane.

42 Claims, 31 Drawing Sheets

(56) References Cited

U.S. PATENT DOCUMENTS

| | | | |
|---|---|---|---|
| 3,323,786 A * | 6/1967 | Boschi | 267/292 |
| 3,556,465 A | 1/1971 | Little | |
| 3,671,814 A | 6/1972 | Dick | |
| 3,689,025 A | 9/1972 | Kiser | |
| 3,741,687 A | 6/1973 | Nystroem | |
| 3,777,625 A | 12/1973 | Andres | |
| 3,781,141 A | 12/1973 | Schall | |
| 3,880,053 A | 4/1975 | Trechsel et al. | |
| 3,927,955 A | 12/1975 | Spinosa et al. | |
| 3,966,358 A | 6/1976 | Heimes et al. | |
| 3,985,135 A | 10/1976 | Carpenter et al. | |
| 4,026,669 A | 5/1977 | Leonard et al. | |
| 4,047,844 A | 9/1977 | Robinson | |
| 4,050,859 A | 9/1977 | Vork | |
| 4,091,812 A | 5/1978 | Helixon et al. | |
| 4,121,584 A | 10/1978 | Turner et al. | |
| 4,152,098 A | 5/1979 | Moody et al. | |
| 4,158,530 A | 6/1979 | Bernstein | |
| 4,178,940 A | 12/1979 | Au | |
| 4,273,121 A | 6/1981 | Jassawalla | |
| 4,303,376 A | 12/1981 | Siekmann | |
| 4,304,260 A | 12/1981 | Turner et al. | |
| 4,322,201 A | 3/1982 | Archibald | |
| 4,333,452 A | 6/1982 | Au | |
| 4,370,983 A | 2/1983 | Lichtenstein | |
| 4,382,753 A | 5/1983 | Archibald | |
| 4,410,322 A | 10/1983 | Archibald | |
| 4,412,553 A | 11/1983 | Kopp et al. | |
| 4,436,620 A | 3/1984 | Bellotti et al. | |
| 4,453,932 A | 6/1984 | Pastrone | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,490,621 A | 12/1984 | Watabe et al. | |
| 4,536,201 A | 8/1985 | Brorsson et al. | |
| 4,558,715 A | 12/1985 | Walton et al. | |
| 4,569,378 A | 2/1986 | Bergandy | |
| 4,583,920 A | 4/1986 | Lindner | |
| 4,597,412 A | 7/1986 | Stark | |
| 4,610,605 A | 9/1986 | Hartley | |
| 4,623,328 A | 11/1986 | Hartranft | |
| 4,628,499 A | 12/1986 | Hammett | |
| 4,639,245 A | 1/1987 | Pastrone et al. | |
| 4,643,713 A | 2/1987 | Viitala | |
| 4,657,490 A | 4/1987 | Abbott | |
| 4,662,598 A | 5/1987 | Weingarten | |
| 4,662,906 A | 5/1987 | Matkovich et al. | |
| 4,676,467 A | 6/1987 | Palsulich | |
| 4,690,621 A | 9/1987 | Swain | |
| 4,703,913 A | 11/1987 | Hunkapiller | |
| 4,705,259 A | 11/1987 | Dolben et al. | |
| 4,710,166 A | 12/1987 | Thompson et al. | |
| 4,735,558 A | 4/1988 | Kienholz et al. | |
| 4,778,451 A | 10/1988 | Kamen | |
| 4,786,240 A | 11/1988 | Koroly et al. | |
| 4,808,161 A | 2/1989 | Kamen | |
| 4,826,482 A | 5/1989 | Kamen | |
| 4,840,542 A | 6/1989 | Abbott | |
| 4,842,584 A | 6/1989 | Pastrone | |
| 4,846,636 A | 7/1989 | Danby et al. | |
| 4,850,980 A | 7/1989 | Lentz et al. | |
| 4,858,883 A | 8/1989 | Webster | |
| 4,902,282 A | 2/1990 | Bellotti et al. | |
| 4,906,260 A | 3/1990 | Emheiser et al. | |
| 4,927,411 A | 5/1990 | Pastrone et al. | |
| 4,950,134 A | 8/1990 | Bailey et al. | |
| 4,974,754 A | 12/1990 | Wirz | |
| 4,976,162 A | 12/1990 | Kamen | |
| 4,995,864 A | 2/1991 | Bartholomew et al. | |
| 4,997,464 A | 3/1991 | Kopf | |
| 5,002,471 A | 3/1991 | Perlov | |
| 5,006,050 A | 4/1991 | Cooke et al. | |
| 5,011,380 A | 4/1991 | Kovacs | |
| 5,036,886 A | 8/1991 | Olsen et al. | |
| 5,061,236 A | 10/1991 | Sutherland et al. | |
| 5,088,515 A | 2/1992 | Kamen | |
| 5,098,262 A | 3/1992 | Wecker et al. | |
| 5,100,380 A | 3/1992 | Epstein | |
| 5,100,699 A | 3/1992 | Roeser | |
| 5,116,021 A | 5/1992 | Faust et al. | |
| 5,116,316 A | 5/1992 | Sertic et al. | |
| 5,146,713 A | 9/1992 | Grafius | |
| 5,151,019 A | 9/1992 | Danby et al. | |
| 5,167,837 A | 12/1992 | Snodgrass et al. | |
| 5,171,029 A | 12/1992 | Maxwell et al. | |
| 5,178,182 A | 1/1993 | Kamen | |
| 5,193,990 A | 3/1993 | Kamen et al. | |
| 5,211,201 A | 5/1993 | Kamen et al. | |
| 5,241,985 A | 9/1993 | Faust et al. | |
| 5,247,434 A | 9/1993 | Peterson et al. | |
| 5,249,932 A | 10/1993 | Van Bork | |
| 5,252,044 A | 10/1993 | Raines et al. | |
| 5,259,352 A | 11/1993 | Gerhardy et al. | |
| 5,267,956 A * | 12/1993 | Beuchat | 604/30 |
| 5,279,556 A | 1/1994 | Goi et al. | |
| 5,302,093 A | 4/1994 | Owens et al. | |
| 5,324,422 A | 6/1994 | Colleran et al. | |
| 5,330,425 A | 7/1994 | Utterberg | |
| 5,342,182 A | 8/1994 | Montoya et al. | |
| 5,344,292 A * | 9/1994 | Rabenau et al. | 417/413.1 |
| 5,350,357 A | 9/1994 | Kamen et al. | |
| D351,470 S | 10/1994 | Scherer et al. | |
| 5,353,837 A | 10/1994 | Faust | |
| 5,378,126 A | 1/1995 | Abrahamson et al. | |
| 5,395,351 A | 3/1995 | Munsch | |
| 5,413,626 A | 5/1995 | Bartsch | |
| 5,415,528 A | 5/1995 | Ogden et al. | |
| 5,421,208 A | 6/1995 | Packard et al. | |
| 5,421,823 A | 6/1995 | Kamen et al. | |
| 5,427,509 A | 6/1995 | Chapman et al. | |
| 5,431,626 A | 7/1995 | Bryant et al. | |
| 5,431,627 A | 7/1995 | Pastrone et al. | |
| 5,431,634 A | 7/1995 | Brown | |
| 5,438,510 A | 8/1995 | Bryant et al. | |
| 5,441,636 A | 8/1995 | Chevallet et al. | |
| 5,445,506 A | 8/1995 | Afflerbaugh et al. | |
| 5,447,286 A | 9/1995 | Kamen et al. | |
| 5,462,416 A | 10/1995 | Dennehey et al. | |
| 5,462,417 A | 10/1995 | Chapman | |
| 5,474,683 A | 12/1995 | Bryant et al. | |
| 5,478,211 A | 12/1995 | Dominiak et al. | |
| 5,480,294 A | 1/1996 | Di Perna et al. | |
| 5,482,438 A | 1/1996 | Anderson et al. | |
| 5,482,440 A | 1/1996 | Dennehey et al. | |
| 5,482,446 A | 1/1996 | Williamson et al. | |
| 5,484,239 A | 1/1996 | Chapman et al. | |
| 5,486,286 A | 1/1996 | Peterson et al. | |
| 5,514,069 A | 5/1996 | Brown et al. | |
| 5,538,405 A | 7/1996 | Patno et al. | |
| 5,540,568 A | 7/1996 | Rosen et al. | |
| 5,547,453 A | 8/1996 | Di Perna | |
| 5,551,850 A | 9/1996 | Williamson et al. | |
| 5,551,941 A | 9/1996 | Howell | |
| 5,551,942 A | 9/1996 | Brown et al. | |
| 5,554,013 A | 9/1996 | Owens et al. | |
| 5,570,716 A | 11/1996 | Kamen et al. | |
| 5,573,385 A | 11/1996 | Chevallier | |
| 5,578,070 A | 11/1996 | Utterberg | |
| 5,586,868 A * | 12/1996 | Lawless et al. | 417/53 |
| 5,588,816 A | 12/1996 | Abbott et al. | |
| 5,593,290 A | 1/1997 | Greisch et al. | |
| 5,599,174 A | 2/1997 | Cook | |
| 5,609,572 A | 3/1997 | Lang | |
| 5,614,677 A | 3/1997 | Wamsiedler et al. | |
| 5,624,409 A | 4/1997 | Seale | |
| 5,628,908 A | 5/1997 | Kamen et al. | |
| 5,630,710 A | 5/1997 | Tune et al. | |
| 5,634,896 A | 6/1997 | Bryant et al. | |
| 5,640,995 A | 6/1997 | Packard et al. | |
| 5,641,405 A | 6/1997 | Keshaviah et al. | |
| 5,641,892 A | 6/1997 | Larkins et al. | |
| 5,643,205 A | 7/1997 | Utterberg | |
| 5,645,531 A | 7/1997 | Thompson et al. | |
| 5,658,133 A | 8/1997 | Anderson et al. | |

(56) References Cited

U.S. PATENT DOCUMENTS

| | | | |
|---|---|---|---|
| 5,669,764 A | 9/1997 | Behringer et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,718,567 A | 2/1998 | Rapp et al. |
| 5,741,125 A | 4/1998 | Neftel et al. |
| 5,743,169 A | 4/1998 | Yamada |
| 5,746,708 A | 5/1998 | Giesler et al. |
| 5,755,683 A | 5/1998 | Houle et al. |
| 5,764,034 A | 6/1998 | Bowman et al. |
| 5,769,387 A | 6/1998 | Perez |
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,902,096 A | 5/1999 | Behringer et al. |
| 5,906,598 A | 5/1999 | Giesler et al. |
| 5,921,951 A | 7/1999 | Morris |
| 5,925,011 A | 7/1999 | Faict et al. |
| 5,934,885 A | 8/1999 | Farrell et al. |
| 5,935,099 A | 8/1999 | Peterson et al. |
| 5,938,634 A | 8/1999 | Packard |
| 5,984,897 A | 11/1999 | Petersen et al. |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,106,246 A | 8/2000 | Steck et al. |
| 6,110,410 A | 8/2000 | Owens et al. |
| 6,118,207 A | 9/2000 | Ormerod et al. |
| 6,129,517 A | 10/2000 | Danby et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,164,621 A | 12/2000 | Bouchard et al. |
| 6,165,154 A | 12/2000 | Gray et al. |
| 6,168,394 B1 | 1/2001 | Forman et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,208,497 B1 | 3/2001 | Seale et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,312,412 B1 * | 11/2001 | Saied ..................... A61M 5/20 604/191 |
| 6,315,707 B1 | 11/2001 | Smith et al. |
| 6,315,754 B1 | 11/2001 | Daoud et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,383,158 B1 | 5/2002 | Utterberg |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,579,253 B1 | 6/2003 | Burbank et al. |
| 6,592,542 B2 | 7/2003 | Childers et al. |
| 6,595,948 B2 | 7/2003 | Suzuki et al. |
| 6,603,229 B1 | 8/2003 | Toye |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,752,599 B2 | 6/2004 | Park |
| 6,755,801 B2 | 6/2004 | Utterberg et al. |
| 6,758,975 B2 | 7/2004 | Peabody et al. |

(56) References Cited

U.S. PATENT DOCUMENTS

| | | |
|---|---|---|
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,957,952 B1 | 10/2005 | Steck et al. |
| 6,984,218 B2 | 1/2006 | Nayak et al. |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 | 8/2007 | Smith et al. |
| 7,267,661 B2 | 9/2007 | Susi |
| 7,273,465 B2 | 9/2007 | Ash |
| 7,306,578 B2 | 12/2007 | Gray et al. |
| 7,331,935 B2 | 2/2008 | Barere |
| 7,338,469 B2 | 3/2008 | Barker et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,133 B2 | 2/2010 | Scarborough et al. |
| 7,662,286 B2 | 2/2010 | Childers et al. |
| 7,699,966 B2 | 4/2010 | Qin et al. |
| 7,717,682 B2 | 5/2010 | Orr |
| 7,789,849 B2 | 9/2010 | Busby et al. |
| 7,815,595 B2 | 10/2010 | Busby et al. |
| 8,038,640 B2 | 10/2011 | Orr |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,409,441 B2 | 4/2013 | Wilt |
| 8,562,834 B2 | 10/2013 | Kamen et al. |
| 8,721,879 B2 | 5/2014 | van der Merwe et al. |
| 2001/0034502 A1 | 10/2001 | Moberg |
| 2001/0037763 A1 | 11/2001 | Deguchi et al. |
| 2001/0043450 A1 | 11/2001 | Seale et al. |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0098097 A1 | 7/2002 | Singh |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0194332 A1 | 10/2003 | Jahn et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1* | 1/2004 | Childers et al. ............ 604/5.01 |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1 | 7/2004 | Jahn et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0002823 A1 | 1/2006 | Feldstein |
| 2006/0079766 A1 | 4/2006 | Neer et al. |
| 2006/0079826 A1 | 4/2006 | Beden et al. |
| 2006/0195064 A1 | 8/2006 | Plahey et al. |
| 2007/0040454 A1 | 2/2007 | Freudenberger et al. |
| 2007/0112297 A1 | 5/2007 | Plahey et al. |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2007/0278155 A1 | 12/2007 | Lo et al. |
| 2008/0033346 A1 | 2/2008 | Childers et al. |
| 2008/0077068 A1 | 3/2008 | Orr |
| 2008/0125693 A1 | 5/2008 | Gavin et al. |
| 2008/0208103 A1 | 8/2008 | Demers et al. |
| 2008/0216898 A1 | 9/2008 | Grant et al. |
| 2008/0253912 A1 | 10/2008 | Demers et al. |
| 2009/0004033 A1 | 1/2009 | Demers et al. |
| 2009/0099498 A1 | 4/2009 | Demers et al. |

(56) References Cited

U.S. PATENT DOCUMENTS

| | | |
|---|---|---|
| 2009/0137940 A1 | 5/2009 | Orr |
| 2009/0169402 A1 | 7/2009 | Stenberg |
| 2009/0212248 A1 | 8/2009 | Kozak |
| 2010/0021313 A1 | 1/2010 | Devan et al. |
| 2010/0211044 A1 | 8/2010 | Dacquay et al. |
| 2010/0241062 A1 | 9/2010 | Morris et al. |
| 2010/0286614 A1 | 11/2010 | Ring |
| 2011/0020156 A1 | 1/2011 | Van Brunt et al. |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2011/0152785 A1 | 6/2011 | Chattaraj et al. |
| 2011/0274566 A1 | 11/2011 | Amirouche et al. |
| 2011/0293450 A1 | 12/2011 | Grimes et al. |
| 2012/0022354 A1 | 1/2012 | Beyer et al. |
| 2012/0065581 A1 | 3/2012 | Childers et al. |
| 2012/0073432 A1 | 3/2012 | Ingersoll et al. |
| 2012/0123322 A1 | 5/2012 | Scarpaci et al. |
| 2012/0209169 A1 | 8/2012 | Morris et al. |
| 2012/0224984 A1 | 9/2012 | Orr |
| 2012/0230844 A1 | 9/2012 | Farrell et al. |
| 2012/0232469 A1 | 9/2012 | Medina |
| 2012/0271226 A1 | 10/2012 | Farrell et al. |
| 2012/0308412 A1 | 12/2012 | Rochat |
| 2013/0118961 A1 | 5/2013 | Beden et al. |
| 2013/0118970 A1 | 5/2013 | Beden et al. |
| 2013/0183170 A1 | 7/2013 | Laermer |
| 2013/0184638 A1 | 7/2013 | Scarpaci et al. |
| 2013/0330208 A1 | 12/2013 | Ly et al. |
| 2013/0331774 A1 | 12/2013 | Farrell et al. |

FOREIGN PATENT DOCUMENTS

| | | |
|---|---|---|
| DE | 4006785 | 9/1990 |
| DE | 4336336 | 5/1994 |
| DE | 198 37 667 | 3/2000 |
| DE | 19919572 A1 | 11/2000 |
| DE | 100 42 324 | 2/2002 |
| DE | 100 46 651 | 4/2002 |
| DE | 19919572 C2 | 4/2002 |
| DE | 100 53 441 | 5/2002 |
| DE | 101 57 924 | 5/2002 |
| DE | 69618766 | 8/2002 |
| DE | 101 43 137 | 4/2003 |
| DE | 102007059239 A1 | 6/2009 |
| EP | 0257279 | 3/1988 |
| EP | 0314379 | 8/1991 |
| EP | 0410125 B1 | 8/1993 |
| EP | 0728509 | 8/1996 |
| EP | 0848193 | 6/1998 |
| EP | 0856321 | 8/1998 |
| EP | 0 947 814 B2 | 10/1999 |
| EP | 0 956 876 A1 | 11/1999 |
| EP | 1529545 | 5/2005 |
| GB | 1483702 | 8/1977 |
| GB | 2101232 | 1/1983 |
| GB | 2101232 A | 1/1983 |
| GB | 2331796 | 6/1999 |
| JP | 0396850 A | 4/1991 |
| JP | 04-191755 | 7/1992 |
| JP | 06-154314 | 6/1994 |
| JP | 06-002650 | 11/1994 |
| JP | 08028722 | 2/1996 |
| JP | 11-347115 | 12/1999 |
| JP | 2000-070358 | 3/2000 |
| JP | 2000346214 | 12/2000 |
| WO | WO 84/02473 | 7/1984 |
| WO | 8601115 | 2/1986 |
| WO | WO9415660 A1 | 7/1994 |
| WO | 9420155 | 9/1994 |
| WO | WO9625064 A3 | 9/1996 |
| WO | WO 97/16214 | 5/1997 |
| WO | WO 97/37703 | 10/1997 |
| WO | WO 98/22165 | 5/1998 |
| WO | WO9822167 A1 | 5/1998 |
| WO | WO 00/23140 | 4/2000 |
| WO | WO 00/33898 | 6/2000 |
| WO | WO 01/17605 | 3/2001 |
| WO | 0225146 | 3/2002 |
| WO | WO 02/25225 | 3/2002 |
| WO | WO2007006030 A3 | 6/2007 |
| WO | 2009071069 | 6/2009 |
| WO | WO2009071069 A1 | 6/2009 |
| WO | WO2010128914 A1 | 11/2010 |
| WO | WO2011045167 A1 | 4/2011 |

OTHER PUBLICATIONS

Liberty Cycler Operator's Manual, 2003-2004.
Newton IQ Cycler Operator Manual, Part No. 470203 Rev. F, 2000-2006.
Operator's Instructions, Fresenius 90/2 Peritoneal Therapy Cycler, Part No. 470016 Rev. B, 1991.
Gambro®, "DEHP-free cartridge blood sets," © Nov. 2004, Gambro, Inc., Lakewood, CO, 4 pp.
Gambro®, Prisma® HF 1000, "For Increased Filtration Capacity", © Aug. 2001, Gambro Renal Products, Inc., Lakewood, CO, 2 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™ anticipating critical care needs and taking our innovative response . . . to new heights," © 2004, Gambro Inc., Lakewood, CO, 8 pp.
Glenn Avolio, "Principles of Rotary Optical Encoders," Sensors Journal of Machine Perception, vol. 10, No. 4, pp. 10-18, 1993.
Manns, Markus et al., "The acu-men: A new device for continuous renal replacement therapy in acute renal failure," Kidney International, vol. 54, pp. 268-274, 1998.
Operator's Manual, Serena, Program Version 3.xx—English; Apr. 2002.
Sleep Safe Operating Instructions, Software Version 0.9, Part No. 677 805 1, Fresenius Medical Care, Aug. 2000.
Sleep Safe Technical Manual, Part No. 677 807 1; Aug. 2000.
Bolegoh, Gordon, "Pumps: Reference Guide", p. 24, 3rd edition, 2001.
Ronco et al., "Evolution of Machines for Automated Peritoneal Dialysis", in Automated Peritoneal Dialysis, Contributions to Nephrology, vol. 129, pp. 142-161, 1999.
Sleep Safe Operating Instructions, Software Version 0.5, Apr. 1999.
Sleep Safe Operating Instructions, Software Version 1.0, Oct. 2000.
Sleep Safe Technical Manual, Dec. 2001.
Sleep Safe Operating Instructions, Jan. 2002.
Sleep Safe Communicating Therapy, Mar. 1998.
Sleep Safe Kommunizierte Therapie, May 1998.
Innovative Technologies in Peritoneal Dialysis, Sleep Safe Concept, Oct. 13, 1999 (4 attachments).
TL™ Pump Brochure, TL Systems Corporation.
Google definition for Hall Effect Sensor, accessed Jul. 30, 2015.
Hall Sensor Effect—NPL Wayback Mar. 11, 2011. www.movingmagnet.com, Technologies, Magnetic and Hall effect Position Sensors.

* cited by examiner

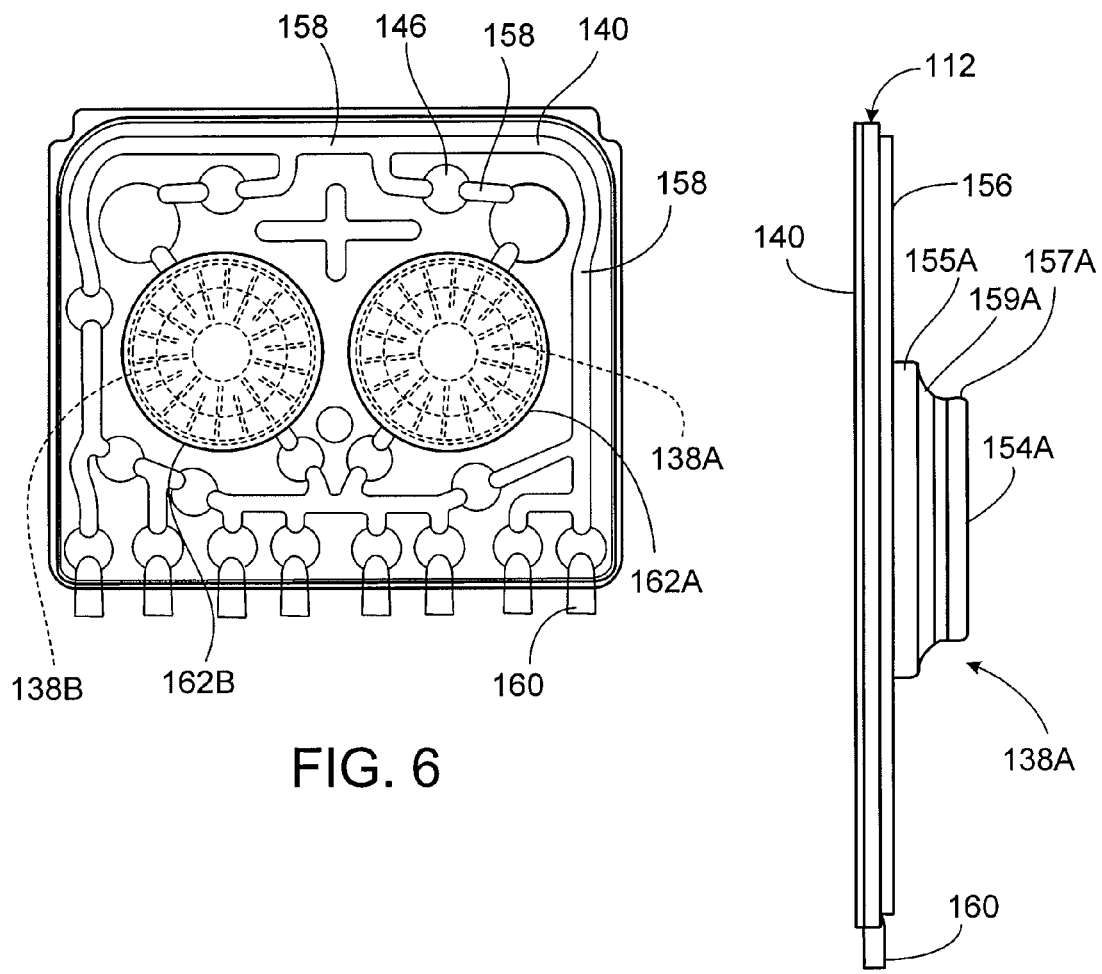

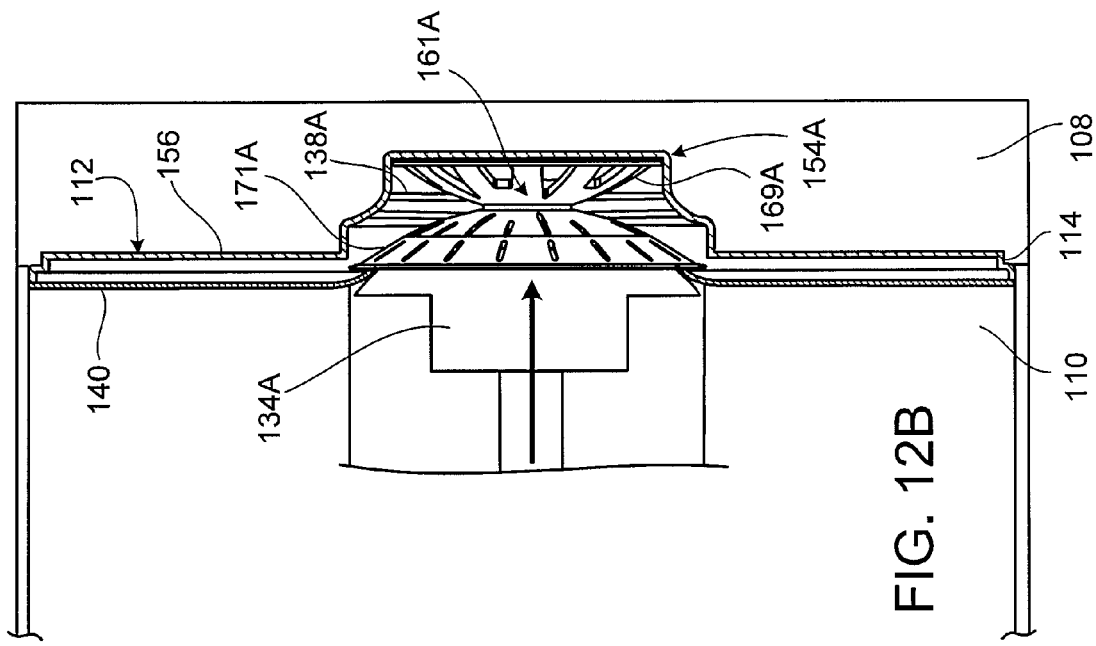
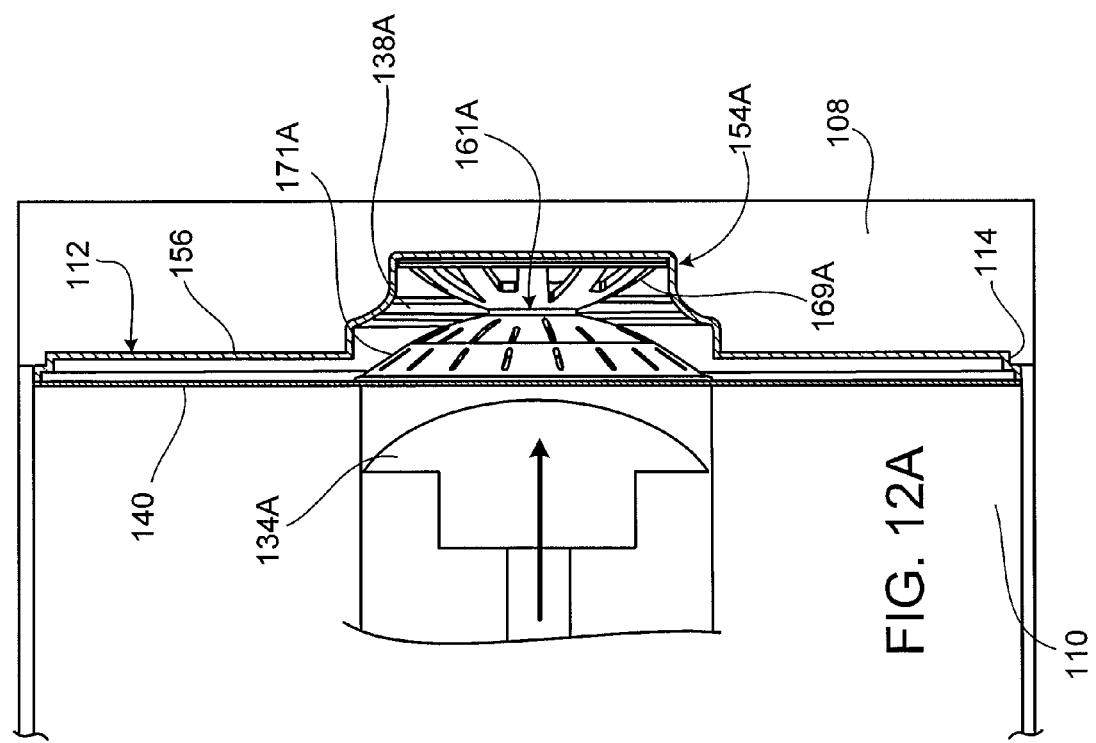

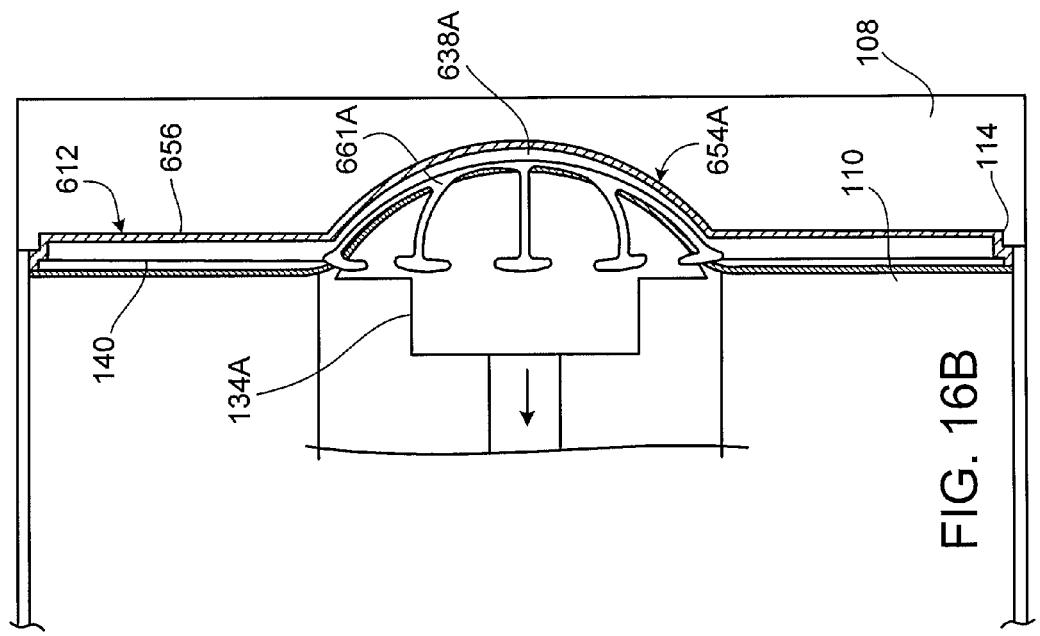
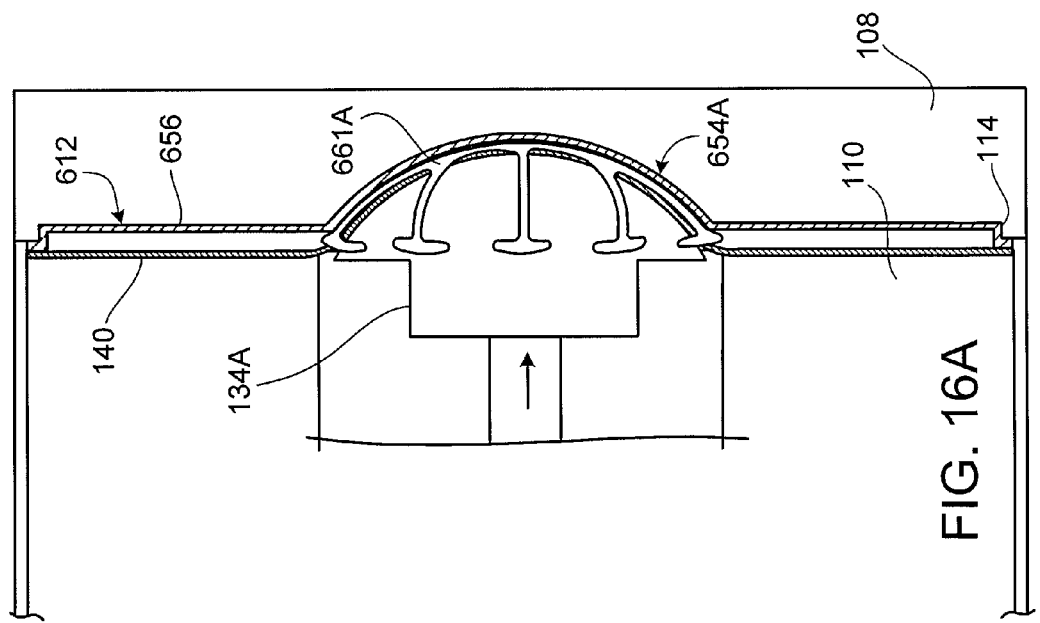

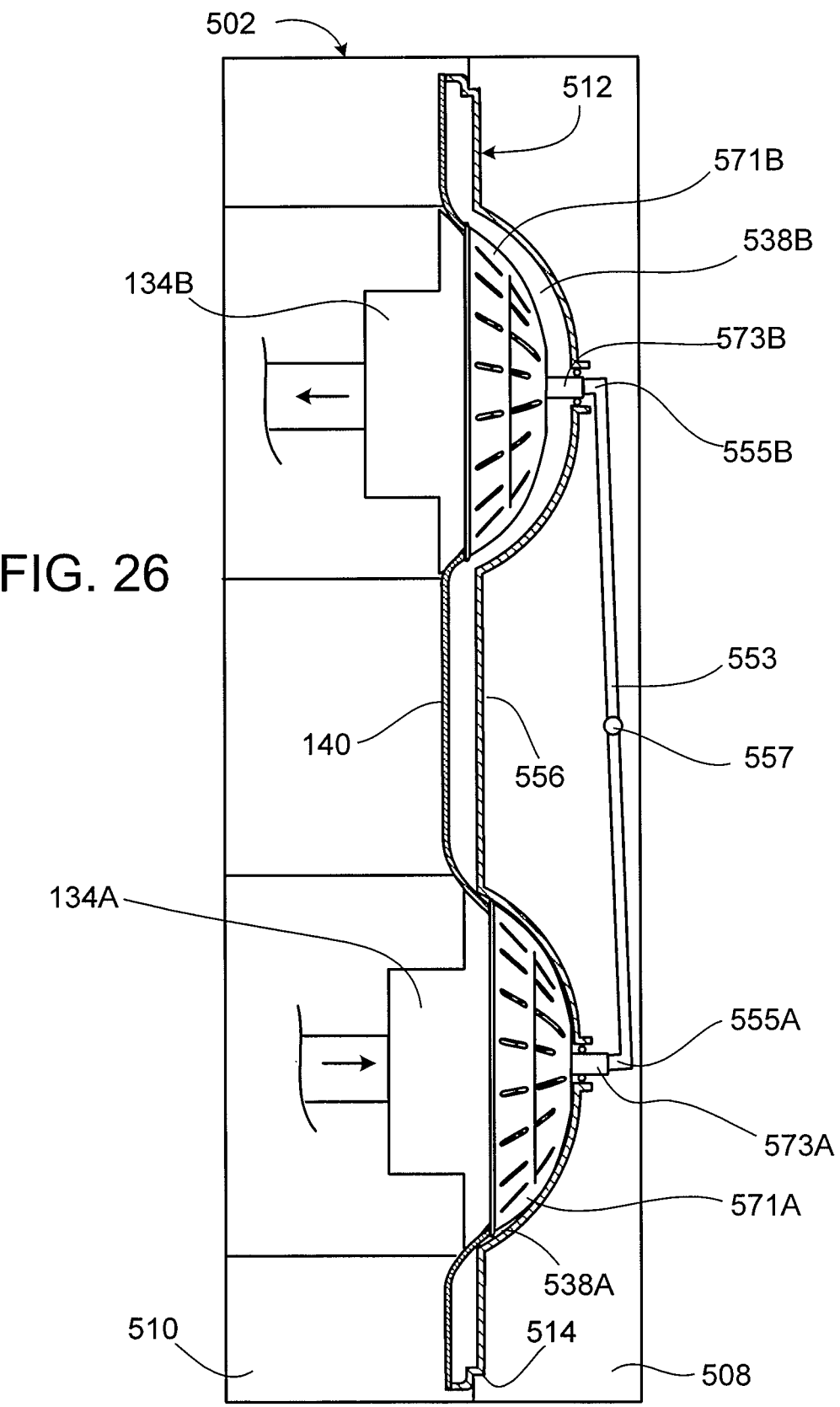

MEDICAL FLUID CASSETTES AND RELATED SYSTEMS AND METHODS

CROSS-REFERENCE TO RELATED APPLICATIONS

This application claims the benefit of U.S. Application Ser. No. 61/225,618, filed on Jul. 15, 2009.

TECHNICAL FIELD

This disclosure relates to medical fluid cassettes and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pumping system includes a medical fluid pumping machine defining a cassette enclosure and a medical fluid cassette configured to be disposed within the cassette enclosure of the medical fluid pumping machine. The medical fluid pumping machine includes a movable piston. The medical fluid cassette includes a base and a membrane attached to the base. The membrane and a region of the base cooperate to define a fluid pump chamber. The cassette is positionable within the cassette enclosure of the medical fluid pumping machine so that the membrane faces the piston and the membrane can be moved by the piston to decrease a volume of the fluid pump chamber. The medical fluid cassette also includes a member disposed within the fluid pump chamber and configured to apply an outward force to an inner surface of the membrane to increase the volume of the fluid pump chamber.

In another aspect of the invention, a medical fluid cassette includes a base and a membrane attached to the base. The membrane and a region of the base cooperate to define a fluid pump chamber. A member is disposed within the fluid pump chamber and is configured to apply an outward force to an inner surface of the membrane to increase the volume of the fluid pump chamber.

In a further aspect of the invention, a medical fluid delivery method includes drawing medical fluid into a fluid pump chamber defined between a membrane and a rigid base of a medical fluid cassette by applying an outward force to an inner surface of a portion of the membrane overlying the fluid pump chamber.

In an additional aspect of the invention, a medical fluid pumping system includes a medical fluid pumping machine defining a cassette enclosure and a medical fluid cassette configured to be disposed within the cassette enclosure of the medical fluid pumping machine. The medical fluid pumping machine includes a movable piston. The medical fluid cassette includes a base defining a recess and a member disposed within the recess of the base. The member and the base define a fluid pump chamber therebetween. The cassette is positionable within the cassette enclosure of the medical fluid pumping machine so that the member can be compressed by advancing the piston to force fluid out of the fluid pump chamber, and the member is configured to self-expand as the piston is retracted away from the member to draw fluid into the fluid pump chamber.

In a further aspect of the invention, a medical fluid cassette includes a base defining a recess and a member disposed within the recess of the base. The member and the base define a fluid pump chamber therebetween, and the member is self-expandable, such that after the member has been compressed to force fluid out of the fluid pump chamber, the member can self-expand to draw fluid into the fluid pump chamber.

In another aspect of the invention, a medical fluid delivery method includes drawing medical fluid into a fluid pump chamber defined between a self-expandable member and a rigid base of a medical fluid cassette by applying a compressive force to the self-expandable member and then allowing the self-expandable member to self-expand.

Implementations can include one or more of the following features.

In some implementations, the region of the base that together with the membrane defines the fluid pump chamber is a recessed region of the base.

In some implementations, the membrane together with the base further defines a flow pathway that leads from the fluid pump chamber to an inlet of the cassette and a flow pathway that leads from the fluid pump chamber to an outlet of the cassette.

In some implementations, the member is attached to the base of the cassette.

In some implementations, the member includes a first portion defining a recess configured to receive the piston head.

In some implementations, the member further includes a second portion attached to the first portion, and the second portion is moveable between an expanded position and a compressed position.

In some implementations, the first and second portions are integrally formed with one another.

In some implementations, the second portion is more flexible than the first portion.

In some implementations, the second portion is substantially cup-shaped in the expanded position and substantially planar in the compressed position.

In some implementations, the member includes a first portion and a second resilient portion attached to the first portion. The second resilient portion is configured to resiliently move between an expanded position and a compressed position, and the first portion is configured to apply the outward force to the membrane when the second resilient portion is moved from the compressed position to the expanded position.

In some implementations, the second resilient portion is substantially cup-shaped in the expanded position and substantially planar in the compressed position.

In some implementations, the second resilient portion is a cup-shaped member having a sidewall that defines multiple circumferentially spaced apertures.

In some implementations, the first portion defines a recess configured to receive the piston head.

In some implementations, the medical fluid pumping system further includes a resilient device positioned between the base of the cassette and the member disposed in the fluid pump chamber of the cassette. The resilient device is configured to apply a force to the member.

In some implementations, the resilient device is configured to self-expand after being compressed.

In some implementations, the resilient device includes a spring and/or an elastomeric member.

In some implementations, the medical fluid pumping machine includes a device configured to apply a force to the member disposed in the fluid pump chamber when the cassette is disposed in the cassette enclosure.

In some implementations, the device is a resilient device configured to self-expand after being compressed.

In some implementations, the device includes a spring and/or a spring-loaded piston.

In some implementations, the member has a stem portion disposed within an aperture of the base of the cassette.

In some implementations, the device contacts the stem portion when the cassette is disposed in the cassette enclosure.

In some implementations, the medical fluid pumping system further includes an o-ring surrounding the stem portion, and the o-ring is compressed between the stem portion and a portion of the base defining the aperture in which the stem portion is disposed.

In some implementations, the cassette further includes a seal secured to the base and disposed over the aperture defined by the base.

In some implementations, the device contacts the seal when the cassette is disposed in the cassette enclosure, and the seal is deformable such that a force can be transmitted from the device to the stem portion of the member via the seal.

In some implementations, the seal is configured to prevent fluid from exiting the cassette via the aperture when the force is transmitted to the stem portion.

In some implementations, the member is configured to create a vacuum pressure of about 150 mbar to about 200 mbar within the fluid pump chamber by applying an outward force to the membrane.

In some implementations, the member is configured to apply an outward force of at most about 250 N (e.g., about 20N to about 100N, about 55N) to the membrane.

In some implementations, the medical fluid pumping machine includes first and second movable piston heads, and the membrane and regions of the base cooperate to define first and second fluid pump chambers. The cassette is positionable within the cassette enclosure of the medical fluid pumping machine so that the membrane faces the first and second piston heads and the membrane can be moved by the first and second piston heads to decrease volumes of the first and second fluid pump chambers. First and second members are disposed within the first and second fluid pump chambers, respectively, and are configured to apply outward forces to the inner surface of the membrane to increase the volumes of the first and second fluid pump chambers.

In some implementations, the medical fluid pumping machine includes a rod having a first end region and a second end region, and the rod is configured such that the first end region can apply a force to the first member disposed in the first fluid chamber and the second end region can apply a force to the second member disposed in the second fluid chamber.

In some implementations, the rod is pivotable about a central pivot point such that when the first end region applies a force to the first member causing the first member to apply the outward force to the membrane, the second end region moves away from the second member, and when the second end region applies a force to the second member causing the second member to apply the outward force to the membrane, the first end region moves away from the first member.

In some implementations, the rod is configured so that forces can be transmitted to the rod by the first and second piston heads, and the rod is configured such that when the first piston head applies a force to the first end region of the rod, the rod pivots and the second end region of the rod applies a force to the second piston head, and when the second piston head applies a force to the second end region of the rod, the rod pivots and the first end region of the rod applies a force to the first piston head.

In some implementations, the base of the cassette is a molded tray-like base.

In some implementations, the membrane is attached only to a perimeter region of the tray-like base.

In some implementations, the base includes a planar surface and multiple raised features extending from the planar surface, and the multiple raised features contact the inner surface of the membrane when the membrane is pressed against the base.

In some implementations, at least one of the multiple raised features cooperate with the membrane to form the fluid pump chamber when the membrane is pressed against the base.

In some implementations, at least some of the raised features cooperate with the membrane to form fluid pathways in fluid communication with the fluid pump chamber when the membrane is pressed against the base.

In some implementations, the medical fluid pumping system is a dialysis system (e.g., a peritoneal dialysis system).

In some implementations, the medical fluid cassette is disposable.

In some implementations, the membrane and regions of the base cooperate to define first and second fluid pump chambers, and first and second members are disposed within the first and second fluid pump chambers, respectively, and are configured to apply outward forces to the inner surface of the membrane to increase the volumes of the first and second fluid pump chambers.

In some implementations, the medical fluid delivery method further includes expelling the medical fluid from the fluid pump chamber by applying an inward force to an outer surface of the portion of the membrane overlying the fluid pump chamber.

In some implementations, the outward force is applied to the membrane by a member disposed in the fluid pump chamber.

In some implementations, the member is a resilient member configured to self-expand after being compressed.

In some implementations, by applying the outward force to the inner surface of the portion of the membrane overlying the fluid pump chamber, a vacuum pressure of about 150 mbar to about 200 mbar is created within the fluid pump chamber.

In some implementations, an outward force of about 20N to about 100N (e.g., about 55N) is applied to the membrane.

In some implementations, the medical fluid is a dialysis solution.

In some implementations, the member disposed within the fluid pump chamber is a substantially planar spring.

In some implementations, the substantially planar spring is disposed in a region of the fluid pump chamber directly adjacent the membrane.

In some implementations, the substantially planar spring includes a hub portion and a plurality of circumferentially spaced legs extending radially outward from the hub portion.

In some implementations, the substantially planar spring further includes feet extending from ends of the legs opposite the hub portion, and at least one of the feet has a width that is greater than a width of the leg to which the at least one of the feet is attached.

In some implementations, the at least one of the feet has a curved configuration that substantially conforms to an adjacent surface of the base.

In some implementations, the substantially planar spring is formed of one or more metals.

In some implementations, the member disposed within the pump chamber includes a spring having an annular ring and a plurality of circumferentially spaced legs extending radially inward from the annular ring.

In some implementations, the annular ring defines a central aperture configured to receive a piston head therein.

In some implementations, the medical fluid pumping system further includes a membrane attached to the base.

In some implementations, a portion of the membrane covers the recess of the base such that the portion of the membrane is positioned between the piston and the member.

In some implementations, the membrane defines an aperture aligned with the recess of the base such that the when the cassette is positioned within the cassette enclosure of the medical fluid pumping machine and the piston is advanced, the piston directly contacts the member.

In some implementations, the member is a substantially-dome shaped member.

In some implementations, the substantially dome-shaped member has a surface that is contacted by the piston when the cassette is positioned within the cassette enclosure of the medical fluid pumping machine and the piston is advanced, and the surface is substantially flat.

In some implementations, the recess is substantially cylindrical.

In some implementations, the member is formed of a resilient polymeric material.

In some implementations, the member is formed of polyurethane.

In some implementations, the member is secured to the base in a liquid-tight manner.

In some implementations, the member includes a flange that is compressed against a surface of the base defining the recess to create the liquid-tight seal.

In some implementations, the base defines a fluid passage that extends to a port defined in a surface of the base adjacent the fluid pump chamber such that fluid can pass through the fluid passage and the port into the fluid pump chamber.

In some implementations, the passage extends substantially parallel to a longitudinal axis of the recess.

In some implementations, a portion of the base underlying the member defines a channel that is in fluid communication with the port.

In some implementations, wherein the member is configured to create a vacuum pressure of about 150 mbar to about 200 mbar within the fluid pump chamber as the member self-expands.

In some implementations, applying the compressive force to the self-expandable member causes medical fluid to be expelled from the fluid pump chamber.

In some implementations, applying the compressive force to the self-expandable member includes applying an inward force to an outer surface of a portion of a membrane overlying the member.

In some implementations, the expansion of the self-expandable member generates a vacuum pressure of about 150 mbar to about 200 mbar within the fluid pump chamber.

Implementations can include one or more of the following advantages.

In some implementations, a member disposed in the fluid pump chamber of the cassette is configured to apply an outward force to the inner surface of the membrane in order to increase the volume of the fluid pump chamber and draw medical fluid into the fluid pump chamber. Because the force applied to the membrane to increase the volume of the fluid pump chamber is a pushing force applied by the member disposed in the fluid pump chamber, rather than a pulling force applied by the piston head that acts on the outer surface of the membrane, the vacuum pressure used to draw the fluid into the pump chamber can be controlled independent of the piston head movement. This can help to maintain the vacuum pressure within a desired range in the event that an obstruction or blockage occurs in a delivery line that is fluidly connected to the fluid pump chamber. For example, if an obstruction or blockage occurs in the patient line leading to the cassette and causes the fluid flow rate into the fluid pump chamber to decrease, the retracting piston head will separate from the membrane and the member disposed in the fluid pump chamber will dictate the rate at which the membrane is forced away from the base of the cassette to increase the volume of the fluid pump chamber and draw fluid into the fluid pump chamber. This can help to prevent the vacuum pressure applied to the patient from exceeding a desired limit.

In certain implementations, the member used to apply the outward force to the membrane is a self-expanding mechanism that is part of the cassette itself. This can reduce the complexity of the overall system. For example, unlike certain prior systems, this arrangement does not require an external force, such as vacuum pressure, to be applied to the portion of the membrane overlying the fluid pump chamber in order to draw fluid into the fluid chamber. Nor does this arrangement require the user to take active steps to otherwise attach a piston head to the portion of the membrane overlying the pump chamber. Due to the relatively straightforward set up and operation of the systems described herein, the systems described herein are more user friendly than certain prior systems.

In some implementations, the member used to apply the outward force to the membrane is actuated by a moveable member (e.g., a piston) extending from the medical fluid pumping machine (e.g., extending from a door of the medical fluid pumping machine). In such implementations, the design of the cassette can be simplified, and thus the cassette can be produced relatively inexpensively. In addition, in certain implementations, the moveable member of the medical fluid pumping machine is adjustable such that the force applied to the membrane of the cassette can be adjusted as desired. As a result, a single cassette can be used for different applications that require different magnitudes of force to be applied to the membrane.

Other aspects, features, and advantages will be apparent from the description and drawings, and from the claims.

DESCRIPTION OF DRAWINGS

FIG. 6 is a plan view of the PD cassette of FIG. 4, from the flexible membrane side of the PD cassette.

FIG. 7 is a side view of the PD cassette of FIG. 4.

FIGS. 12A-12C are diagrammatic cross-sectional views of the PD cassette in the cassette compartment of the PD cycler of the PD system of FIG. 1, during different phases of operation.

FIGS. 16A and 16B are diagrammatic cross-sectional views of the PD cassette of FIG. 14 in the cassette compartment of the PD cycler illustrated in FIG. 1, during different phases of operation.

FIG. 26 is a top, diagrammatical, cross-sectional view of the PD cassette of FIG. 22 in the cassette compartment of a PD cycler that includes a pivotable rod that can be used to alternately displace cup-shaped members in pump chambers of the PD cassette.

DETAILED DESCRIPTION

In certain aspects of the invention, a medical fluid cassette (e.g., a dialysis fluid cassette) includes a member disposed in a chamber formed between a membrane and a base of the cassette. During use, a piston of a medical fluid pumping machine (e.g., a dialysis machine) applies an inward force to the membrane and the member, forcing fluid out of the chamber. The piston is subsequently retracted, and, as the piston is retracted, the member disposed in the chamber applies an outward force to the membrane, causing fluid to be drawn into the chamber. Examples of medical fluid cassettes and medical fluid pumping machines are described below.

Figure 1:
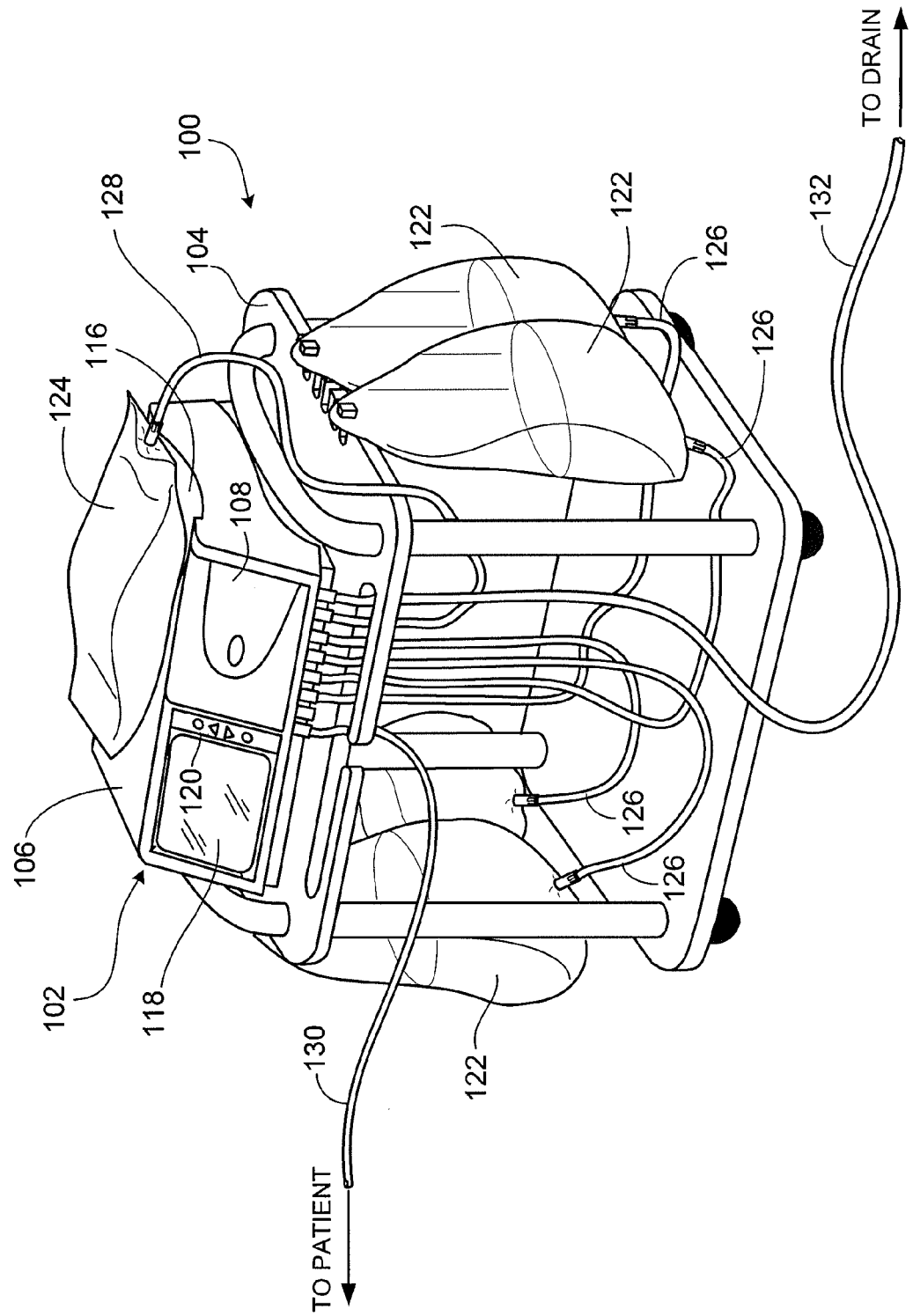
FIG. 1 is a perspective view of a peritoneal dialysis ("PD") system that includes a PD cycler positioned atop a portable cart.
Figure 2:
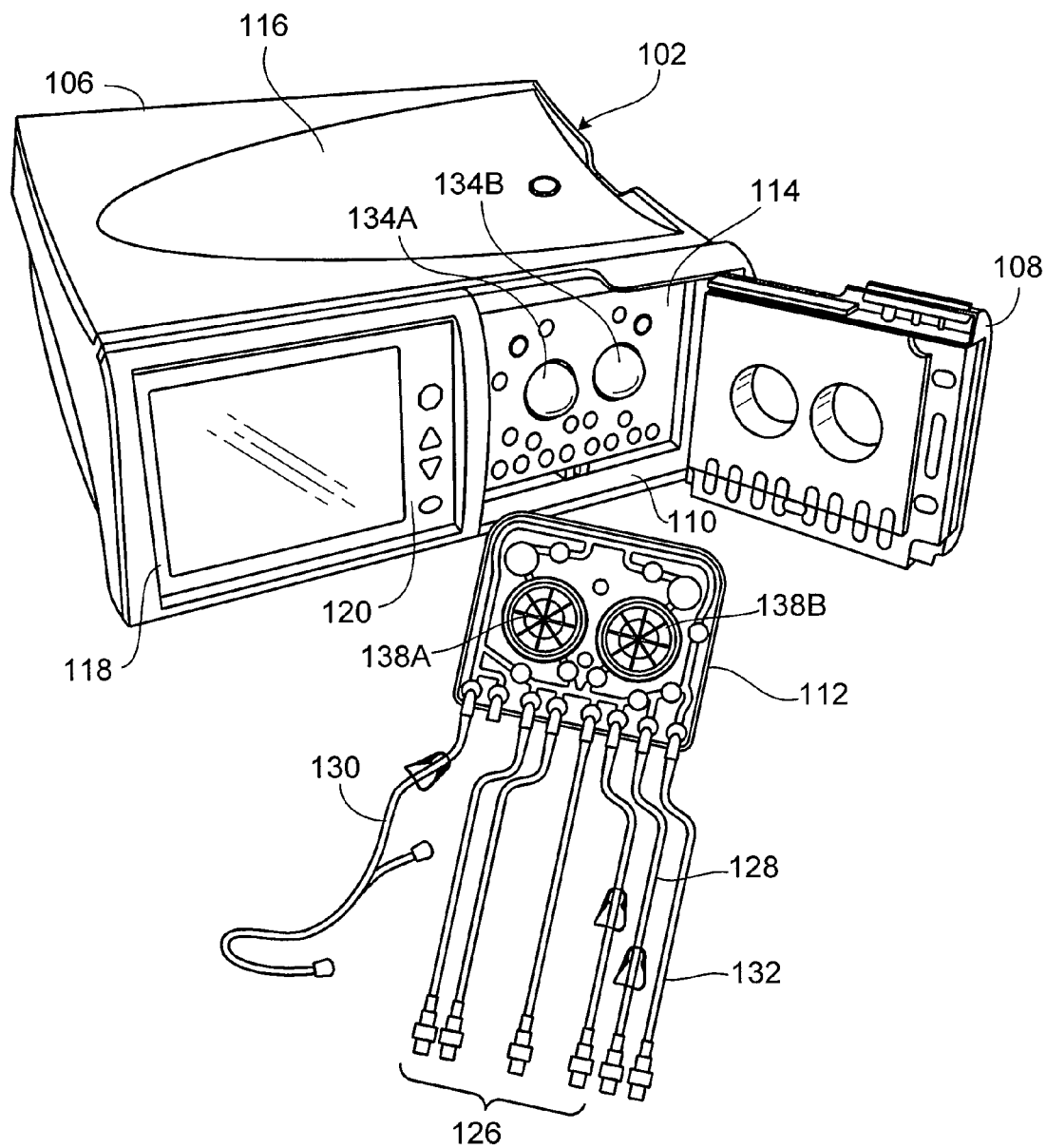
FIG. 2 is a perspective view of the PD cycler and PD cassette of the PD system of FIG. 1. A door of the PD cycler is in the open position to show the inner surfaces of the PD cycler that interface with the PD cassette during use.

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that mates with a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a 5 liter bag of dialysis solution). The PD cycler 102 also includes a touch screen 118 and additional control buttons 120 that can be operated by a user (e.g., a patient) to allow, for example, set-up, initiation, and/or termination of a PD treatment.

Dialysis solution bags 122 are suspended from fingers on the sides of the cart 104, and a heater bag 124 is positioned on the heater tray 116. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Figure 3:
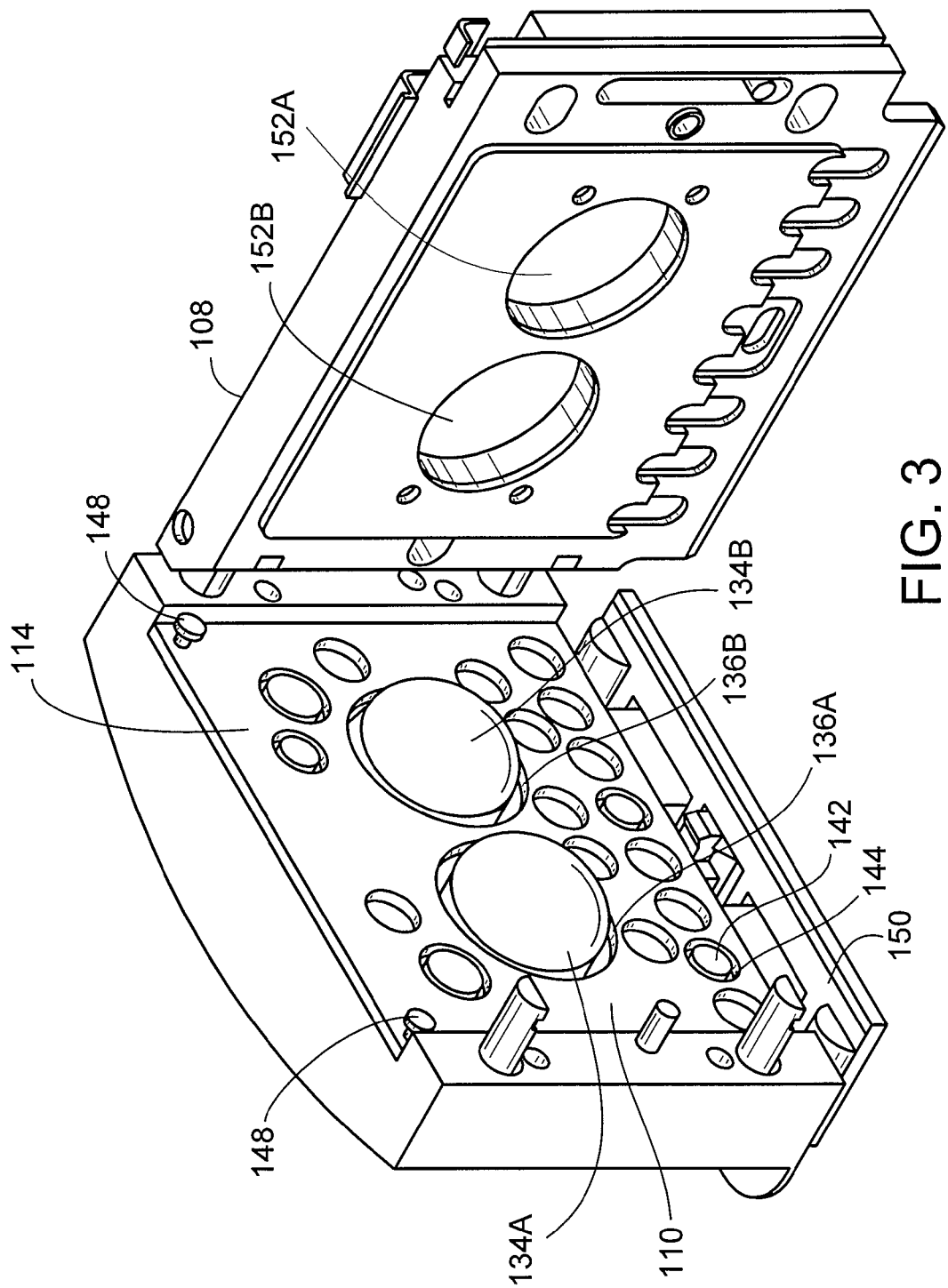
FIG. 3 is a perspective view of an open cassette compartment of the PD cycler of FIGS. 1 and 2.

FIG. 3 shows a more detailed view of the cassette interface 110 and the door 108 of the PD cycler 102. As shown, the PD cycler 102 includes pistons with substantially hemispherical piston heads 134A, 134B that can be axially moved within piston access ports 136A, 136B formed in the cassette interface 110. The piston heads 134A, 134B can be formed of any of various different polymers, metals, and/or alloys. In some implementations, the piston heads 134A, 134B are made of polyoxymethylene (marketed under the trade name Delrin available from Dupont of Wilmington, Del.). The hemispherical shape of the piston heads 134A, 134B can be achieved using any of various different techniques, including machining techniques molding techniques, and/or casting techniques.

The pistons include piston shafts (shown in FIGS. 12A-12C) that are coupled to motors that can be operated to move the piston heads 134A, 134B axially inward and outward within the piston access ports 136A, 136B. As discussed below, when the cassette 112 (shown in FIGS. 2 and 4-8) is positioned within the cassette compartment 114 with the door 108 closed, the piston heads 134A, 134B of the PD cycler 102 align with pump chambers 138A, 138B of the cassette 112. As a result, the piston heads 134A, 134B can be moved in the direction of the cassette 112 to force the membrane 140 into the volume defined by the pump chambers 138A, 138B, causing the volume defined by the pump chambers 138A, 138B to decrease and forcing dialysis solution out of the pump chambers 138A, 138B. The piston heads 134A, 134B can also be retracted away from the cassette 112 and out of the volume defined by the pump chambers 138A, 138B. As discussed in greater detail below, resilient spring members 161A, 161B are disposed in the pump chambers 138A, 138B and are arranged to expand and push the portions of the membrane 140 overlying the pump chambers 138A, 138B toward the piston heads 134A, 134B as the piston heads 134A, 134B are retracted. As a result, the volume defined by the pump chambers 138A, 138B increases and dialysis solution is drawn into the pump chambers 138A, 138B as the piston heads 134A, 134B retract and the resilient spring members 161A, 161B expand.

Referring again to FIG. 3, the PD cycler 102 also includes multiple inflatable members 142 positioned within inflatable member access ports 144 in the cassette interface 110. The inflatable members 142 align with depressible dome regions 146 of the cassette 112 when the cassette 112 is positioned within the cassette compartment 114. While only one of the inflatable members 142 is labeled in FIG. 3, it should be understood that the PD cycler 102 includes an inflatable member associated with each of the depressible dome regions 146 of the cassette 112 (shown in FIG. 5). The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member access ports 144 and out of contact with the cassette 112 when deflated. By inflating certain inflatable members 142 to depress their associated dome regions 146 on the cassette 112, certain fluid flow paths within the cassette 112 can be blocked off. Thus, dialysis solution can be pumped through the cassette 112 by actuating the piston heads 134A, 134B, and can be guided along desired flow paths within the cassette 112 by selectively inflating and deflating the inflatable members 142.

Still referring to FIG. 3, locating pins 148 extend from the cassette interface 110. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a lower ledge 150 extending from the cassette interface 110 to allow the door 108 to be closed over the cassette 112. The locating pins 148 help to ensure that the pump chambers 138A, 138B of the cassette 112 are aligned with the piston heads 134A, 134B when the cassette 112 is positioned in the cassette compartment 114 between the closed door 108 and the cassette interface 110.

The door 108, as shown in FIG. 3, defines recesses 152A, 152B that substantially align with the piston heads 134A, 134B when the door 108 is in the closed position. When the cassette 112 is positioned within the cassette compartment 114, hollow projections 154A, 154B of the cassette 112 (shown in FIGS. 7 and 8), inner surfaces of which cooperate with the membrane 140 to form the pump chambers 138A, 138B, fit within the recesses 152A, 152B. The door 108 further includes a pad that can be inflated during use to compress the cassette 112 between the door 108 and the cassette interface 110. With the pad inflated, the portions of the door 108 forming the recesses 152A, 152B support the projections 154A, 154B and the planar surface of the door 108 supports the other regions of the cassette 112. The door 108 can counteract the forces applied by the piston heads 134A, 134B and the inflatable members 142 and thus allows the piston heads 134A, 134B to depress the portions of the membrane 140 overlying the pump chambers 138A, 138B and similarly allows the inflatable members 142 to actuate the depressible dome regions 146 on the cassette 112.

The PD cycler 102 includes various other features not described in detail herein. Further details regarding the PD cycler 102 and its various components can be found in U.S. Patent Application Publication No. 2007/0112297, which is incorporated by reference herein.

Figure 4:
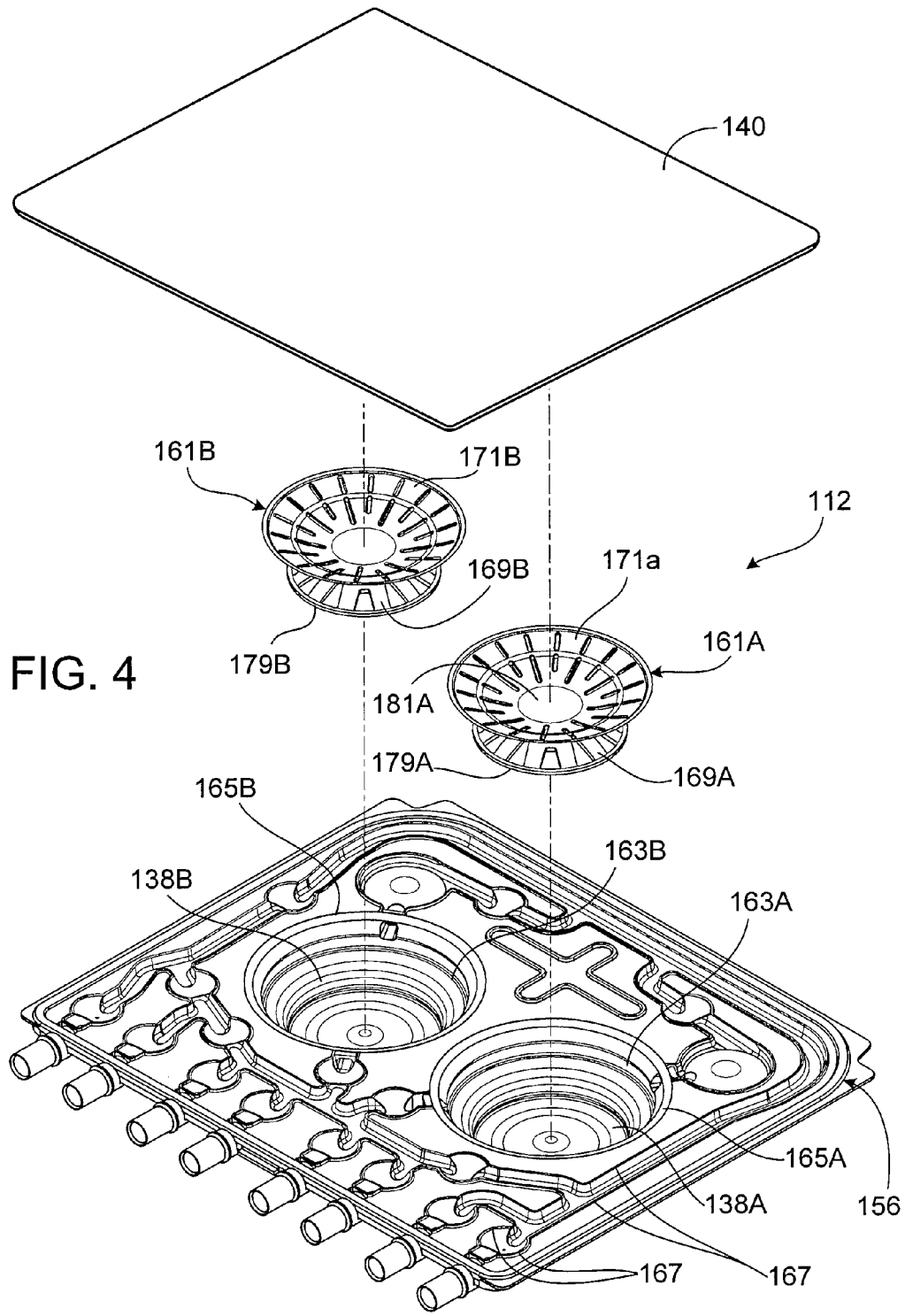
FIG. 4 is an exploded, perspective view of the PD cassette of the PD system of FIG. 1.

FIG. 4 is an exploded, perspective view of the cassette 112. As shown in FIG. 4, the cassette 112 includes a tray-like rigid base 156, the flexible membrane 140, which is attached to the periphery of the base 156 when the cassette 112 is fully assembled, and the spring members 161A, 161B disposed in recessed regions 163A, 163B of the base 156. Raised ridges 165A, 165B extend from a planar surface of the base around each of the recessed regions 163A, 163B and extend towards and into contact with the inner surface of the flexible membrane 140 when the cassette 112 is compressed between the door 108 and the cassette interface 110 of the PD cycler 102. In addition to the raised ridges 165A, 165B surrounding the recessed regions 163A, 163B, a series of raised ridges 167 extend from the planar surface of the base 156 towards and into contact with the inner surface of the flexible membrane 140 when the cassette 112 is compressed between the door 108 and the cassette interface 110 of the PD cycler 102.

Figure 5:
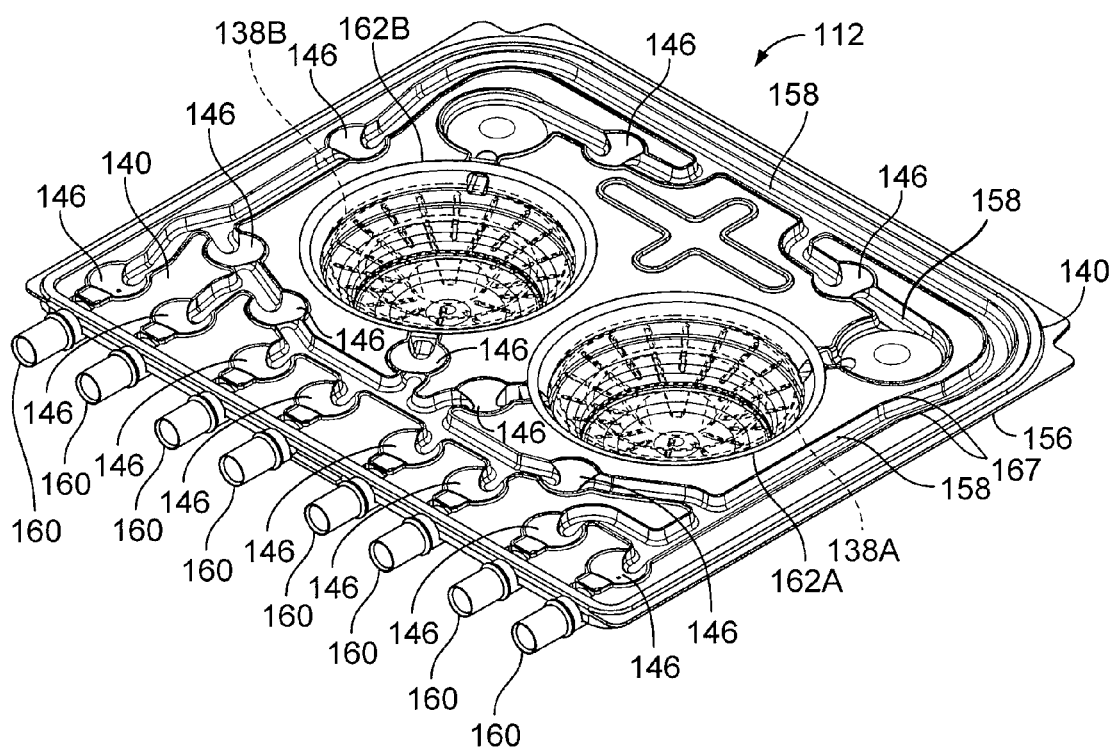
FIG. 5 is a perspective view of the PD cassette of FIG. 4, from a flexible membrane side of the PD cassette.

FIGS. 5 and 6 show planar and perspective views, respectively, of the assembled cassette 112. Referring to FIGS. 4-6, the recessed regions 163A, 163B of the base 156 cooperate with the flexible membrane 140 to form the pump chambers 138A, 138B when the cassette 112 is compressed between the door 108 and the cassette interface 110 of the PD cycler 102 resulting in the flexible membrane 140 being pressed against the raised ridges 165A, 165B of the base 156. In particular, the volumes between the membrane 140 and the hollow projections 154A, 154B (shown in FIGS. 7 and 8) that form the recessed regions 163A, 163B of the base 156 serve as the pump chambers 138A, 138B. The membrane 140, when compressed against the base 156, similarly cooperates with the series of raised ridges 167 extending from the base 156 to form a series of fluid pathways 158 and to form the multiple, depressible dome regions 146, which are widened portions (e.g., substantially circular widened portions) of the fluid pathways 158. During use, the dialysis solution flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysis solution along the region of the pathway 158 associated with that dome region 146 during use. Thus, as described in further detail below, the flow of dialysis solution through the cassette 112 can be controlled through the selective depression of the depressible dome regions 146 by selectively inflating the inflatable members 142 of the PD cycler 102.

Figure 8:
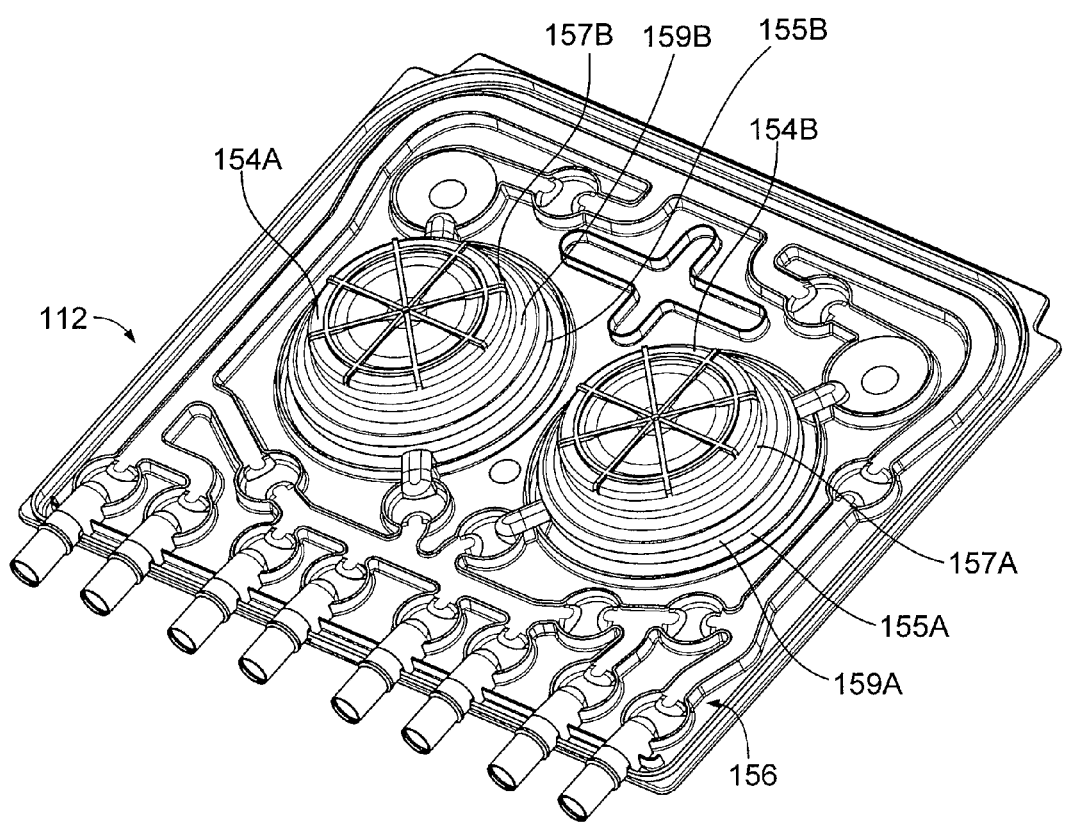
FIG. 8 is a perspective view of the PD cassette of FIG. 4, from a rigid base side of the PD cassette.

Referring to FIGS. 7 and 8, which show a side view of the cassette 112 and a top view of the cassette 112 from the side of the base 156, respectively, the recessed regions 163A, 163B (shown in FIG. 4) of the base 156 are formed by the hollow projections 154A, 154B, which extend away from the flexible membrane 140. The hollow projections 154A, 154B are substantially symmetrically positioned with respect to the center vertical axis of the cassette 112. The projections 154A, 154B are sized and shaped to fit within the recesses 152A, 152B in the door 108 of the PD cycler 102. The hollow projections 154A, 154B include first cylindrical regions 155A, 155B and second smaller-diameter cylindrical regions 157A, 157B positioned below the first cylindrical regions 155A, 155B. The first cylindrical regions 155A, 155B and second cylindrical regions 157A, 157B of the projections 157A, 157B are connected by tapered regions 159A, 159B.

The inner surface of each cylindrical region 157A, 157B of the hollow projections 154A, 154B forms an annular channel around its perimeter. Each of the annular channels is configured to receive a corresponding structure of its associated spring member 161A, 161B to retain the spring member 161A, 161B in a fixed position within the pump chambers 138A, 138B.

The rigidity of the base 156 helps to hold the cassette 112 in place within the cassette compartment 114 of the PD cycler 102 and to prevent the base 156 from flexing and deforming in response to forces applied to the projections 154A, 154B by the piston heads 134A, 134B and in response to forces applied to the planar surface of the base 156 by the inflatable members 142.

The base 156 can be formed of any of various relatively rigid materials. In some implementations, the base 156 is formed of one or more polymers, such as polypropylene, polyvinyl chloride, polycarbonate, polysulfone, and other medical grade plastic materials. In certain implementations, the base 156 is formed of one or more metals or alloys, such as stainless steel. The base 156 can alternatively be formed of various different combinations of the above-noted polymers and metals. The base 156 can be formed using any of various different techniques, including machining, molding, and casting techniques.

Referring again to FIGS. 5 and 6, fluid line connectors 160 are positioned along the bottom edge of the cassette 112. The fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette, as shown in FIGS. 1 and 2, the connectors 160 allow dialysis solution to flow into and out of the cassette 112 during use.

Figure 9:
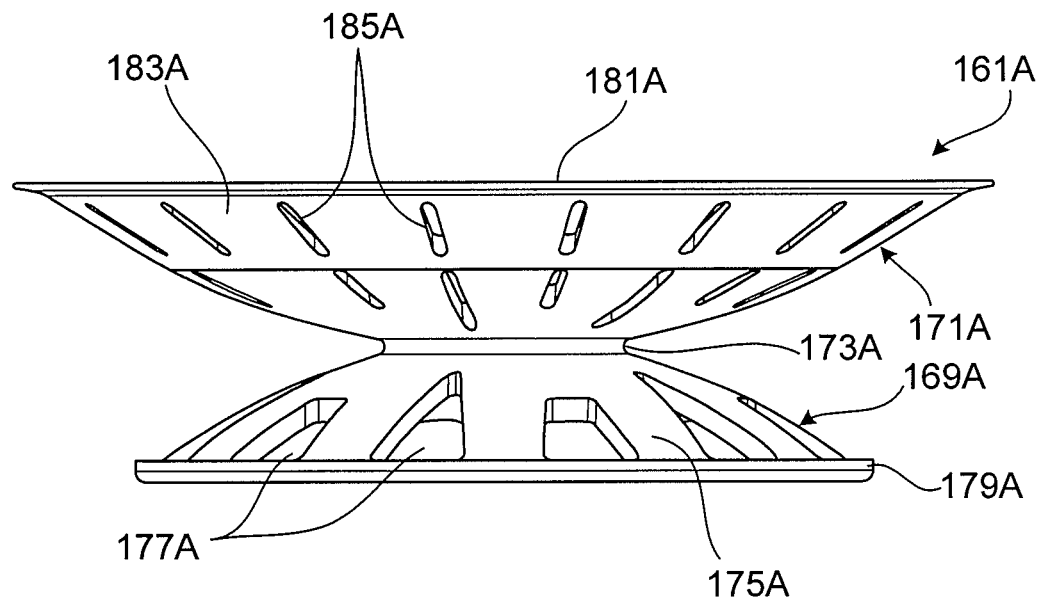
FIG. 9 is a side view of a spring member of the PD cassette of FIG. 4 in an expanded configuration.
Figure 10:
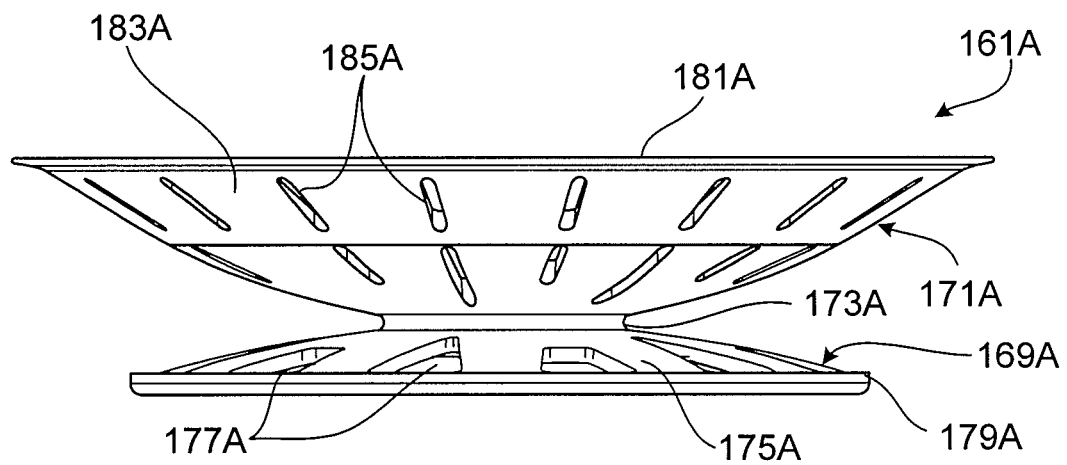
FIG. 10 is a side view of a spring member of the PD cassette of FIG. 4 in a compressed configuration.

FIG. 9 is a side view of the spring member 161A in an expanded position, and FIG. 10 is a side view of the spring member 161A in a compressed position. It should be understood that the other spring member 161B of the cassette 112 is structurally and functionally identical to the spring member 161A. Referring to FIGS. 4, 9, and 10, the spring member 161A includes a resilient cup-shaped portion 169A that is integrally connected to a more rigid cup-shaped portion 171A by a connecting region 173A. The resilient cup-shaped portion 169A includes a side wall 175A with multiple apertures 177A around its circumference. The apertures 177A are sized and shaped to enable the resilient cup-shaped portion 169A to be compressed from its expanded cup-shaped position (shown in FIG. 9) to a flatter compressed configuration (shown in FIG. 10) and to resiliently return to the expanded cup-shaped configuration when the compressing force is released.

An annular lip 179A extends radially outward from the rim of the resilient cup-shaped portion 169A. The annular lip 179A is sized and shaped to snap into the annular recess formed by the inner surface of the hollow projection 154A of the base 156. The spring member 161A can thus be secured to the base 156 by pressing the spring member 161A toward the base 156 until the annular lip 179A snaps into the annular recess of the hollow projection 154A. Any of various other attachment techniques, such as adhesive bonding, thermal bonding, mechanical fastening, etc., can alternatively or additionally be used to attach the spring member to the base.

As shown in FIG. 9, some of the apertures 177A in the side wall 175A of the resilient cup-shaped portion 169A are triangular apertures that are spaced apart around the circumference of resilient cup-shaped portion 169A. The other apertures 177A are trapezoidal apertures that are positioned between the triangular apertures. The apertures 177A permit the portions of the side wall 175A between adjacent apertures to expand into the space defined by the apertures when the resilient cup-shaped portion 169A is compressed, as shown in FIG. 10. Thus, the apertures 177A allow the resilient cup-shaped portion 169A to be compressed to a flatter configuration without increasing the diameter of the resilient cup-shaped portion 169A. This arrangement helps to prevent sliding contact between the resilient cup-shaped portion 169A and the hollow projection 154A of the base 156 during use, and thus helps to prevent particulate from rubbing off the resilient cup-shaped portion 169A and the hollow projection 154A and collecting in the dialysis solution within the pump chamber 138A.

The material and shape of the resilient cup-shaped portion 169A can be selected to provide the resilient cup-shaped portion 169A with a desired resiliency. In certain implementations, the resilient cup-shaped portion 169A is configured to cause the rigid cup-shaped portion 171A to apply an outward force of about 20N to about 250N (e.g., about 20N to about 100N, about 55N). As discussed in greater detail below, applying such a force to the inner surface of the membrane 140 can create a vacuum pressure of about 150 mbar to about 200 mbar (e.g., about 150 mbar) within the pump chamber 138A and within fluid lines that are fluidly connected to the pump chamber. However, the resilient cup-shaped portion 169A can be formed in a way to apply higher or lower forces to the membrane 140, depending on the intended use or application of the spring member 161A.

Still referring to FIGS. 9 and 10, the more rigid cup-shaped portion 171A includes a recess 181A sized and shaped to receive the hemispherical piston head 134A of the dialysis machine therein. This configuration can help to ensure that the piston head 134A is properly aligned with the spring member 161A during use. The sidewall 183A of the cup-shaped portion 171A includes elongate slots 185A spaced around its circumference. The slots 185A allow fluid to pass from one side of the cup-shaped portion 171A to the other side of the cup-shaped portion 171A. As an alternative to or in addition to slots, any of various other sized and shaped apertures that permit fluid transfer from one side of the rigid cup-shaped portion 171A to the other side of the rigid cup-shaped portion 171A can be used.

The cup-shaped portions 169A, 171A of the spring member 161A can be formed of any of various materials that provide the spring member 161A with a desired resiliency. In some implementations, the cup-shaped portions 169A, 171A and the connector region 173A are formed of the same material(s). Alternatively, each of the cup-shaped portions 169A, 171A and the connector region 173A can be formed of different materials. Examples of materials from which the spring member 161A can be formed include polymers, such as acetal, polysulfone, polycarbonate, nylon, elastomeric polyester, and polyurethane, and/or metals, such as stainless steel.

Any of various techniques can be used to form the spring member 161B. In certain implementations, the spring member 161A is formed using an injection molding technique. In some implementations, for example, the spring member 161A is formed using a two-part mold. A first mold part is used to form the resilient cup-shaped portion 169A and a second mold part is used to form the rigid cup-shaped portion 171A. When forming the spring member 161A, the first and second mold parts are positioned adjacent one another and a mold insert is positioned between the two mold parts. The mold insert is used to form the connector region 173A between the two cup-shaped portions 169A, 171A. The mold insert typically includes two halves that slide together to form the connector region 173A. After molding the spring member 161A, the two mold parts are moved away from one another and the two halves of the mold insert are moved away from one another to allow the molded spring member 161A to be removed from the molding apparatus. As an alternative to or in addition to injection molding, other techniques, such as machining techniques, can be used to form the spring member 161A.

As noted above, the membrane 140 is attached to the periphery of the base 156. The portion of the membrane 140 overlying the central portion of the base 156 is typically not attached to the base 156. Rather, this portion of the membrane 140 sits loosely atop the raised ridges 165A, 165B, and 167 extending from the planar surface of the base 156. Any of various attachment techniques, such as adhesive bonding and thermal bonding, can be used to attach the membrane 140 to the periphery of the base 156. The thickness and material(s) of the membrane 140 are selected so that the membrane 140 has sufficient flexibility to flex toward the base 156 in response to the force applied to the membrane 140 by the piston heads 134A, 134B and the inflatable members 142. In certain implementations, the membrane 140 is about 0.100 micron to about 0.150 micron in thickness. However, various other thicknesses may be sufficient depending on the type of material used to form the membrane 140.

Any of various different materials that permit the membrane 140 to deflect in response to movement of the piston heads 134A, 134B and inflation of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

The rigid base 156, the membrane 140, and the spring members 161A, 161B are typically formed separately and then assembled to make the cassette 112. In some implementations, for example, after forming the rigid base 156 and the spring members 161A, 161B, the spring members 161A, 161B are inserted into the recesses 163A, 163B fanned by the hollow protrusions 154A, 154B of the rigid base 156. The annular lips 179A, 179B of the resilient cup-shaped portions 169A, 169B of the spring members 161A, 161B are then snapped into the annular recesses formed by the inner surfaces of the hollow projections 154A, 154B to secure the spring members 161A, 161B to the base 156. The membrane 140 is then attached to the perimeter of the rigid base 156.

Other manufacturing techniques can alternatively be used to make the cassette 112. As mentioned above, for example, other techniques can be used to secure the spring members 161A, 161B to the base 156. In addition, as an alternative to attaching the spring members 161A, 161B to the base 156, it is possible to integrally form the spring members 161A, 161B along with the base 156. In certain embodiments, for example, the base 156 and the spring members 161A, 161B can be machined from a single piece of material.

Figure 11:
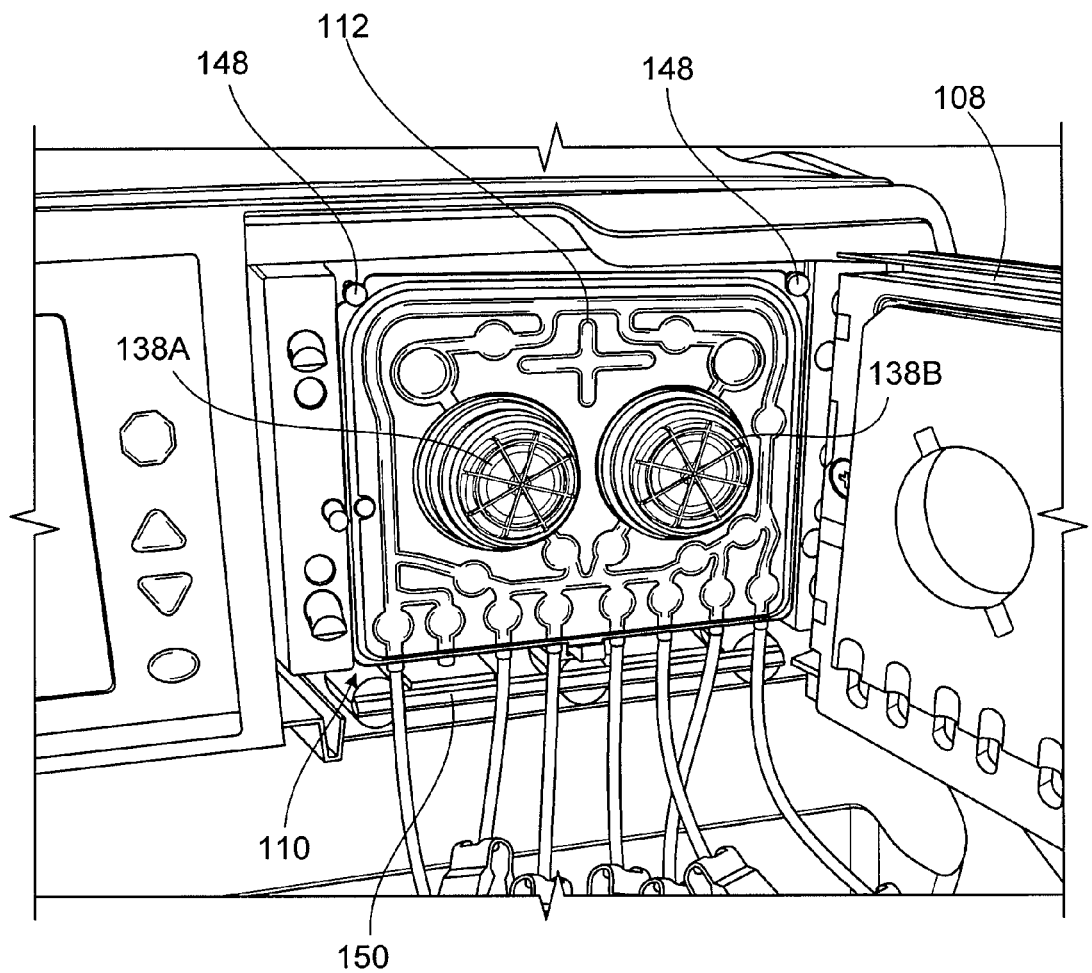
FIG. 11 is a partial perspective view of the PD cassette in the cassette compartment of the PD cycler of the PD system of FIG. 1.

As shown in FIG. 11, before treatment, the door 108 of the PD cycler 102 is opened to expose the cassette interface 110, and the cassette 112 is positioned with its membrane 140 adjacent to the interface 110. The cassette 112 is positioned such that the pump chambers 138A, 138B of the cassette 112 are aligned with the piston heads 134A, 134B. In order to ensure that the pump chambers 138A, 138B align with the piston heads 134A, 134B, the cassette 112 is positioned between the locating pins 148 and the lower ledge 150 extending from the cassette interface 110. The asymmetrical positioning of the connectors 160 of the cassette act as a keying feature that reduces the likelihood that the cassette 112 will be installed with the membrane 140 facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108.

While loading the cassette 112 into the PD cycler 102, the piston heads 134A, 134B are typically retracted within the piston access ports 136A, 136B. This positioning of the piston heads 134A, 134B can reduce the likelihood of damage to the piston heads 134A, 134B during installation of the cassette 112.

FIGS. 12A-12B illustrate the pump chamber 138A and its associated spring member 161A and piston head 134A throughout different phases of operation. It should be understood that the other spring member 161B and piston head 134B would operate in a similar manner to pump dialysis solution to and from the other pump chamber 138B.

Referring to FIG. 12A, with the cassette 112 positioned adjacent to the cassette interface 110, the door 108 is closed over the cassette 112 such that the cassette 112 is contained within the cassette compartment 114 between the door 108 and the cassette interface 110. With the cassette 112 positioned in the cassette compartment 114, an inflatable pad within the door 108 is inflated to compress the cassette 112 between the door 108 and the cassette interface 110. This compression of the cassette 112 holds the projections 154A, 154B of the cassette 112 in the recesses 152A, 152B of the door 108 and presses the membrane 140 tightly against the raised ridges 165A, 165B, 167 extending from the planar surface of the rigid base 156 to form the enclosed fluid pathways 158, dome regions 146, and pump chambers 138A, 138B (shown in FIGS. 5 and 6).

During operation, with the cassette 112 secured within the compartment 114, the piston heads 134A, 134B are reciprocated to sequentially alter the volume of each of the pump chambers 138A, 138B. Typically, as the piston head 134A is extended, the other piston head 134B is retracted, and vice versa. As a result, dialysis solution is expelled from the pump chamber 138A at the same time that dialysis solution is drawn into the pump chamber 138B, and vice versa.

As shown in FIG. 12B, after positioning the cassette 112 within the cassette compartment 114 and inflating the pad within the door 108, the piston head 134A is extended to deform the membrane into the recess formed by the rigid cup-shaped portion 171A of the spring member 161A. With the piston head 134A in this position, the spring member 161A disposed within the pump chamber 138A remains in an expanded position. In this position, the volume of the pump chamber 138A is at its maximum treatment level and is full of dialysis solution.

Figure 12C:
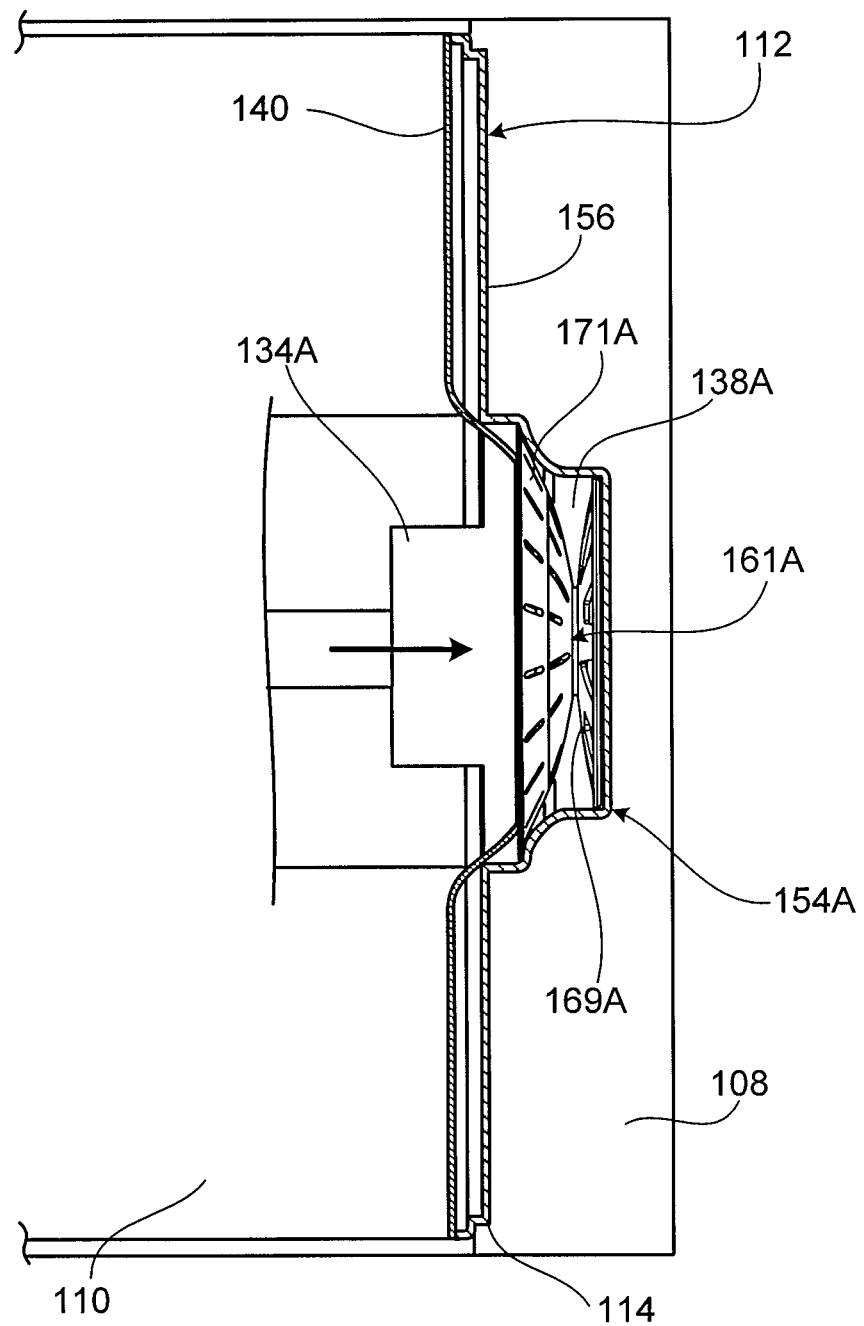

Referring to FIG. 12C, as the piston head 134A is moved outward to a substantially fully extended position, the spring member 161 moves from its expanded position to its compressed position. This decreases the volume of the pump chamber 138A, and thus causes dialysis solution to be expelled from the pump chamber 138A via the fluid pathways 158 of the cassette (shown in FIGS. 5 and 6).

After expelling the dialysis solution from the pump chamber 138A, the piston head 134A is again retracted to the position shown in FIG. 12B. The resiliency of the resilient cup-shaped portion 169A of the spring member 161A causes the resilient cup-shaped portion 169A to apply an outward force to the rigid cup-shaped portion 171A. As a result, the rigid cup-shaped portion 171A applies an outward force to the membrane 140 of the cassette 112. Thus, as the piston head 134A is retracted away from the rigid base 156 of the cassette 112, the rigid cup-shaped portion 171A of the spring member 161A moves the membrane 140 in the same direction as the retracting piston head 134A, thereby increasing the volume of the pump chamber 138A. As the volume of the pump chamber 138A increases, dialysis solution is drawn into the pump chamber 138A of the cassette 112 via the fluid pathways 158 of the cassette 112 (shown in FIGS. 5 and 6).

After drawing the dialysis solution into the pump chamber 138A, the dialysis solution can then be forced out of the pump chamber 138A by again returning the piston head 134A to the position shown in FIG. 12C, causing the membrane 140 to move toward the rigid base 156 and thus decreasing the volume of the pump chambers 138A, 138B. This process is repeated until a desired volume of dialysis solution has been pumped to or from a location (e.g., to or from the patient).

As noted above, while forcing dialysis solution into and out of the pump chambers 138A, 138B, certain inflatable members 142 of the PD cycler 102 can be selectively inflated to direct the pumped dialysis solution along desired pathways in the cassette 112.

Figure 13A:
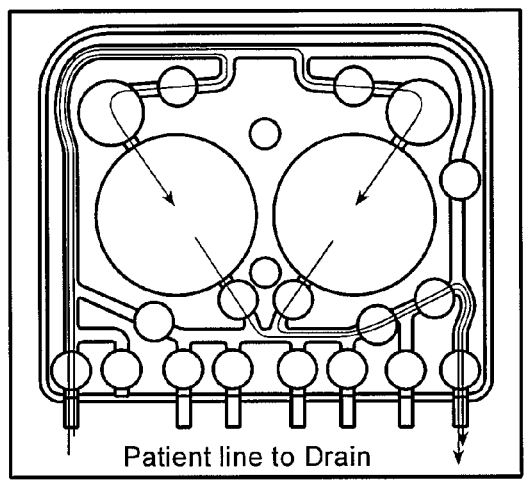
FIGS. 13A-13C illustrate various fluid flow paths through the PD cassette of the PD system of FIG. 1 during a PD treatment.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 102 is activated to cause the piston heads 134A, 134B to reciprocate and selected inflatable members 142 are inflated to cause the spent dialysis solution to be drawn into the pump chambers 138A, 138B of the cassette 112 from the patient and then pumped from the pump chambers 138A, 138B to the drain via the drain line 132. This flow path of the spent dialysis solution through the fluid pathways 158 in the cassette 112 is shown in FIG. 13A.

Figure 13B:
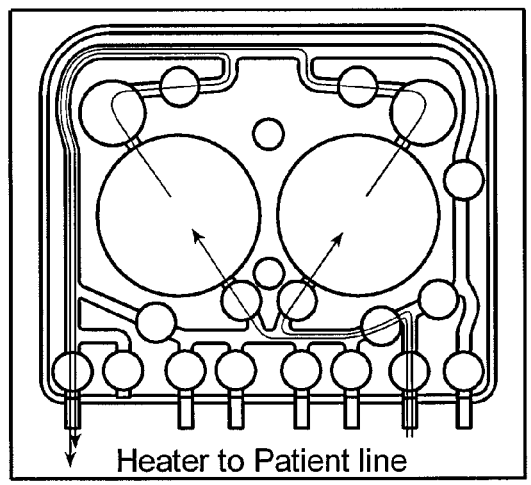

After draining the spent dialysis solution from the patient, heated dialysis solution is transferred from the heater bag 124 to the patient. To do this, the pump of the PD cycler 102 is activated to cause the piston heads 134A, 134B to reciprocate and certain inflatable members 142 of the PD cycler 102 are inflated to cause the spent dialysis solution to be drawn into the pump chambers 138A, 138B of the cassette 112 from the heater bag 124 via the heater bag line 128 and then pumped from the pump chambers 138A, 138B to the patient via the patient line 130. This flow path of the dialysis solution through the fluid pathways 158 in the cassette 112 is shown in FIG. 13B.

Figure 13C:
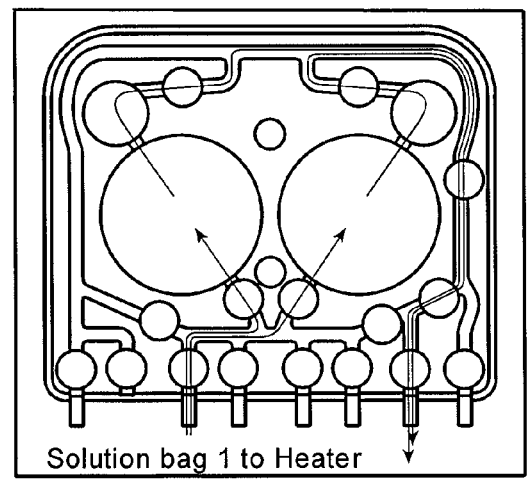

Once the dialysis solution has been pumped from the heater bag 124 to the patient, the dialysis solution is allowed to dwell within the patient for a period of time. During this dwell period, toxins cross the peritoneum into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the pump of the PD cycler 102 is activated to cause the piston heads 134A, 134B to reciprocate and certain inflatable members 142 of the PD cycler 102 are inflated to cause the dialysis solution to be drawn into the pump chambers 138A, 138B of the cassette 112 from the selected dialysis solution bag 122 via its associated line 126 and then pumped from the pump chambers 138A, 138B to the heater bag 124 via the heater bag line 128. This flow path of the dialysis solution through the fluid pathways 158 in the cassette 112 is shown in FIG. 13C.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

While the dialysis solution has been described as being pumped into the heater bag 124 from a single dialysis solution bag 122, dialysis solution can alternatively be pumped into the heater bag 124 from multiple dialysis solution bags 122. Such a technique may be advantageous, for example, where the dialysis solutions in the bags 122 have different concentrations and a desired concentration for treatment is intermediate to the concentrations of the dialysis solution in two or more of the bags 122.

After completion of the PD treatment, the piston heads 134A, 134B are retracted away from the cassette 112 to a sufficient distance such that the piston heads 134A, 134B no longer contact the membrane 140. The door 108 of the PD cycler is then opened and the cassette 112 is removed from the cassette compartment and discarded.

The spring members 161A, 161B of the cassette 112 can help to ensure that the vacuum pressure provided to the fluid pathways 158 of the cassette 112 in order to draw dialysis solution into the pump chambers 138A, 138B is maintained within a desired range. In some implementations, for example, the spring members 161A, 161B are configured to limit the applied vacuum pressure to a range of about 150 mbar to about 200 mbar. This arrangement can be advantageous in the event of an obstruction or blockage in the patient line 130 leading from the patient to the cassette 112. In systems in which the piston head is attached to the membrane, such an obstruction or blockage can result in increased vacuum pressure within the pump chamber and thus increased vacuum pressure applied to the patient because the membrane travels with the piston head despite the diminished flow rate of the dialysis solution into the pump chamber. In contrast, in response to the decreased flow rate of the dialysis solution into the pump chambers 138A, 138B due to an obstruction or blockage, the piston heads 134A, 134B will retract at a greater rate than the membrane 140 and thus release from the membrane 140. The spring members 161A, 161B will continue to apply a force within a desired range (e.g., about 20N to about 250N, about 20N to about 100N, about 55N) to the membrane 140, maintaining the vacuum pressure applied to the patient via the patient line within a desired range (e.g., about 150 mbar to about 200 mbar).

In addition, because the PD system 100 does not require a vacuum system to move the portions 162A, 162B of the membrane 140 overlying the pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective.

While certain implementations have been described, other implementations are possible.

While the side wall 175A of the resilient cup-shaped portion 169A of the spring member 161A has been described as including triangular and trapezoidal apertures 177A, apertures of any of various other shapes and sizes can be used to permit the resilient cup-shaped portion 169A to be compressed into a desired configuration. Further, while the resilient cup-shaped portion 169A has been described as being configured to be compressed into a flattened cup-shape configuration, in some implementations, the resilient cup-shaped portion 169A is configured to take on a substantially planar configuration when compressed. For example, the sizes and shapes of the apertures can be selected to allow the resilient cup-shaped portion 169A to be compressed into a flat planar shape.

While the spring members 161A, 161B have been described as having two opposing cup-shaped members, spring members of any of various other shapes that are capable of applying a desired outward force to the inner surface of the membrane 140 can be used. In certain implementations, for example, one or more leaf springs extend across the fluid pump chamber in a manner to apply an outward force to the inner surface of the membrane 140.

Figure 14:
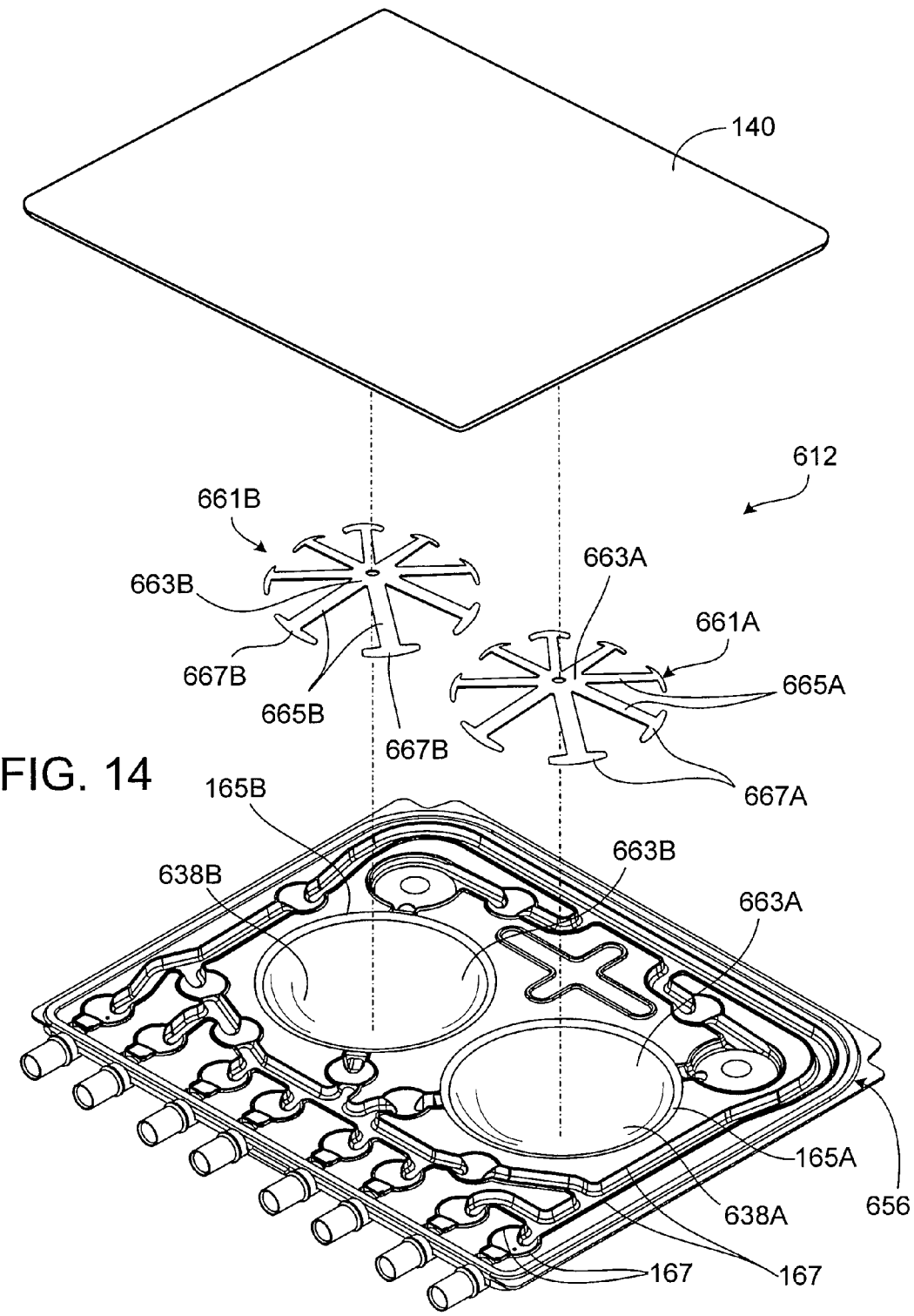
FIG. 14 is an exploded, perspective view of a PD cassette that includes a resilient, substantially flat spring disposed in a pump chamber of the cassette.
Figure 15:
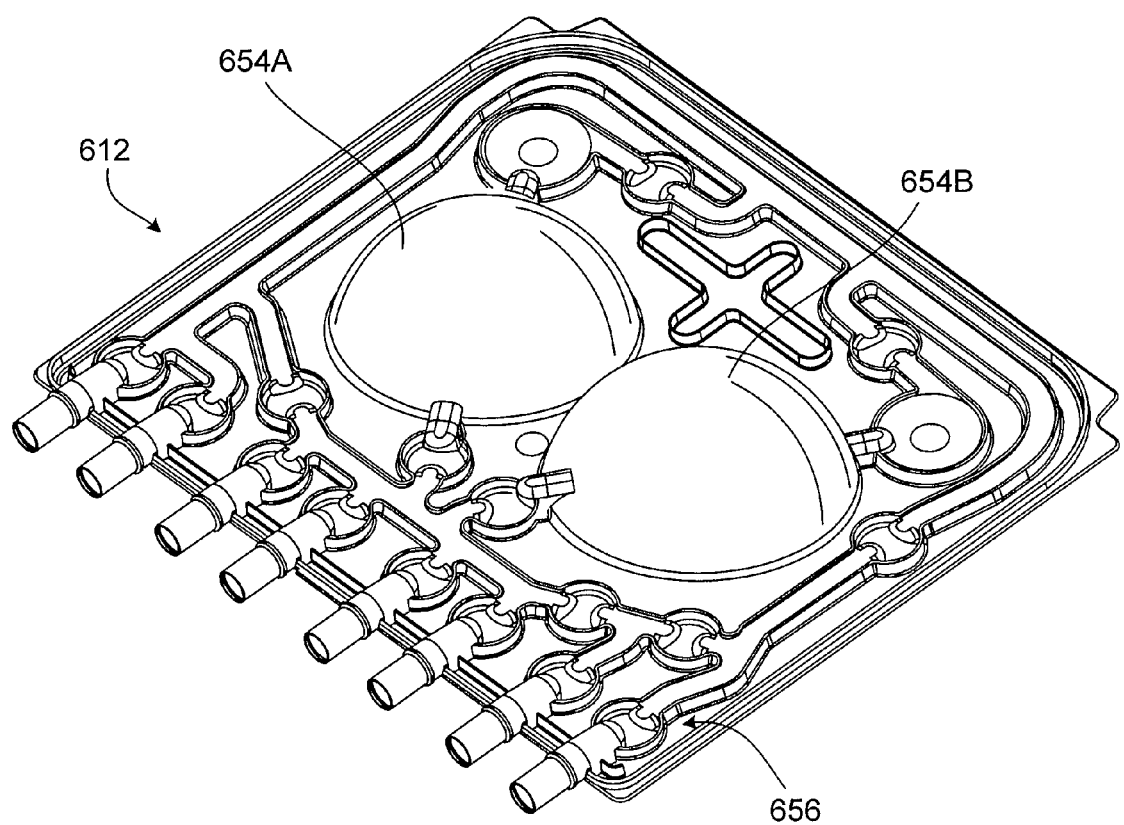
FIG. 15 is a perspective view of the PD cassette of FIG. 14, from a rigid base side of the PD cassette.

FIG. 14 is an exploded view of a PD cassette 612 that includes substantially flat springs 661A, 661B that are disposed in pump chambers 638A, 638B of the cassette 612. As shown in FIGS. 14 and 15, the base 656 of the cassette 612 includes dome-shaped projections 654A, 654B that form hemispherical recessed regions 663A, 663B. The recessed regions 663A, 663B of the base 656 cooperate with the overlying membrane 140 to form the pump chambers 638A, 638B in which the springs 661A, 661B are disposed. The base 656 differs from the base 156 of the cassette 112 in the shape of the recessed regions 663A, 663B. The other structural and functional features of the base 656 are generally the same as the base 156 described above. In addition, the membrane 140 can be secured to the base 656 in the same manner that the membrane 140 was described above as being attached to the base 156 of the cassette 112.

Each of the springs 661A, 661B includes a hub portion 663A, 663B from which multiple, elongate legs 665A, 665B extend. Enlarged pads or feet 667A, 667B are attached to the ends of the legs 665A, 665B. The feet 667A, 667B are circumferentially spaced around the outer edges of the springs 661A, 661B. The hub portion 663A, 663B and the legs 665A, 665B of each of the springs 661A, 661B are substantially flat or planar, while the feet 667A, 667B have a curved configuration. The radius of curvature of the feet 667A, 667B is substantially the same as the radius of curvature of the inner surface of the dome-shaped projections 654A, 654B in which the recessed regions 663A, 663B are formed.

The springs 661A, 661B are constructed with materials and dimensions that provide the springs 661A, 661B with a resiliency that permits the springs 661A, 661B to return to a flat or planar, undeformed position after a force that has been applied to the hub portions 663A, 663B to deflect the springs 661A, 661B into the pump chambers 638A, 638B (i.e., toward the base 656) is released. In some implementations, the springs 661A, 661B are formed of stainless steel (e.g., 302 stainless steel). However, other materials, such as steel, brass, phosphor bronze, polypropylene, polyetherimide (e.g., Ultem®), nylon, steel, brass, and/or phosphor bronze can alternatively or additionally be used to form the springs 661A, 661B. In certain implementations, the springs 661A, 661B are coated with a polymeric coating to increase the biocompatibility of the springs 661A, 661B. The springs 661A, 661B can, for example, be coated with a polytetrafluoroethylene (PTFE) coating.

In certain implementations, the springs 661A, 661B have a thickness of about 0.01 inch to about 0.04 inch. The springs 661A, 661B can have an outer diameter of about 2.0 inches to about 2.5 inches. Each of the legs 665A, 665B can have a length (i.e., the linear distance between the hub portion 663A, 663B and the foot 667A, 667B) of about 0.5 inch to about 1.0 inch and/or a width of about 0.12 inch to about 0.20 inch.

In some implementations, the springs 661A, 661B are formed of 302 stainless steel and have a thickness of about 0.020 inch, and each of the legs 665A, 665B has a length of 0.75 inches and a width of 0.16 inch.

To make each of the springs 661A, 661B, a stamping machine is typically used to stamp from a flat sheet of material a flat member having a shape that generally corresponds to the shape of the springs 661, 661B. The portions of the flat member that correspond to the feet 667A, 667B of the springs 661A, 661B are then formed into a curved shape using a subsequent forming process. Alternatively, the stamping machine can be provided with forming features that permit the springs 661A, 661B to produced in a single stamping/forming step. Any of various other material processing techniques, such as casting, molding, etching, etc. can alternatively or additionally be used to form the springs 661A, 661B.

Still referring to FIG. 14, when the cassette 612 is fully assembled, the springs 661A, 661B are disposed in the recessed regions 663A, 663B of the base 656. The springs 661A, 661B have diameters that are substantially equal to the maximum diameters of the recessed regions 663A, 663B (i.e., equal to the maximum inner diameters of the dome-shaped projections 654A, 654B that form the recessed regions 663A, 663B). As a result of this configuration, the springs 661A, 661B, when in an undeformed position, rest in a top portion of the recessed regions 663A, 663B with the feet 667A, 667B contacting the inner surfaces of the dome-shaped projections 654A, 654B.

The cassette 612 can be used in substantially the same way as the cassette 112 described above. In particular, the cassette 612 can be disposed in the cassette compartment 114 of the PD cycler 102 and the pistons of the PD cycler 102 can be reciprocated to draw fluid into and pump fluid out of the pump chambers 638A, 638B. FIGS. 16A and 16B illustrate the cassette 612 disposed within the cassette compartment 114 of the PD cycler 102 during two different stages of the pumping process. While FIGS. 16A and 16B show the pumping process with respect to the pump chamber 638A, it should be understood that a similar pumping process would occur within the pump chamber 638B of the cassette 612.

As shown in FIG. 16A, as the piston associated with the pump chamber 638A advances forward toward the base 656A of the cassette 612, the spring 661A deforms and roughly conforms to the shape of the piston head 134A. As a result, the volume of the pump chamber 638A decreases, causing fluid to be pumped out of the pump chamber 638A. As the spring 661A is deformed into the recessed region 663A, the feet 667A of the spring 661A apply a force to the inner surface of the dome-shaped projection 654A and then slide along that surface as continued force is applied to the spring 661A. Because the radius of curvature of each of the feet 667A is substantially equal to the radius of curvature of the inner surface of the dome-shaped projection 654A, forces applied to the inner surface of the dome-shaped projection 654A are distributed across the width of each foot 667A and the occurrence of skiving of the inner surface of the dome-shaped projection 654A reduced or prevented.

Referring now to FIG. 16B, as the piston is retracted, the spring 661A returns to its undeformed, flat or planar configuration and applies an outward force to the membrane 140. This increases the volume of pump chamber 638 and thus creates a vacuum within the pump chamber 638, which causes fluid to be drawn into the pump chamber 638.

By reciprocating the pistons associated with the pump chambers 638A, 638B, fluid can be sequentially drawn into and forced out of the pumps chambers 638A, 638B in the manner described above.

The cassette 612 can be assembled in a manner similar to the cassette 112 described above. Typically, after making the base 656 and the springs 661A, 661B, the springs 661A, 661B are inserted into the recessed regions 663A, 663B. Subsequently the membrane 140 is attached to the base 656, closing the springs 661A, 661B within the pump chambers 638A, 638B formed between the membrane 140 and the recessed regions 663A, 663B of the base 656.

Figure 17:
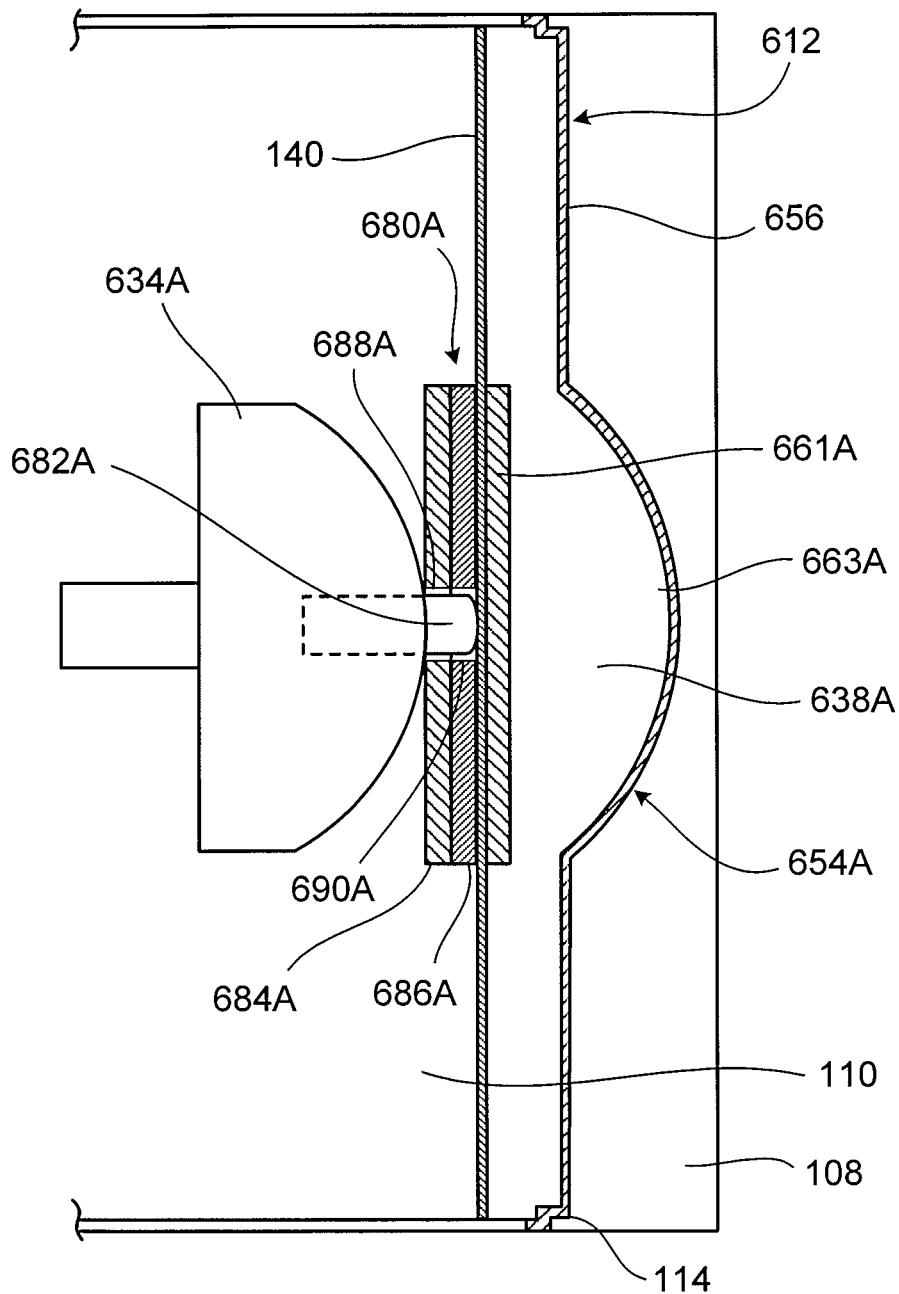
FIG. 17 is a cross-sectional, schematic of the PD cassette of FIG. 14 being used with a PD cycler that includes a secondary spring assembly attached to a piston.

While the pistons have been described as directly contacting the outer surface of the membrane 140 in the implementations described above, in certain implementations, a structure is positioned between each of the piston heads and the membrane 140. As shown in FIG. 17, for example, a secondary spring assembly 680A is releasably secured to a piston head 634A of a piston associated with the pump chamber 638A of the cassette 612 via a pin 682A. The secondary spring assembly 680A, as described below, acts to distribute the advancing force of the piston head 634A across substantially the entire surface of the spring 612A and the portion of the membrane 140 overlying the spring 612A. It should be understood that, although not shown, a similar secondary spring assembly would be connected to the piston head of a piston associated with the pump chamber 638B of the cassette 612.

The secondary spring assembly 680A includes a secondary spring 684A having a diameter that is substantially equal to the diameter of the spring 661A disposed in the pump chamber 638A of the cassette 612. The secondary spring 684A, like the spring 661A, is biased to a substantially flat or planar shape. The secondary spring 684A can be deformed to roughly conform to the shape of the piston head 634A as the piston head 634A is advanced into the recessed region 663A of the cassette base 656. The secondary spring 684A can be similar in design and construction to the springs 661A, 661B described above. Alternatively, other designs and constructions that provide the spring 684A with a planar bias while allowing the spring 684A to deform and roughly conform to the shape of the piston head 634A can be used.

A cover 686A is attached to the bottom surface of the secondary spring 684A. The cover 686A provides cushion between the springs 684A and 661A, and thus helps to prevent the membrane 140 from becoming damaged due to the forces of the springs 684A, 661A that act on the membrane 140. The cover 686A also helps to ensure that the portion of the membrane 140 overlying the spring 661A remains substantially smooth and wrinkle-free. This can help to increase the accuracy with which fluid is pumped from the pump chamber 638A. In some implementations, the cover 686A is formed of a foam material, such as polyurethane. However, other relatively soft materials that protect the membrane 140 from the springs 684A, 661A can be used. Examples of such materials include urethane foams and ethylene propylene diene monomer (EPDM).

As noted above, the secondary spring assembly 680A is releasably secured to the piston head 634A via the pin 682A. The pin 682A can be sized to create a press fit or friction fit with the secondary spring 684A and/or the cover 686A when the pin 682A is inserted into apertures 688A, 690A of those structures. Alternatively or additionally, the pin 682A can be equipped with a mechanical connector, such as a bayonet connector, that releasably engages the secondary spring 684A and/or the cover 686A when the pin 682A is inserted into the apertures 688A, 690A.

The piston with the attached secondary spring assembly 680A is used in the same manner as the piston described above to draw fluid into and force fluid out of the pump chambers 638A, 638B of the cassette 612. As the piston head 634A is advanced forward, the secondary spring assembly 680A contacts the outer surface of the membrane 140. Resistance to deformation of the secondary spring 684A causes the area of the membrane 140 positioned between the spring 661A and the secondary spring assembly 680A to be compressed between those structures as the piston advances forward. Similarly, due to the bias of each spring toward a flat or planar geometry, the portion of the membrane 140 positioned between the spring 661A and the secondary spring assembly 680A is compressed as the piston is retracted in those cases where the piston is retracted at a lower rate than or at the same rate that the spring 661A expands (i.e., returns to its planar configuration). This can improve the accuracy with which fluid is drawn into and pumped out of the pump chamber 638A.

While the secondary spring assembly 680A has been described as being releasably attached to the piston head 634A, permanent attachment techniques can alternatively be used to secure the secondary spring structure to the piston head. For example, the secondary spring structure can be thermally or chemically bonded to the piston head.

While the springs 661A, 661B have been illustrated as having eight discrete legs 665A, 665B extending from their hub portions 663A, 663B, the springs can have any number of legs that provide the springs with sufficient resiliency to apply a desired outward force to the membrane. In certain implementations, for example, the springs each include 16 legs extending from the hub portion. In some implementations, the hub portions of two of the above described springs are overlaid with one another and attached (e.g., thermally bonded, chemically bonded, or adhesively bonded) to one another. In such implementations, the springs can be arranged so that the fingers of one of the springs overlie the slots formed between adjacent fingers of the other spring.

Figure 18:
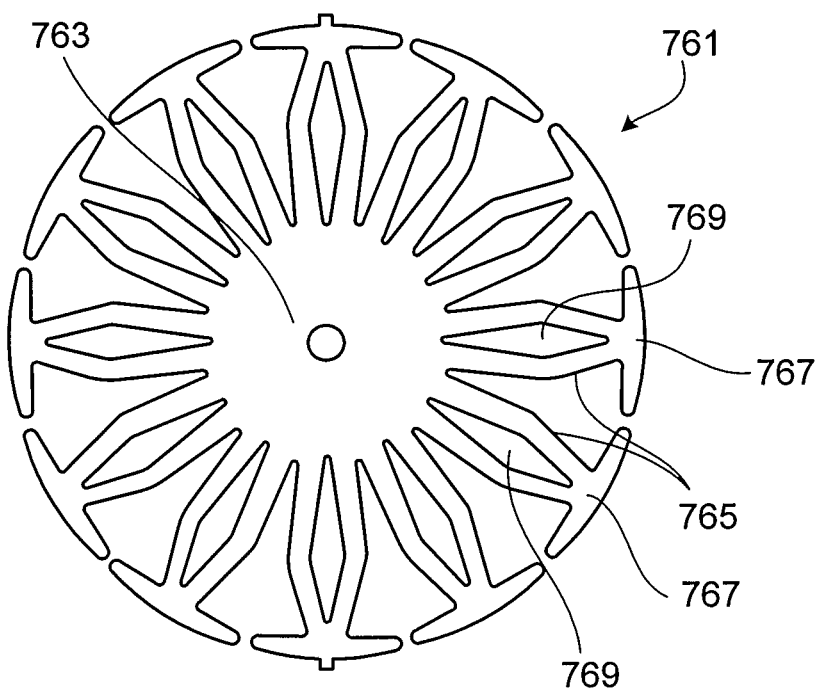
FIG. 18 is a top view of a spring that includes diamond-shaped legs extending from a hub portion and can be used in the cassettes of FIGS. 14 and 17.

Similarly, while the legs 665A, 665B of the springs 661A, 661B have been described and illustrated as discrete, elongate members, legs of other shapes and sizes can be used. As shown in FIG. 18, for example, a spring 761 includes 12 legs 765 that extend from a hub portion 763 and have pads or feet 767 attached to their ends opposite the hub portion 763. Each leg 765 is substantially diamond-shaped and includes a central, diamond-shaped aperture 769.

Figure 19:
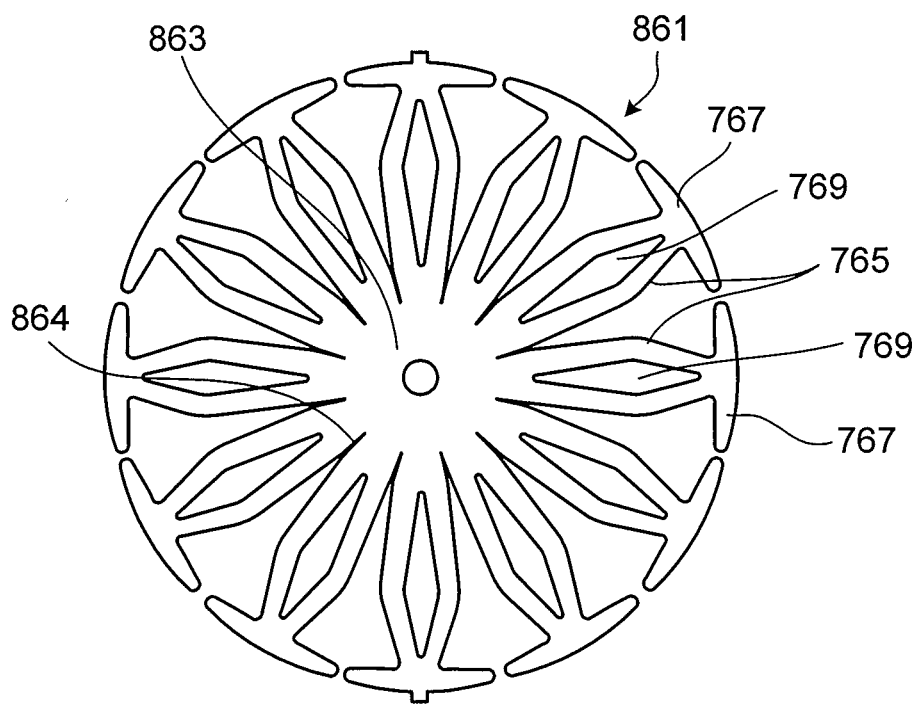
FIG. 19 is a top view of a spring that includes multiple legs extending from a hub portion having slits between adjacent legs and that can be used in the cassettes of FIGS. 14 and 17.

While the hub portions of the springs have been described as solid discs, in certain implementations, the hub portion of the spring includes slits between each of the fingers. As shown in FIG. 19, for example, a spring 861 includes the 12 legs 765 extending from a hub portion 863. The hub portion 863 includes slits 864 that extend radially inward from the circumference of the hub portion 863. The slits 864 are located between adjacent legs 765 of the spring 861 and can provide the legs 765 with a greater range of motion relative to the hub portion 863.

Figure 31:
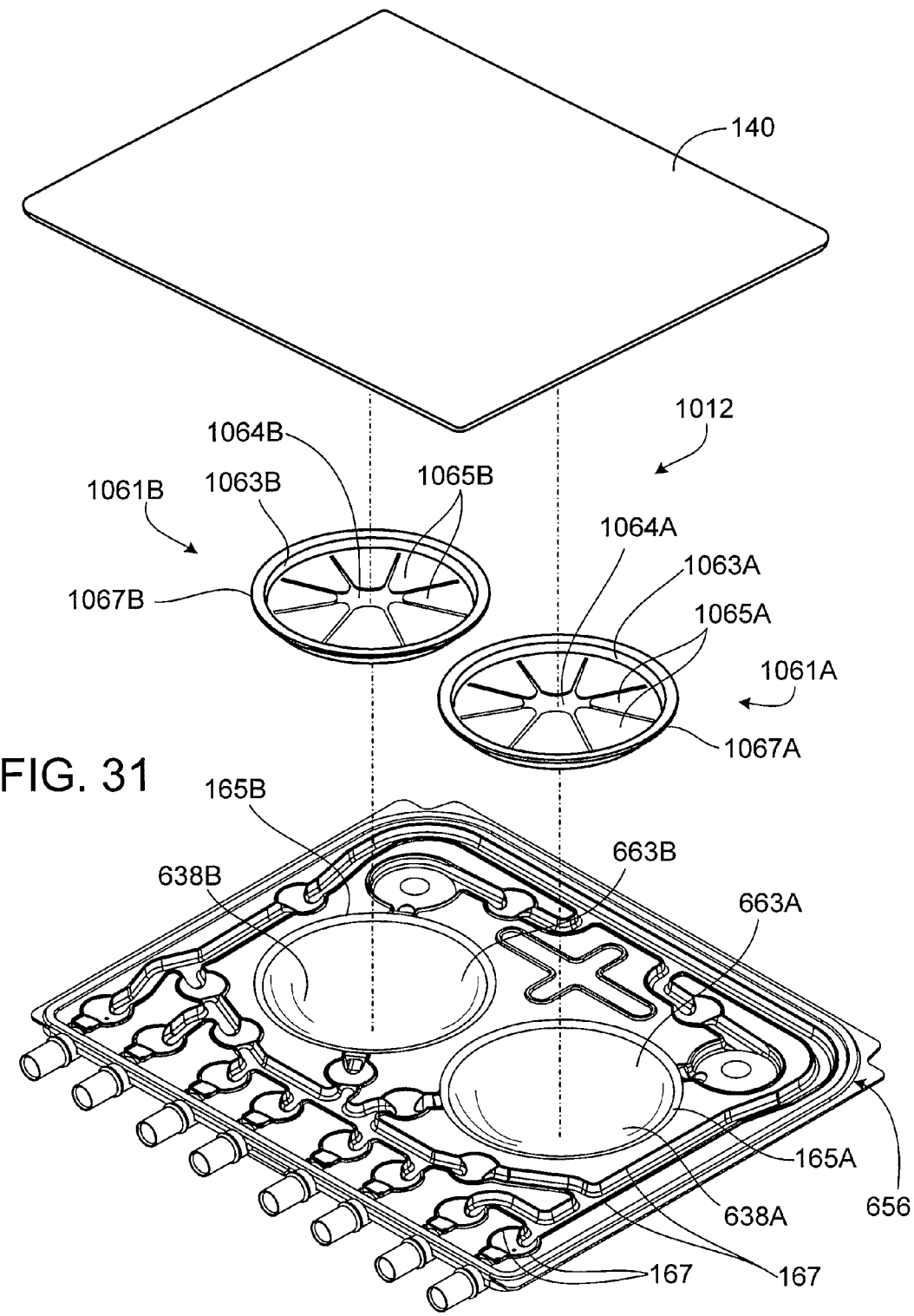
FIG. 31 is an exploded, perspective view of a PD cassette that includes a cup-shaped spring disposed in a pump chamber of the cassette.

While the springs of FIGS. 14-19 have been described as including legs that extend radially outward from a central hub portion, in certain implementations, springs including legs extending radially inward from an annular member are used. As shown in FIG. 31, for example, a cassette 1012 includes springs 1061A, 1061B disposed within pump chambers 638A, 638B formed between the base 656 in the membrane 140. Each of the springs 1061A, 1061B includes multiple legs 1065A, 1065B that extend from an annular ring 1063A, 1063B. The annular ring 1063A, 1063B includes a central aperture 1064A configured to receive the piston head of a dialysis machine. A flange 1067A, 1067B extends radially outward from the annular ring 1063A, 1063B. When the cassette 1012 is fully assembled with the springs 1061A, 1061B disposed within the pump chambers 638A, 638B, the flange 1067A, 1067B rests on the inner surface of the pump chamber 638A, 638B.

The springs 1061A, 1061B work in much the same way as the springs described above with respect to FIGS. 14-19. As the piston heads of the dialysis machine are advanced into the pump chambers 638A, 638B to force fluid out of the pump chambers 638A, 638B, the piston heads are received in the annular rings 1063A, 1063B of the springs 1061A, 1061B. As a result, the legs 1065A, 1065B are deflected toward the base 656 and generally conform to the inner surface of the pump chamber 638A, 638B. As the piston heads are subsequently retracted, the legs 1065a, 106 to return to their original, substantially planar position. In doing so, the legs 1065A, 1065B apply an outward force to the inner surface of the membrane 140, which causes the volume of the pump chambers 638A, 638B to increase and thus causes fluid to be drawn into the pump chambers 638A, 638B.

The springs 1061A, 1061B can be formed of any of the various materials discussed above with respect to the springs of FIGS. 14-19. In addition, while the springs 661A, 661B have been described as being loosely positioned within the pump chambers 638A, 638B, the springs 1061A, 1061B can alternatively be secured to the base 656 of the cassette 1012. The springs 1061A, 1061B can, for example, be press fit within the pump chambers 638A, 638B or bonded (e.g., thermally bonded, adhesively bonded, or chemically bonded) to the inner surface of the pump chambers 638A, 638B.

Figure 20:
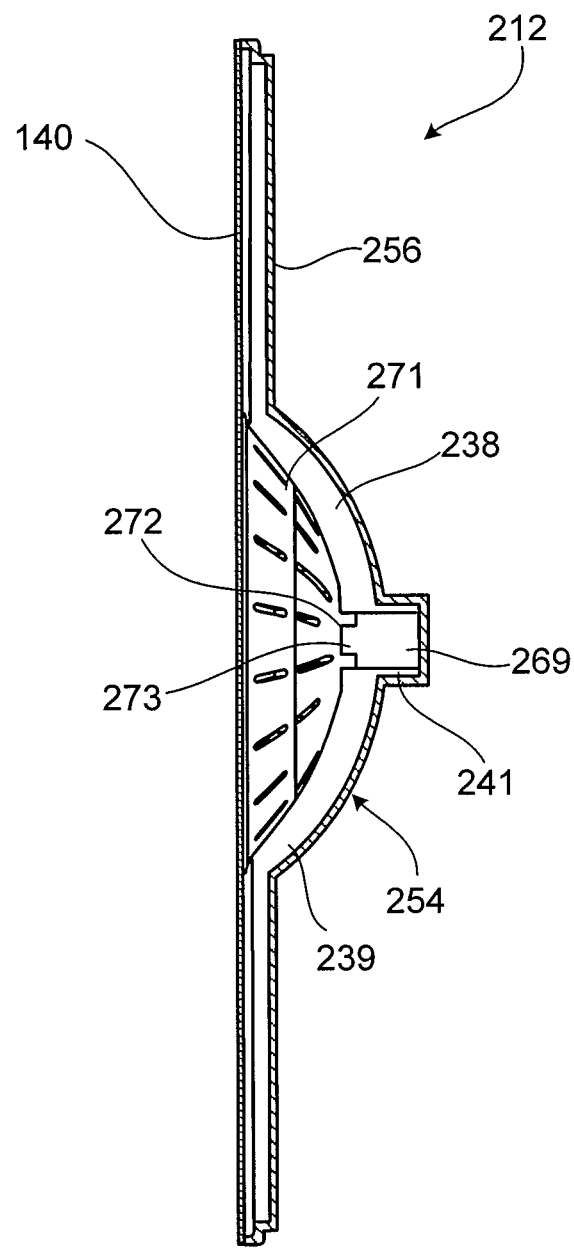
FIG. 20 is a diagrammatic cross-sectional view of a PD cassette that includes a resilient block disposed between a base of the cassette and a moveable cup-shaped member.

While the cassettes described above use spring members to apply an outward force directly to the cassette membrane 140, other types of self-expanding members can be disposed within the pump chambers and used to directly or indirectly apply an outward force to the membrane 140. As shown in FIG. 20, for example, a cassette 212 includes a resilient block 269 positioned between a rigid cassette base 256 and a cup-shaped member 271 that mates with the piston head 134A of the PD cycler 102 during use. The rigid base 256 includes a hollow projection 254 that forms a pump chamber 238. The pump chamber 238 includes a hemispherical section 239 shaped to receive the cup-shaped member 271 and a generally cylindrical section 241 shaped to receive the resilient block 269. The resilient block 269 is secured to the rigid base 256 within the cylindrical section 241 of the pump chamber 238. The resilient block 269 can, for example, be adhered or thermally bonded to the portion of the rigid base 256 forming the cylindrical section 241 of the pump chamber 238. A stem portion 273 of the resilient block 269 extends into a recess 272 formed in the cup-shaped member 271 and is secured to the cup-shaped member 271. The stem portion 273 of the resilient block 269 can, for example, be adhered to the cup-shaped member 271, thermally bonded to the cup-shaped member 271, and/or secured within the recess 272 of the cup-shaped member 271 using a friction fit technique. The resilient block 269 can be formed of any of various different elastomeric materials that permit the block to resiliently expand after being compressed. Examples of elastomeric materials that can be used to form the block include polyisoprene, polyurethane, latex, and silicone.

Figure 21:
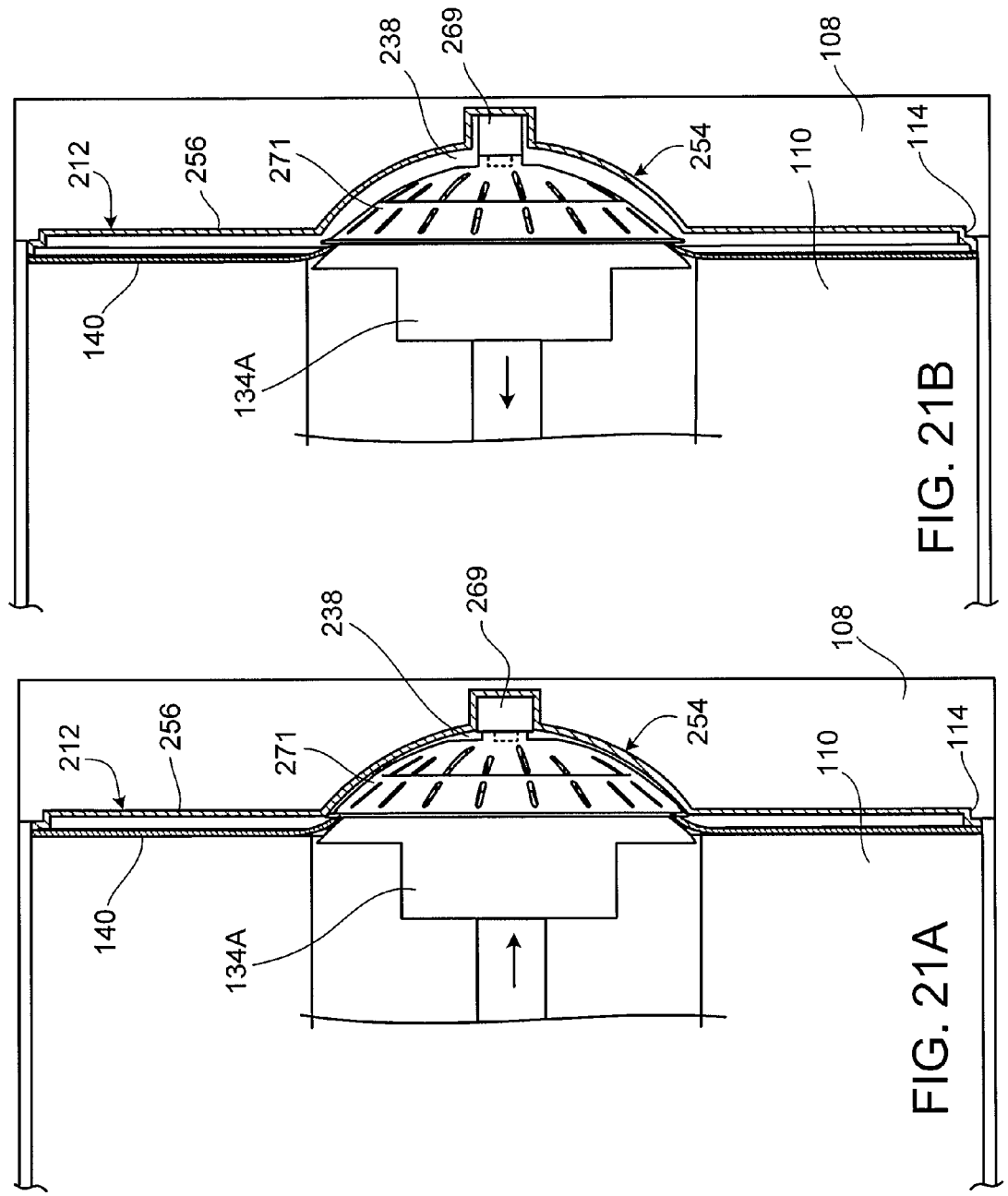
FIGS. 21A and 21B are diagrammatic cross-sectional views of the PD cassette of FIG. 20 in the cassette compartment of a PD cycler, during different phases of operation.

FIGS. 21A and 21B are diagrammatical cross-sectional views of the PD cycler 102 with the cassette 212 disposed in its cassette compartment 114, during different phases of operation. As shown in FIG. 21A, when the piston head 134A of the PD cycler 102 is extended, the piston head 134A pushes against the membrane 140 and the cup-shaped member 271 of the cassette 212, forcing the cup-shaped member 271 toward the rigid base 256 and causing the resilient block 269 to be compressed between the cup-shaped member 271 and the rigid base 256. This decreases the volume of the pump chamber 238 and expels dialysis solution from the pump chamber 238. When the piston head 134A is fully extended, the surface of the cup-shaped member 271 opposite the piston head 134A contacts or nearly contacts the inner surface of the hollow projection 254 forming the pump chamber 238. The cup-shaped member 271 and the hollow projection 254 have mating hemispherical shapes to reduce (e.g., minimize) the fluid volume between the surfaces of the cup-shaped member 271 and the hollow projection 254 when the piston head 134A is in its fully extended position. This configuration can help to reduce (e.g., minimize) the amount of dialysis solution that remains in the pump chamber 238 after extending the piston head 134A to expel the dialysis solution from the pump chamber 238.

As shown in FIG. 21B, due to the resiliency of the block 269, when the piston head 134A is retracted, the resilient block 269 expands, causing the cup-shaped member 271 to apply an outward force to the inner surface of the membrane 140 of the cassette 212. As a result, the volume of the pump chamber 238 increases, causing dialysis solution to be drawn into the pump chamber 238.

As an alternative to or in addition to the resilient block 269, another type of resilient member, such as a compression spring, could be positioned between the rigid base 256 and the cup-shaped member 271. Such a spring would work in a manner similar to the resilient block 269 discussed above to move the membrane 140 away from the rigid base 256 and increase the volume of the pump chamber 238 when the piston head 134A is retracted.

It should be understood that even though only one of the pump chambers of the cassette 212 has been illustrated, the cassette 212 includes two pump chambers each of which contains a cup-shaped member and a resilient member for moving the cup-shaped member within the pump chamber.

As discussed above, the piston heads 134A, 134B can be reciprocated to repeatedly draw dialysis solution into the pump chambers and then expel the dialysis solution from the pump chambers.

Figure 22:
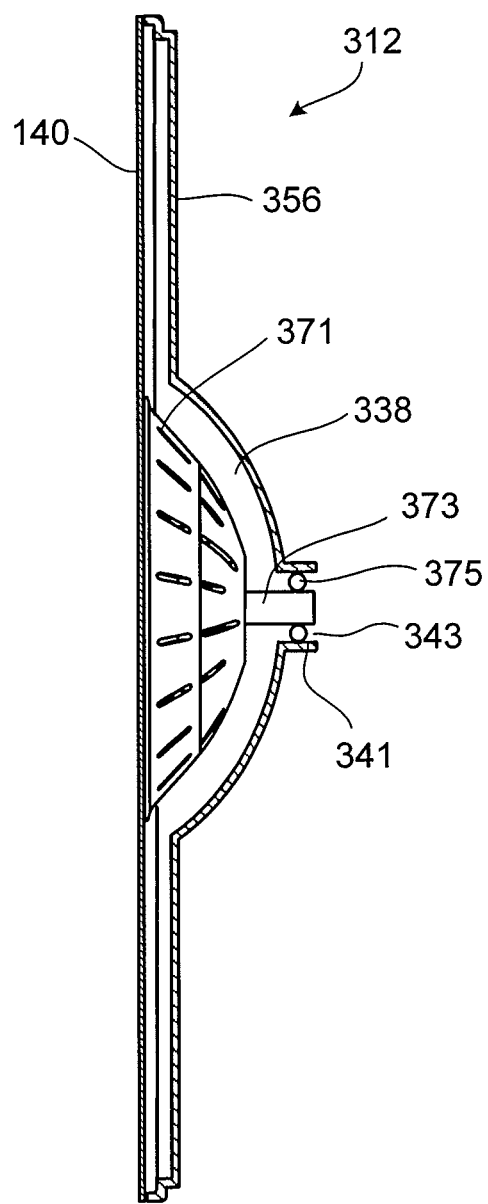
FIG. 22 is a diagrammatic cross-sectional view of a PD cassette that includes a moveable cup-shaped member configured to be operated by a spring loaded piston of a PD cycler.

While the cassettes discussed above include self-expanding members to apply an outward force to the membrane, in some implementations, the cassette is configured to cooperate with a moveable member of the PD cycler in a way such that the moveable member of the PD cycler can apply an outward force to the inner surface of the cassette membrane. Referring to FIG. 22, for example, a cassette 312 includes a rigid base 356 that together with the cassette membrane 140 forms a pump chamber 338. A passage 341 extends through the base 356, from the pump chamber 338 to an opening 343 formed in the base 356. A cup-shaped member 371 is disposed in the pump chamber 338 and includes a stem portion 373 positioned in the passage 341 of the base 356. An o-ring 375 surrounds the stem portion 373 of the cup-shaped member 371 and forms a liquid-tight seal with the stem portion 373 and the surrounding portion of the rigid base 356 such that dialysis solution within the pump chamber 338 cannot escape via the passage 341.

Figure 23A:
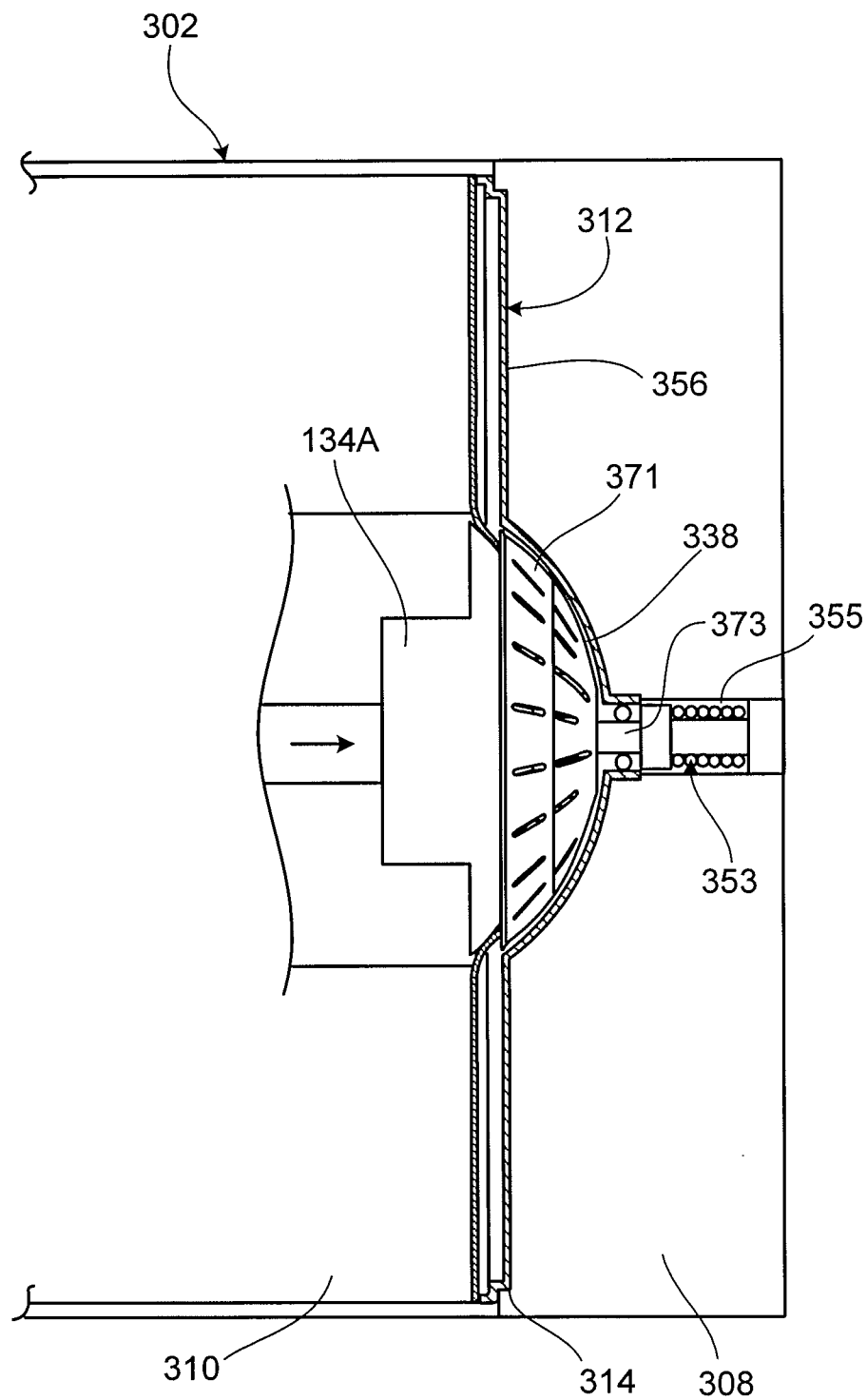
FIGS. 23A and 23B are diagrammatic cross-sectional views of the PD cassette of FIG. 22 in the cassette compartment of a PD cycler, during different phases of operation.
Figure 23B:
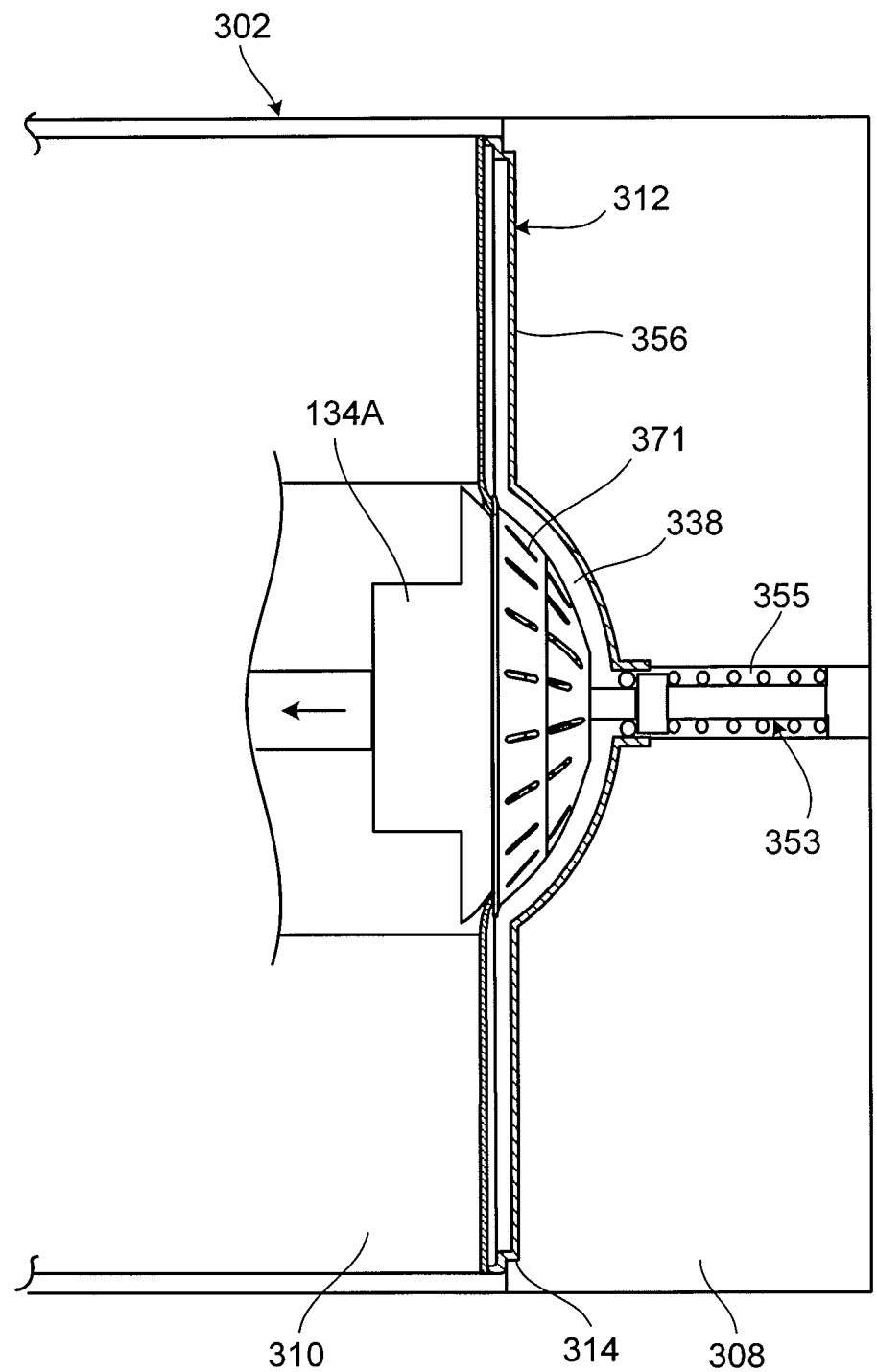

FIGS. 23A and 23B are diagrammatical, partial cross-sectional views of a PD cycler 302 with the cassette 312 disposed in its cassette compartment 314, during different phases of operation. As shown in FIG. 23A, a door 308 of the PD cycler 302 includes a spring-loaded piston 353 that aligns with the stem portion 373 of the cup-shaped member 371 when the cassette 312 is disposed within the cassette compartment 314 formed between the closed door 308 and a cassette interface 310 of the PD cycler 302. The cassette 312 can be positioned within the cassette compartment 314 by securing the cassette 312 to the cassette interface 310 when the door 308 is in an open position, and then closing the door 308.

Still referring to FIG. 23A, when the piston head 134A is moved to an extended position, the piston head 134A pushes against the membrane 140 and the cup-shaped member 371, compressing the spring-loaded piston 353 within a bore 355 formed in the door 308. In the fully extended position of the piston head 134A, the surface of the cup-shaped member 371 opposite the piston head 134A contacts or nearly contacts the inner surface of the portion of the rigid base 356 forming the pump chamber 338. As a result, the volume of the pump chamber 338 decreases and dialysis solution is expelled from the pump chamber 338. The cup-shaped member 371 and the pump chamber 338 have mating shapes to reduce (e.g., minimize) the fluid volume between the surfaces of the cup-shaped member 371 and the base 356 when the piston head 134A is in its fully extended position. This configuration can help to reduce (e.g., minimize) the amount of dialysis solution that remains in the pump chamber 338 after extending the piston head 134A to expel the dialysis solution from the pump chamber 338.

As shown in FIG. 23B, due to the resiliency of the spring-loaded piston 353, as the piston head 134A is retracted, the spring-loaded piston 353 moves toward the membrane 140 and causes the cup-shaped member 371 to apply an outward force to the membrane 140. As a result, the volume of the pump chamber 338 increases and dialysis solution is drawn into the pump chamber 338.

It should be understood that even though only one of the pump chambers of the cassette 312 has been illustrated, the cassette 312 includes two pump chambers each of which contains a cup-shaped member that is actuated by a spring-loaded piston of the PD cycler during use. As discussed above, the piston heads 134A, 134B can be reciprocated to repeatedly draw dialysis solution into the pump chambers and then expel the dialysis solution from the pump chambers.

Figure 24:
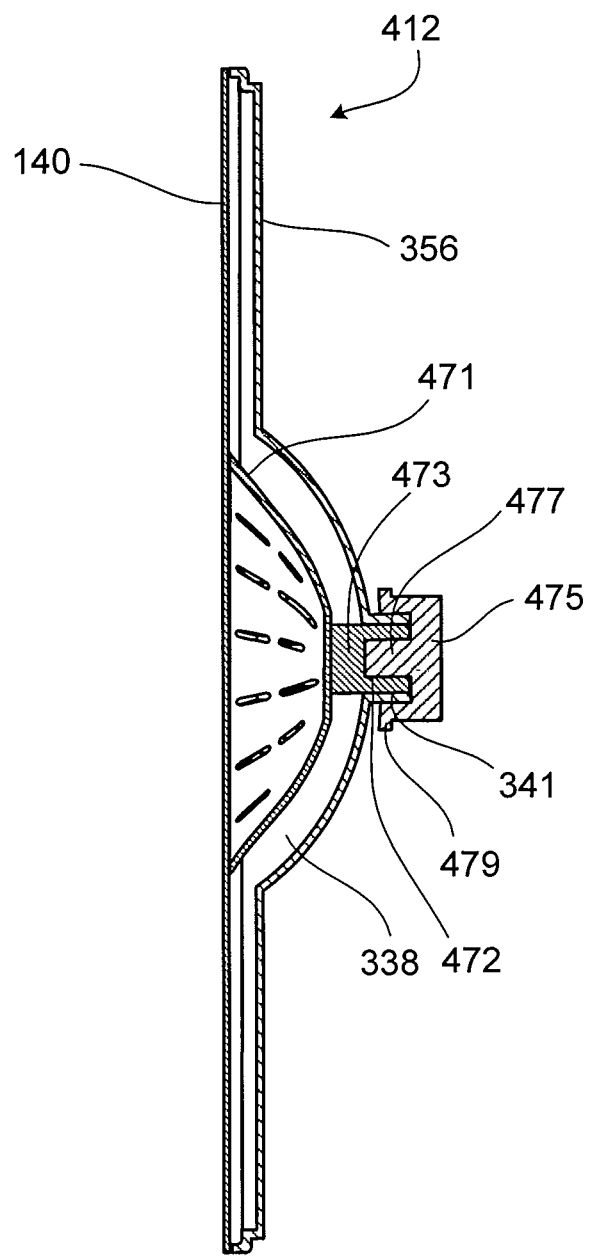
FIG. 24 is a diagrammatic cross-sectional view of another type of PD cassette that includes a moveable cup-shaped member configured to be operated by a spring loaded piston of a PD cycler.

While the cassette 312 has been described as including an o-ring surrounding the stem portion 373 of the cup-shaped member 371 to prevent liquid from escaping from the pump chamber 338, other techniques can be used to seal the pump chamber 338. As shown in FIG. 24, for example, an elastomeric cap seal 475 is attached to the rigid base 356 of a cassette 412 and seals the passage 341 in which a stem portion 473 of a cup-shaped member 471 is disposed. The cap seal 475 includes a post 477 that extends into a recess 472 formed in the stem portion 473 of the cup-shaped member 471. The post 477 of the cap seal 475 is attached to the stem portion 473 of the cup-shaped member 471. The post 477 of the cap seal 475 can, for example, be adhered to the stem portion 473 of the cup-shaped member 471, thermally bonded to the stem portion 473 of the cup-shaped member 471, and/or secured within the recess of the stem portion 473 of the cup-shaped member 471 using a friction fit technique. The cap seal 475 also includes an annular ridge 479 that surrounds the portion of the rigid base 356 that forms the passage 341. The cap seal 475 is attached to the rigid base 356 of the cassette 412. For example, the annular ridge 479 of the cap seal 475 can be adhered or thermally bonded to the rigid base 356. The cap seal 475 can be formed of any of various different elastomeric materials that permit the seal 475 to return back to its original configuration after being elastically stretched. Examples of elastomeric materials that can be used to form the cap seal 475 include polyisoprene, polyurethane, latex, and silicone.

Figure 25A:
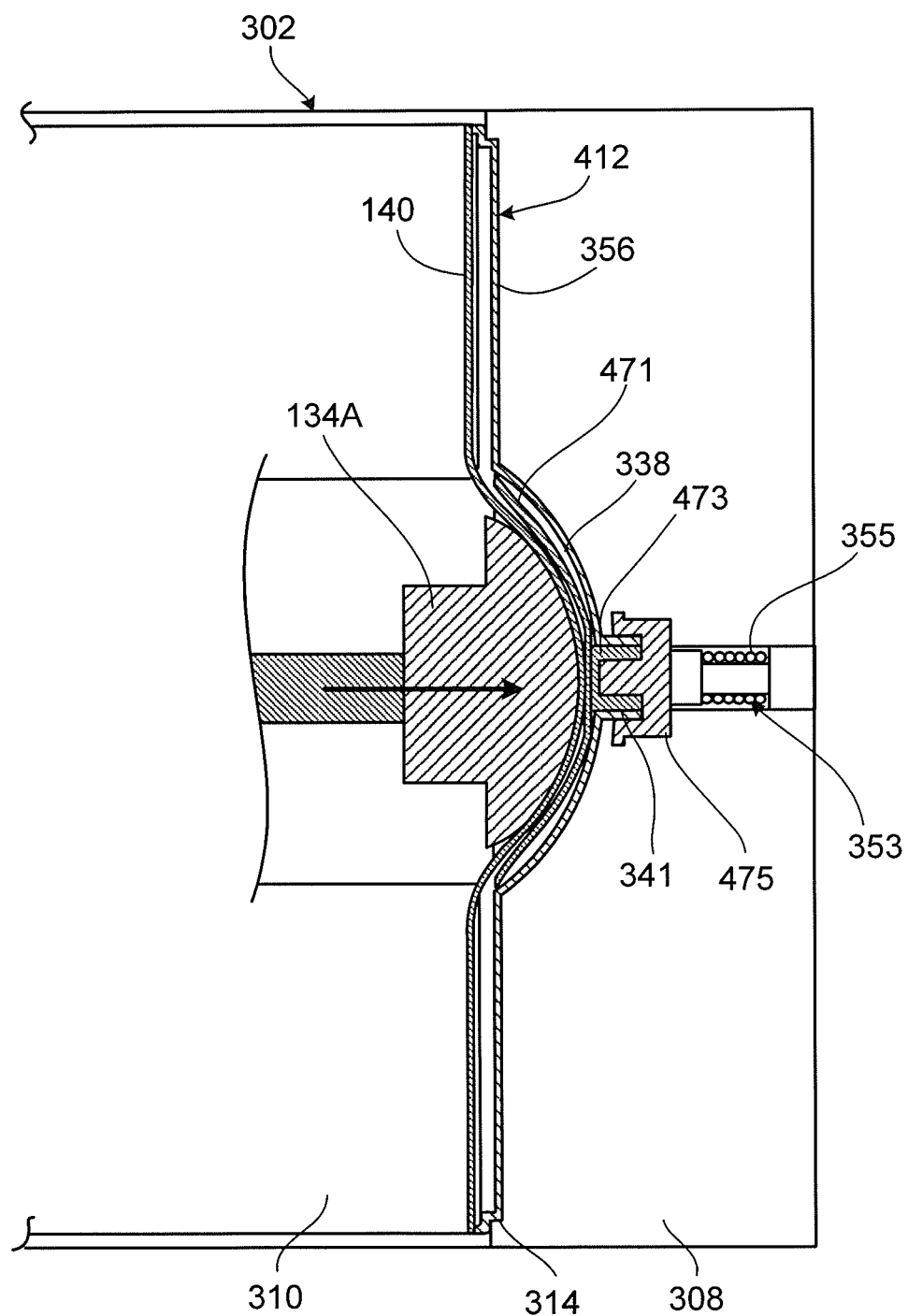
FIGS. 25A and 25B are diagrammatic cross-sectional views of the PD cassette of FIG. 24 in the cassette compartment of a PD cycler, during different phases of operation.
Figure 25B:
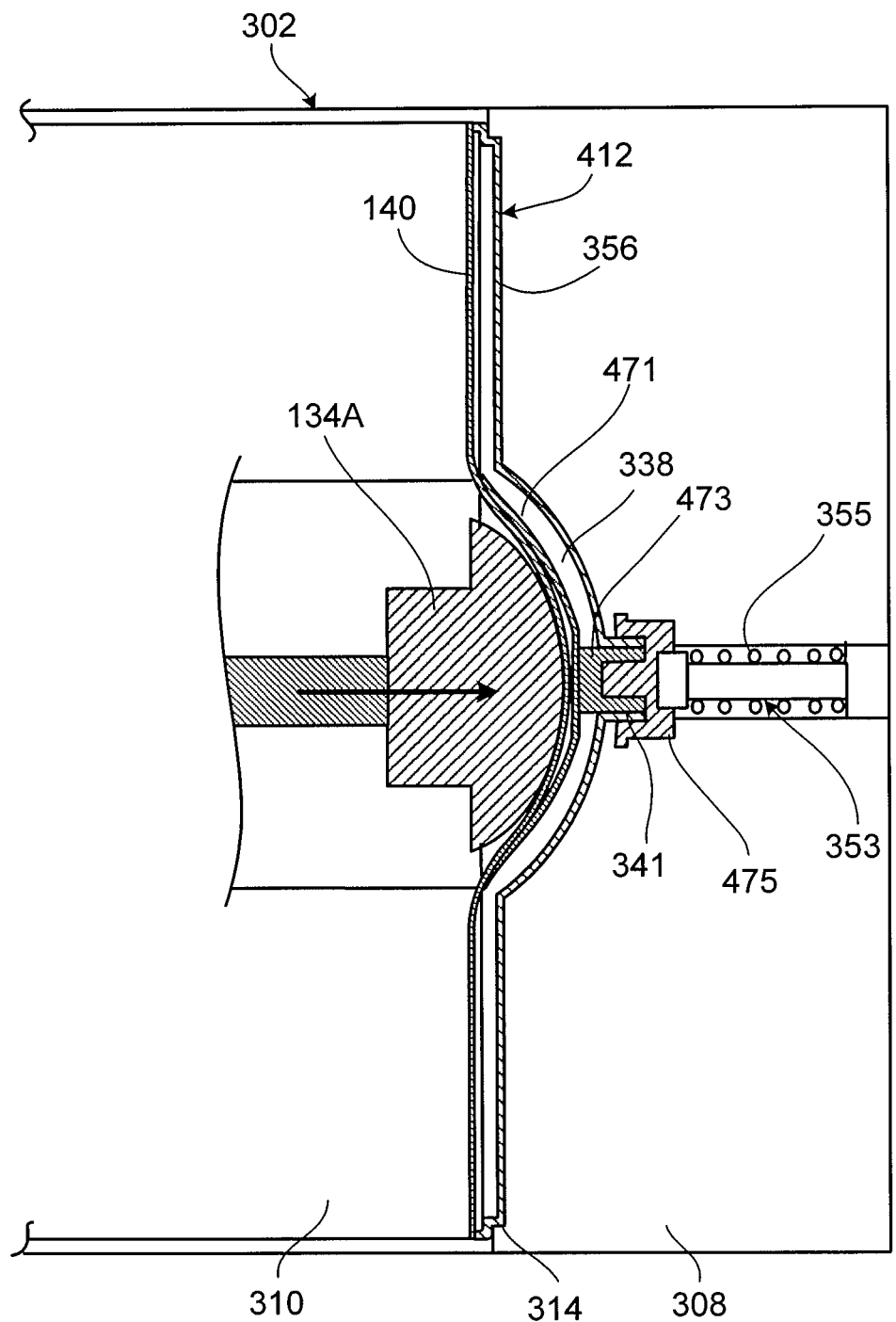

FIGS. 25A and 25B are diagrammatical cross-sectional views of the PD cycler 302 with the cassette 412 disposed in its cassette compartment 314, during different phases of operation. As shown in FIG. 25A, when the piston head 134A is moved to an extended position to force dialysis solution out of the pump chamber 338, the piston head 134A pushes against the membrane 140 and the cup-shaped member 471 and forces the stem portion 473 of the cup-shaped member 471 fully into the passage 341. In this position, the surface of the cup-shaped member 471 opposite the piston head 134A contacts or nearly contacts the inner surface of the portion of the rigid base 356 forming the pump chamber 338 and the cap seal 475 is in an undeformed configuration. The stem portion 473 compresses the spring-loaded piston 353 when the piston head 134A is fully extended.

Referring to FIG. 25B, as the piston head 134A is retracted, the spring-loaded piston 353 moves the cap seal 475 and the cup-shaped member 471 toward the membrane 140 and causes the cup-shaped member 471 to apply an outward force to the inner surface of the membrane 140. As a result, the volume of the pump chamber 338 increases and dialysis solution is drawn into the chamber 338. As the cap seal 475 deforms into the passage 341, the liquid-tight seal between the cap seal 475 and the rigid base 356 is maintained such that the dialysis solution being drawn into the pump chamber 338 cannot escape.

While the cap seal 475 has been described as including a post 477 that fits into the recess in the stem portion 473 of the cup-shaped member 471, any of various other configurations that permit the cap seal to be attached to the cup-shaped member can be used.

It should be understood that even though only one of the pump chambers of the cassette 412 has been illustrated, the cassette 412 includes two pump chambers each of which contains a cup-shaped member that is actuated by a spring-loaded piston of the PD cycler during use. As discussed above, the piston head 134A, 134B can be reciprocated to repeatedly draw dialysis solution into the pump chambers and then expel the dialysis solution from the pump chambers.

As an alternative to or in addition to using a spring-loaded piston 353 to apply a force to the stem portion 373 of the cup-shaped member 371 or to the cap seal 475, other types of self-expanding resilient members, such as compression springs or elastomeric members, can be used. The door 308 of the PD cycler 302 can, for example, be equipped with other types of self-expanding resilient members, such as a compression springs or elastomeric members, arranged to apply a force to the stem portion 373 of the cup-shaped member 371 or to the cap seal 475 during use. Such self-expanding resilient members would work in a manner similar to the resilient block 269 discussed above to move the membrane 140 away from the rigid base 356 of the cassette 312, 412 and increase the volume of the pump chamber 338 when the piston head 134A is retracted. Similarly, as an alternative to or in addition to self-expanding resilient members, the door 308 of the PD cycler 302 can include actuatable members, such as electrically, hydraulically, and/or pneumatically operated members, arranged to apply a force to the stem portion 373 of the cup-shaped member 371 or to the cap seal 475.

In some implementations, the self-expanding or actuatable members used to apply a force to the stem portion 373 of the cup-shaped member 371 or to the cap seal 475 can be adjustable to provide different magnitudes of force to the cup-shaped member 371 or to the cap seal 475. In certain implementations, the self-expanding or actuatable members used to apply a force to the stem portion 373 of the cup-shaped member 371 or to the cap seal 475 can be easily replaced with other self-expanding or actuatable members that provide different magnitudes of force. In such implementations, the cassettes 312, 412 can be used without modification for any of various different types of applications that require different magnitudes of force to be applied the inner surface of the membrane 140.

In certain implementations, the door of the PD cycler includes a mechanism configured to transfer an inward force of one of the cup-shaped members to the other cup-shaped member in the form of an outward force. For example, referring to FIG. 26, which is a top cross-sectional view of a cassette 512 (similar to the cassette 312 discussed above with respect to FIGS. 22, 23A, and 23B) in a cassette compartment 514 formed between a closed door 508 and a cassette interface 510 of a PD cycler 502, the door 508 of the PD cycler 502 includes a pivotable rod 553 with projections 555A, 555B at opposite ends of the rod 553. The projections 555A, 555B contact stem portions 573A, 573B of their associated cup-shaped members 571A, 571B in pump chambers 538A, 538B the cassette 512. The rod 553 is pivotable about a central pivot axis 557. In some implementations, for example, a pin is inserted though a hole formed in the rod and the pin is attached to the door of the PD cycler so that the rod 553 can pivot about the pin. However, any of various other mechanisms can alternatively or additionally be used to pivotably attach the rod 553 to the door 508.

During use, the piston heads 134A, 134B of the PD cycler 502 are operated in an alternating fashion such that one of the piston heads is extended as the other piston head is retracted and vice versa. As shown in FIG. 26, as the piston head 134A is extended and pushes the cup-shaped member 571A into the pump chamber 538A to expel dialysis solution from the pump chamber 538A, the rod 553 pivots about the pivot axis 557. In particular, the end 555A of the rod 553 in contact with the cup-shaped member 571A moves away from the pump chamber 538A, and the opposite end 555B of the rod 553 moves toward the pump chamber 538B. As a result, the opposite end 555B of the rod 553 moves the other cup-shaped member 571B away from the rigid base 556 of the cassette 512, causing the cup-shaped member 571B to apply an outward force to the membrane 140 of the cassette 512. Due to the outward force applied to the membrane 140, as the piston head 134B is retracted, the volume of the pump chamber 538B increases and dialysis solution is drawn into the pump chamber 538B. After drawing dialysis solution into the pump chamber 538B, the piston head 134B is extended, forcing the cup-shaped member 571B into the pump chamber 538B to expel dialysis solution from the pump chamber 538B, while, at the same time, the piston head 134A is retracted and the cup-shaped member 571A is forced away from the base 556 to draw dialysis solution into the pump chamber 538A. In some implementations, the piston heads 134A, 134B are retracted and extended at substantially the same rate so that each of the cup-shaped members 571A, 571B remains in close contact with its associated piston head 134A, 134B throughout the pumping process.

While the piston heads 134A, 134B of the PD cyclers above have been described as being hemispherical, the piston heads could be any of various other shapes. In some implementations, for example, the piston heads can have flat end surfaces. In such implementations, the cup-shaped members disposed in the pump chambers of the cassette can have flat surfaces that abut the flat end surfaces of the piston heads during use. Similarly, while the piston heads 134A, 134B have been described as being formed using certain materials and manufacturing techniques, any of various other suitable materials and manufacturing techniques could alternatively be used.

Figure 27:
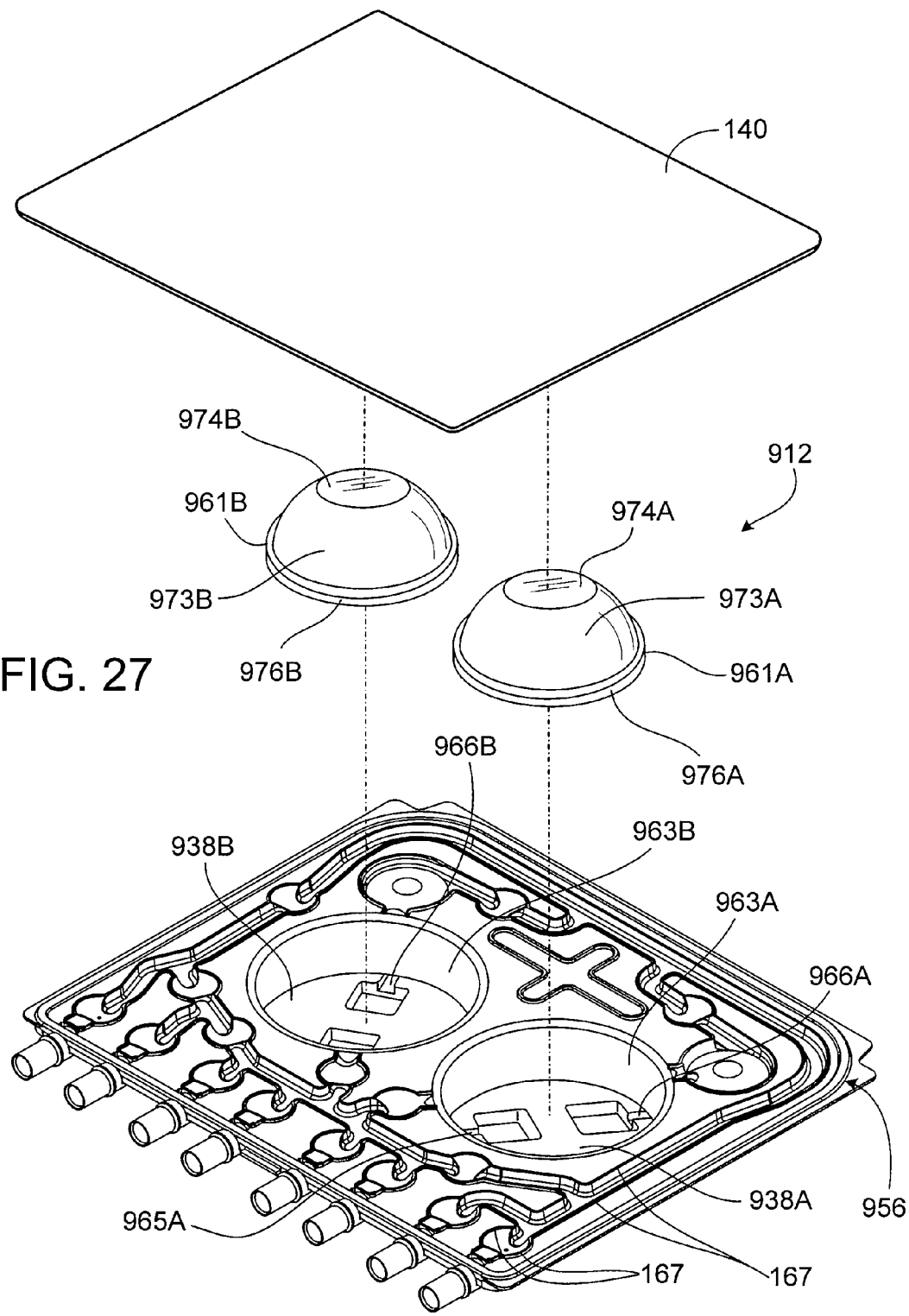
FIG. 27 is an exploded, perspective view of a PD cassette that includes a resilient, substantially dome-shaped member disposed in a chamber of the cassette.

While the members (e.g., springs) disposed within the pump chambers of the above-described cassettes are designed to allow liquid to pass therethrough, in certain implementations, the cassettes are equipped with liquid-impermeable self-expanding members such that liquid pumped into and out of the pump chambers of the cassettes is contained by the self-expanding members. As shown in FIG. 27, for example, a cassette 912 includes resilient, dome-shaped members 961A, 961B that are disposed in pump chambers 938A, 938B formed between the membrane 140 and cylindrical recessed regions 963A, 963B of a base 956 of the cassette 912. The dome-shaped members 961A, 961B are liquid-impermeable and are retained in the recessed regions 963A, 963B in a manner such that a fluid tight seal is provided around the circumference of each of the dome-shaped members 961A, 961B. During use, as will be described in greater detail below, fluid is drawn into and forced out of fluid chambers 972A, 972B formed in the bottom portions of the recessed regions 963A, 963B, between the inner surfaces of the dome-shaped members 961A, 961B and underlying surface areas of the base 956.

Figure 28:
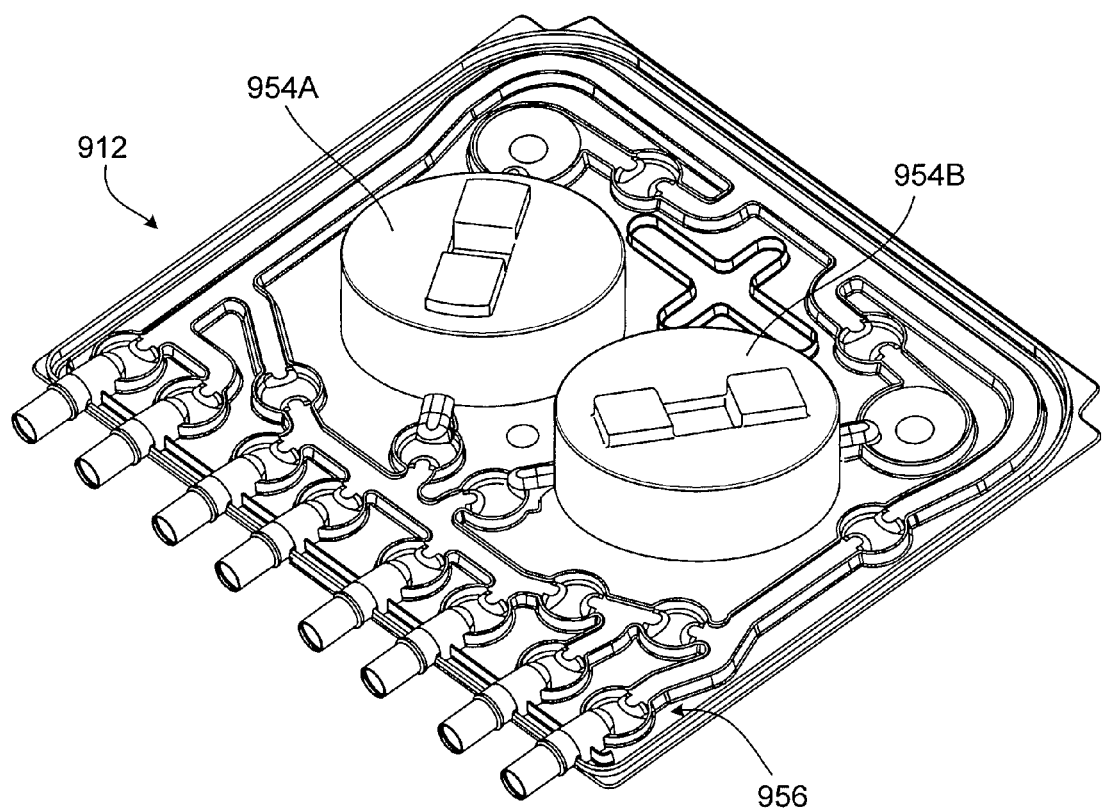
FIG. 28 is a perspective view of the PD cassette of FIG. 27, from a rigid base side of the PD cassette.

The base 956 of the cassette 912 is similar to the bases of those cassettes described above. However, the recessed regions 963A, 963B and fluid inlet and outlet passages leading to the recessed regions 963A, 963B have different configurations than corresponding features in the cassettes described above. As shown in FIGS. 27 and 28, the base 956 includes hollow, substantially cylindrical projections 954A, 954B that form the cylindrical recessed regions 963A, 963B. Unlike the bases described above, which include fluid inlet and outlet ports near the ends of the recessed regions closest to the membrane 140, fluid inlet ports 965A, 965B and outlet ports 966A, 966B are formed in the side wall of the cylindrical projections 954A, 954B, near the ends of the recessed regions 963A, 963B opposite the membrane 140. Thus, when the cassette 912 is fully assembled, as shown in FIG. 29, the fluid inlet ports 965A, 965B and outlet ports 966A, 966B are positioned below the dome-shaped members 961A, 961B.

Figure 29:
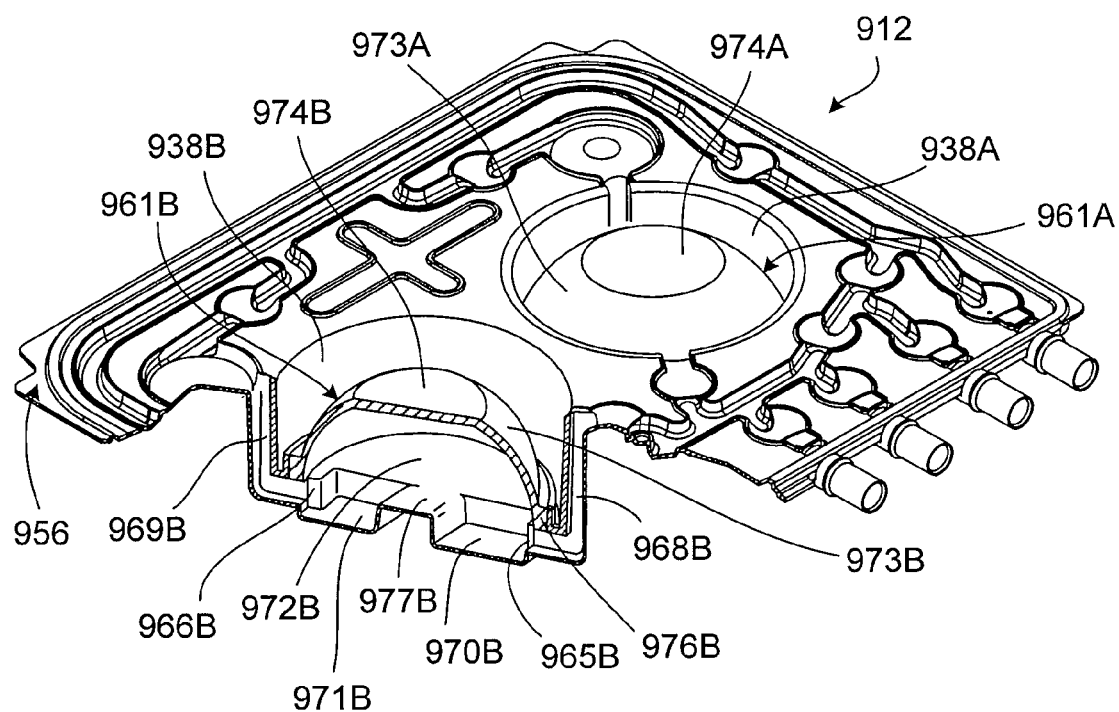
FIG. 29 is a perspective, cut-away view of the PD cassette of FIG. 27.

As shown in FIG. 29, the base 956 of the cassette 912 forms vertical fluid passages 968B, 969B that extend from fluid channels formed along the top surface (from the perspective shown in FIG. 29) of the base 956 to the fluid inlet and outlet ports 965B, 966B. These passages 968B, 969B extend along the outer surface of the cylindrical projection 954B in which the dome-shaped member 961B is disposed. The surface region of the base 956 that underlies the dome-shaped member 961B forms channels 970B, 971B that are aligned with the fluid inlet and outlet ports 965B, 966B to allow fluid to flow underneath the dome-shaped member 961B and into a fluid pump chamber 972B formed between the dome-shaped member 961B and the base 956. Those channels 970B, 971B are divided by a raised surface 977B of the base 956 that extends upward toward the dome-shaped member 961B. Although not shown, the portion of the base 956 underneath the dome-shaped member 961A is generally the same as the corresponding portion of the base 956 underneath the dome-shaped member 961B.

As shown in FIGS. 27 and 29, each of the dome-shaped members 961A, 961B includes a body 973A, 973B that has a flattened top 974A, 974B and an annular flange or ring 976A, 976B that extends about the circumference of a lower end region of the body 973A, 973B. The dome-shaped members 961A, 961B are formed of materials and have dimensions that permit the dome-shaped members 961A, 961B to resiliently self-expand after being compressed. In some implementations, the dome-shaped members 961A, 961B are formed of polyurethane. However, other resilient materials, such as silicone, styrenic block copolymers (e.g., Kraton D), chloroprene, polychloroprene (e.g., Neoprene), and/or thermoplastic elastomers (e.g., Mediprene), can alternatively or additionally be used to form the dome-shaped members 961A, 961B.

The dome-shaped members are sized so that a desired volume (e.g., 12.75 mL) of fluid is pumped into and out of the chambers 972A, 972B formed between the dome-shaped members 961A, 961B and the base 956 of the cassette 912 when the dome-shaped members 961A, 961B are fully compressed and then allowed to fully expand. The dome-shaped members 961A, 961B can, for example, have a diameter of about 50 mm to about 56 mm, a height (i.e., the perpendicular distance from the lower surface of the side wall to the top surface of the flat top 974A, 974B) of about 17 mm to about 23 mm, and a wall thickness of about 1.5 mm to about 3.5 mm.

In certain implementations, the dome-shaped members are formed of polyurethane, have a diameter of 53 mm, a height of 20 mm, and a wall thickness of 2.4 mm.

Referring again to FIG. 29, the dome-shaped members 961A, 961B are press fitted into the recessed regions 963A, 963B formed by the cylindrical projections 954A, 954B. In particular, the flange 976A, 976B of each of the dome-shaped members 961A, 961B has a diameter that is about 0.020 inch greater than the diameter of the recessed regions 963A, 963B (i.e., the inner diameter of the cylindrical projections 954A, 954B). This configuration both secures the dome-shaped members 961A, 961B within the recessed regions 963A, 963B and provides a liquid-tight seal between the dome-shaped members 961A, 961B and the inner surfaces of the cylindrical projections 954A, 954B of the base 956. In addition, because the membrane 140 extends over the recessed regions 963A, 963B and is sealed around the periphery of the base 956, the membrane 140 provides a secondary liquid-tight seal that prevents liquid from escaping from the cassette 912 even in the event that liquid passes between the dome-shaped members 961A, 961B and the base 956.

Figure 30:
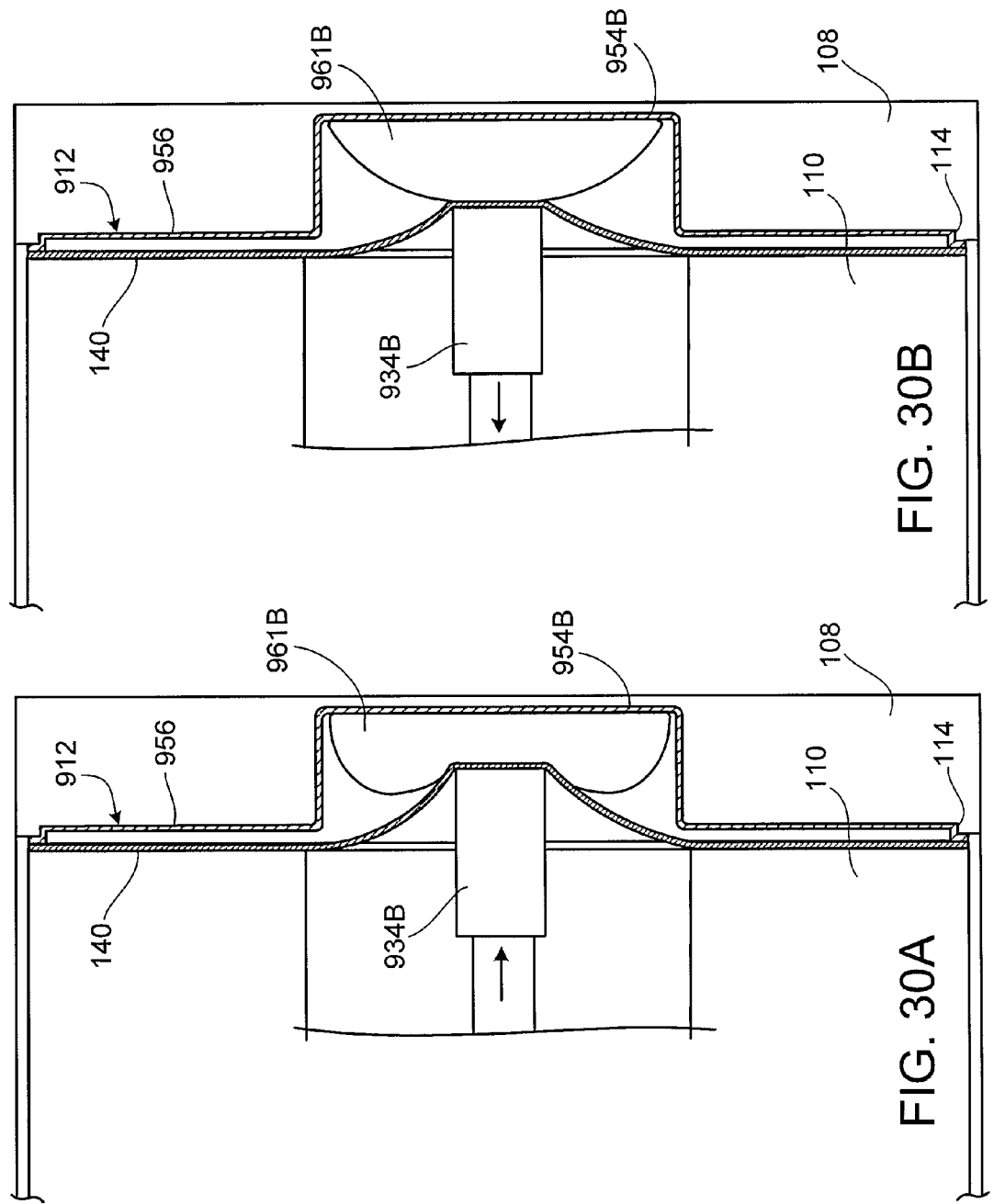
FIGS. 30A and 30B are diagrammatic cross-sectional views of the PD cassette of FIG. 27 in the cassette compartment of a PD cycler, during different phases of operation.

The cassette 912 is used to pump fluid in much the same way as the cassettes described above. FIGS. 30A and 30B show the cassette 912 disposed within the cassette compartment 114 of the PD cycler 102 during different stages of the pumping process. As shown in FIG. 30A, a flat piston head 934B of a piston of the PD cycler 102, has compressed the dome-shaped member 961B to force fluid out of the fluid chamber 972B formed between the dome-shaped member 961B and the cylindrical projection 954B. As the dome-shaped member 961B is compressed, the fluid flows through the channel 971B, out the fluid outlet port 966B, and into the vertical passage 969B (all shown in FIG. 29). FIG. 30B shows the piston being retracted such that the dome-shaped member 961B has been allowed to expand and draw fluid back into the chamber 972B formed between the dome-shaped member 961B and the cylindrical projection 954B. As the dome-shaped member 961B expands, fluid passes through the vertical passage 968B, in the fluid inlet port 965B, and through the channel 970B (all shown in FIG. 29). Because the channels 970B, 971B are recessed relative to the surface 977B, the channels 970B, 971B ensure fluid communication between fluid chamber 972B and the inlet and outlet ports 965B, 966B even when the dome-shaped member 961B has been fully compressed into contact or near contact with the surface 977B.

The cassette 912 can be assembled by press-fitting the dome-shaped members 961A, 961B into the recessed regions 963A, 963B of the base 956, and then attaching the membrane 140 to the periphery of the base 956 in the manner described above with respect to other cassettes.

While the flanges or rings 976A, 976B of the dome-shaped members 961A, 961B have been described as being pressed against flat inner surfaces of the cylindrical projections 954A, 954B, the inner surfaces of the cylindrical projections 954A, 954B can alternatively include annular depressions in which the flanges 976A, 976B are received. This arrangement results in a tortuous path between the flanges 976A, 976B of the dome-shaped members 961A, 961B and adjacent surfaces of the cylindrical projections 954A, 954B, which can also help to prevent liquid from passing between the flanges 976A, 976B and the cylindrical projections 954A, 954B.

As another alternative, the dome-shaped members 961A, 961B can be bonded (e.g., thermally bonded, chemically bonded, or adhesively bonded) to the cylindrical projections 954A, 954B of the base 956.

While the dome-shaped members 961A, 961B have been described as being press fit or bonded within the recessed regions 963A, 963B formed by the cylindrical projections 954A, 954B, the dome-shaped members 961A, 961B can alternatively be formed with the base 956 of the cassette 912 using a mold in technique. To form the dome-shaped members 961A, 961B in this way, a bottom portion of the base 956 would be removed and two-part molds would be inserted into the cylindrical projections 954A, 954B to form the dome-shaped members 961A, 961B. After forming the dome-shaped members 961A, 961B, the bottom portion of the base 956 would be re-attached.

While the membrane 140 has been described as extending over substantially the entire surface of the base 956, including the recessed regions 963A, 963B, in certain implementations, the membrane includes holes that align with the recessed regions 963A, 963B such that the piston heads directly contact the dome-shaped members 961A, 961B. In such implementations, the membrane is attached (e.g., thermally bonded or adhesively bonded) to the perimeter of each of the cylindrical members 954A, 954B to ensure a liquid-tight seal.

While the cassettes discussed above have been described as having two pump chambers, the cassettes can alternatively have more or fewer than two pump chambers.

While each of the pump chambers of the cassettes described above has been described as including a fluid inlet port and a fluid outlet port, the pump chambers can alternatively include a single port that is used as both an inlet and an outlet.

While the pistons described above have been described as having piston heads that are attached to shafts of the pistons, in certain implementations, the piston heads and shafts are integrally formed with one another. In some implementations, the piston heads are simply the flat end surfaces of the piston shafts themselves.

While certain cassettes have been described as being positioned between locating pins and a lower ledge extending from a cassette interface of the PD cycler in order to hold the cassette in a position such that the piston heads align with the pump chambers of the cassette, other techniques for ensuring that the piston heads align with the pump chambers can alternatively or additionally be used. In some implementations, for example, the cassette is placed against the door of the PD cycler with the hollow projections of the cassette disposed in recesses of the PD cycler's door. The cassette is held in this position by retainer clips attached to the door. Upon closing the door, the piston heads of the PD cycler align with the pump chambers of the cassette.

While certain PD cyclers above have been described as including a touch screen and associated buttons, the PD cycler can include other types of screens and user data entry systems. In certain implementations, for example, the cycler includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the doors of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation.

While some of the PD cyclers discussed above have been described as including inflatable pads in their doors to compress the cassette between the door and the cassette interface, the PD cyclers can alternatively or additionally include inflatable pads positioned behind the cassette interface.

While the cassettes described above have been described as being part of a PD system, these types of cassettes can be used in any of various other types of cassette-based medical fluid pumping systems. Other examples of medical fluid pumping systems with which cassettes described herein can be used include hemodialysis systems, blood perfusion systems, and intravenous infusion systems.

Similarly, while the cassettes have been described as being used to pump dialysis solution, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

What is claimed is:

1. A medical fluid pumping system, comprising:
    a medical fluid pumping machine defining a cassette enclosure, the medical fluid pumping machine comprising a movable piston; and
    a medical fluid cassette configured to be disposed within the cassette enclosure of the medical fluid pumping machine, the medical fluid cassette comprising
        a base;
        a membrane attached to the base, the membrane and a region of the base cooperating to define a fluid pump chamber, the cassette positionable within the cassette enclosure of the medical fluid pumping machine so that the membrane faces the piston and the membrane can be moved by the piston to decrease a volume of the fluid pump chamber; and
        a member disposed within the fluid pump chamber and configured to apply an outward force to an inner surface of the membrane to increase the volume of the fluid pump chamber, the member comprising a first portion defining a recess configured to receive the piston.

2. The medical fluid pumping system of claim 1, wherein the region of the base that together with the membrane defines the fluid pump chamber is a recessed region of the base.

3. The medical fluid pumping system of claim 1, wherein the membrane together with the base further defines a flow pathway that leads from the fluid pump chamber to an inlet of the cassette and a flow pathway that leads from the fluid pump chamber to an outlet of the cassette.

4. The medical fluid pumping system of claim 1, wherein the member is attached to the base of the cassette.

5. The medical fluid pumping system of claim 1, wherein the member further comprises a second portion attached to the first portion, the second portion being moveable between an expanded position and a compressed position.

6. The medical fluid pumping system of claim 5, wherein the second portion is substantially cup-shaped in the expanded position and substantially planar in the compressed position.

7. The medical fluid pumping system of claim 1, wherein the member comprises a second resilient portion attached to the first portion, the second resilient portion configured to resiliently move between an expanded position and a compressed position, and the first portion configured to apply the outward force to the membrane when the second resilient portion is moved from the compressed position to the expanded position.

8. The medical fluid pumping system of claim 7, wherein the second resilient portion is substantially cup-shaped in the expanded position and substantially planar in the compressed position.

9. The medical fluid pumping system of claim 7, wherein the second resilient portion is a cup-shaped member having a sidewall that defines a plurality of circumferentially spaced apertures.

10. The medical fluid pumping system of claim 1, wherein the member disposed within the fluid pump chamber is a substantially planar spring.

11. The medical fluid pumping system of claim 10, wherein the substantially planar spring comprises a hub portion and a plurality of circumferentially spaced legs extending radially outward from the hub portion.

12. The medical fluid pumping system of claim 11, wherein the substantially planar spring further comprises feet extending from ends of the legs opposite the hub portion, and at least one of the feet has a width that is greater than a width of the leg to which the at least one of the feet is attached.

13. The medical fluid pumping system of claim 12, wherein the at least one of the feet has a curved configuration that substantially conforms to an adjacent surface of the base.

14. The medical fluid pumping system of claim 10, wherein the substantially planar spring is formed of one or more metals.

15. The medical fluid pumping system of claim 1, further comprising a resilient device positioned between the base of the cassette and the member disposed in the fluid pump chamber of the cassette, the resilient device configured to apply a force to the member.

16. The medical fluid pumping system of claim 15, wherein the resilient device is configured to self-expand after being compressed.

17. The medical fluid pumping system of claim 16, wherein the resilient device comprises an elastomeric member.

18. The medical fluid pumping system of claim 1, wherein the medical fluid pumping machine comprises a device configured to apply a force to the member disposed in the fluid pump chamber when the cassette is disposed in the cassette enclosure.

19. The medical fluid pumping system of claim 18, wherein the device is a resilient device configured to self-expand after being compressed.

20. The medical fluid pumping system of claim 18, wherein the device comprises a spring.

21. The medical fluid pumping system of claim 18, wherein the member has a stem portion disposed within an aperture of the base of the cassette.

22. The medical fluid pumping system of claim 21, wherein the device contacts the stem portion when the cassette is disposed in the cassette enclosure.

23. The medical fluid pumping system of claim 22, further comprising an o-ring surrounding the stem portion, the o-ring compressed between the stem portion and a portion of the base defining the aperture in which the stem portion is disposed.

24. The medical fluid pumping system of claim 21, wherein the cassette further comprises a seal secured to the base and disposed over the aperture defined by the base.

25. The medical fluid pumping system of claim 24, wherein the device contacts the seal when the cassette is disposed in the cassette enclosure, the seal being deformable such that the force can be transmitted from the device to the stem portion of the member via the seal.

26. The medical fluid pumping system of claim 1, wherein the member is configured to create a vacuum pressure of about 150 mbar to about 200 mbar within the fluid pump chamber by applying the outward force to the membrane.

27. The medical fluid pumping system of claim 1, wherein the member is configured to apply an outward force of about 20N to about 100N to the membrane.

28. The medical fluid pumping system of claim 1, wherein the medical fluid pumping machine comprises first and second movable pistons, and the membrane and regions of the base cooperate to define first and second fluid pump chambers, the cassette is positionable within the cassette enclosure of the medical fluid pumping machine so that the membrane faces the first and second pistons and the membrane can be moved by the first and second pistons to decrease volumes of the first and second fluid pump chambers, and first and second members are disposed within the first and second fluid pump chambers, respectively, and are configured to apply outward forces to the inner surface of the membrane to increase the volumes of the first and second fluid pump chambers.

29. The medical fluid pumping system of claim 28, wherein the medical fluid pumping machine comprises a rod having a first end region and a second end region, the rod configured such that the first end region can apply a force to the first member disposed in the first fluid chamber and the second end region can apply a force to the second member disposed in the second fluid chamber.

30. The medical fluid pumping system of claim 29, wherein the rod is pivotable about a central pivot point such that when the first end region applies the force to the first member causing the first member to apply the outward force to the membrane, the second end region moves away from the second member, and when the second end region applies the force to the second member causing the second member to apply the outward force to the membrane, the first end region moves away from the first member.

31. The medical fluid pumping system of claim 1, wherein the medical fluid pumping system is a dialysis system.

32. A medical fluid cassette, comprising:
a base;
a membrane attached to the base, the membrane and a region of the base cooperating to define a fluid pump chamber; and
a member disposed within the fluid pump chamber and configured to apply an outward force to an inner surface of the membrane to increase a volume of the fluid pump chamber, the member comprising a first portion defining a recess configured to receive a piston of a medical fluid pumping machine.

33. The medical fluid cassette of claim 32, wherein the region of the base that together with the membrane defines the fluid pump chamber is a recessed region of the base.

34. The medical fluid cassette of claim 32, wherein the membrane together with the base further defines a flow pathway that leads from the fluid pump chamber to an inlet of the cassette and a flow pathway that leads from the fluid pump chamber to an outlet of the cassette.

35. The medical fluid cassette of claim 32, wherein the member further comprises a second portion attached to the first portion, the second portion being moveable between an expanded position and a compressed position.

36. The medical fluid cassette of claim 35, wherein the second portion is substantially cup-shaped in the expanded position and substantially planar in the compressed position.

37. The medical fluid cassette of claim 32, wherein the member comprises a second resilient portion attached to the first portion, the second resilient portion configured to resiliently move between an expanded position and a compressed position, and the first portion configured to apply the outward force to the membrane when the second resilient portion is moved from the compressed position to the expanded position.

38. The medical fluid cassette of claim 32, further comprising a resilient device positioned between the base of the cassette and the member disposed in the fluid pump chamber of the cassette, the resilient device configured to apply a force to the member.

39. The medical fluid cassette of claim 38, wherein the resilient device is configured to self-expand after being compressed.

40. The medical fluid cassette of claim 32, wherein the member has a stem portion disposed within an aperture of the base of the cassette.

41. The medical fluid cassette of claim 40, further comprising an o-ring surrounding the stem portion, the o-ring compressed between the stem portion and a portion of the base defining the aperture in which the stem portion is disposed.

42. The medical fluid cassette of claim 40, wherein the cassette further comprises a seal secured to the base and disposed over the aperture defined by the base.

* * * * *